(12) United States Patent
Dixit et al.

(10) Patent No.: US 10,508,154 B2
(45) Date of Patent: *Dec. 17, 2019

(54) PROCESS AND METHODS FOR EFFICIENT MANUFACTURING OF HIGHLY PURE ASYMMETRIC ANTIBODIES IN MAMMALIAN CELLS

(71) Applicant: Zymeworks Inc., Vancouver (CA)

(72) Inventors: Surjit Bhimarao Dixit, Richmond (CA); Gordon Yiu Kon NG, Vancouver (CA); Thomas Spreter Von Kreudenstein, Vancouver (CA)

(73) Assignee: ZYMEWORKS INC., Vancouver, BC (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/355,019

(22) Filed: Nov. 17, 2016

(65) Prior Publication Data

US 2017/0158779 A1 Jun. 8, 2017

Related U.S. Application Data

(63) Continuation of application No. 13/927,065, filed on Jun. 25, 2013, now Pat. No. 9,499,634.

(60) Provisional application No. 61/664,102, filed on Jun. 25, 2012.

(51) Int. Cl.
| | |
|---|---|
| *C12N 5/07* | (2010.01) |
| *C07K 16/46* | (2006.01) |
| *C07K 16/32* | (2006.01) |
| *C12P 21/00* | (2006.01) |

(52) U.S. Cl.
CPC .............. *C07K 16/46* (2013.01); *C07K 16/32* (2013.01); *C12P 21/005* (2013.01); *C07K 2317/14* (2013.01); *C07K 2317/41* (2013.01); *C07K 2317/52* (2013.01); *C07K 2317/526* (2013.01); *C07K 2317/64* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. |
| 5,624,821 A | 4/1997 | Winter et al. |
| 5,731,168 A | 3/1998 | Carter et al. |
| 5,807,706 A | 9/1998 | Carter et al. |
| 5,821,333 A | 10/1998 | Carter et al. |
| 5,885,573 A | 3/1999 | Bluestone et al. |
| 6,194,551 B1 | 2/2001 | Idusogie et al. |
| 6,268,488 B1 | 7/2001 | Barbas, III et al. |
| 6,331,415 B1 | 12/2001 | Cabilly et al. |
| 6,737,056 B1 | 5/2004 | Presta |
| 6,809,185 B1 | 10/2004 | Schoonjans et al. |
| 7,183,076 B2 | 2/2007 | Arathoon et al. |
| 7,635,472 B2 | 12/2009 | Kufer et al. |
| 7,642,228 B2 | 1/2010 | Carter |
| 7,695,936 B2 | 4/2010 | Carter et al. |
| 7,769,573 B2 | 8/2010 | Fejes et al. |
| 7,923,221 B1 | 4/2011 | Cabilly et al. |
| 7,951,917 B1 | 5/2011 | Arathoon |
| 8,501,185 B2 | 8/2013 | Heitner Hansen et al. |
| 8,592,562 B2 | 11/2013 | Kannan |
| 8,623,361 B2 | 1/2014 | Beirnaert et al. |
| 8,771,988 B2 | 7/2014 | Kopetzi et al. |
| 9,499,634 B2 | 11/2016 | Dixit et al. |
| 2003/0190311 A1 | 10/2003 | Dall'Acqua et al. |
| 2004/0071696 A1 | 4/2004 | Adams et al. |
| 2005/0069549 A1 | 3/2005 | Herman |
| 2005/0227324 A1 | 10/2005 | Huang et al. |
| 2006/0074225 A1 | 4/2006 | Chamberlain et al. |
| 2006/0106905 A1 | 5/2006 | Chren et al. |

(Continued)

FOREIGN PATENT DOCUMENTS

| | | |
|---|---|---|
| CA | 2548757 | 7/2005 |
| CN | 1176659 | 3/1998 |

(Continued)

OTHER PUBLICATIONS

U.S. Appl. No. 13/289,934, "Advisory Action", dated Feb. 5, 2016, 5 pages.
U.S. Appl. No. 13/289,934, "Non-Final Office Action", dated Feb. 27, 2015, 15 pages.
U.S. Appl. No. 13/289,934, "Non-Final Office Action", dated May 13, 2015, 19 pages.
U.S. Appl. No. 13/289,934, "Restriction Requirement", dated Sep. 16, 2014, 6 pages.
U.S. Appl. No. 13/289,934, "Notice of Allowance", dated Apr. 25, 2016, 9 pages.
U.S. Appl. No. 13/668,098, "Final Office Action", dated Nov. 17, 2015, 16 pages.
U.S. Appl. No. 13/668,098, "Non-Final Office Action", dated Apr. 3, 2015, 18 pages.

(Continued)

*Primary Examiner* — Michael D Burkhart
(74) *Attorney, Agent, or Firm* — Kilpatrick Townsend & Stockton LLP

(57) ABSTRACT

The present invention provides a process and methods for producing asymmetric antibodies in a mammalian expression system. The asymmetric antibodies are transiently or stably expressed and in cells that stably express the asymmetric antibody, following a rapid 2-step process of stable pool to clone, a highly pure asymmetric antibody expressing clone can be identified at a success frequency that permits for screening of tens of clones rather than thousands. The asymmetric antibodies are produced at a high titre and with a high level of purity with no contaminating homodimer antibodies following protein A purification with a step yield of near 100%. Typical downstream purification processes employ standard hydrophobic interaction chromatography (HIC) and/or cation exchange (CEX) resins and the antibody is stable within a wide dynamic range of buffer pH (4-8) and within the requirements for manufacturing antibodies for pre-clinical and clinical applications.

37 Claims, 37 Drawing Sheets

Specification includes a Sequence Listing.

(56) References Cited

U.S. PATENT DOCUMENTS

| | | |
|---|---|---|
| 2006/0160184 A1 | 7/2006 | Hoogenboom et al. |
| 2006/0263882 A1 | 11/2006 | Fazio et al. |
| 2007/0041987 A1 | 2/2007 | Carter et al. |
| 2007/0196363 A1 | 8/2007 | Arathoon et al. |
| 2007/0274985 A1 | 11/2007 | Dubel et al. |
| 2007/0276791 A1 | 11/2007 | Fejes et al. |
| 2007/0278170 A1 | 12/2007 | Wiebe |
| 2008/0050370 A1 | 2/2008 | Glaser et al. |
| 2008/0147360 A1 | 6/2008 | Fejes et al. |
| 2009/0162360 A1 | 6/2009 | Klein et al. |
| 2009/0182127 A1 | 7/2009 | Kjaergaard et al. |
| 2009/0226466 A1 | 9/2009 | Fong et al. |
| 2009/0232811 A1 | 9/2009 | Klein et al. |
| 2009/0263392 A1 | 10/2009 | Igawa et al. |
| 2010/0104564 A1 | 4/2010 | Hansen et al. |
| 2010/0105874 A1 | 4/2010 | Schuurman et al. |
| 2010/0149876 A1 | 6/2010 | Mokhlesi et al. |
| 2010/0166749 A1 | 7/2010 | Presta et al. |
| 2010/0196265 A1 | 8/2010 | Adams et al. |
| 2010/0256338 A1 | 10/2010 | Brinkmann et al. |
| 2010/0286374 A1 | 11/2010 | Kannan et al. |
| 2010/0322934 A1 | 12/2010 | Imhof-Jung et al. |
| 2010/0322935 A1 | 12/2010 | Croasdale et al. |
| 2010/0331527 A1 | 12/2010 | Davis et al. |
| 2011/0008345 A1 | 1/2011 | Ashman et al. |
| 2011/0053261 A1 | 3/2011 | Lario et al. |
| 2011/0059076 A1 | 3/2011 | McDonagh et al. |
| 2011/0200596 A1 | 8/2011 | Huang et al. |
| 2011/0274691 A1 | 11/2011 | Arvedson et al. |
| 2011/0275787 A1 | 11/2011 | Kufer et al. |
| 2011/0287009 A1 | 11/2011 | Scheer et al. |
| 2011/0293613 A1 | 12/2011 | Brinkmann et al. |
| 2012/0003221 A1 | 1/2012 | McDonagh et al. |
| 2012/0076728 A1 | 3/2012 | Wu et al. |
| 2012/0149876 A1 | 6/2012 | Von Kreudenstein et al. |
| 2012/0244577 A1 | 9/2012 | Dixit et al. |
| 2012/0244578 A1 | 9/2012 | Kannan |
| 2012/0270801 A1 | 10/2012 | Frejd et al. |
| 2013/0078249 A1 | 3/2013 | Ast et al. |
| 2013/0195849 A1 | 8/2013 | Spreter Von Kreudenstein et al. |
| 2013/0238299 A1 | 9/2013 | Ohrn et al. |
| 2013/0245963 A1 | 9/2013 | Ohrn et al. |
| 2013/0336973 A1 | 12/2013 | Spreter Von Kreudenstein et al. |
| 2014/0066378 A1 | 3/2014 | Dixit et al. |
| 2014/0072581 A1 | 3/2014 | Dixit et al. |
| 2014/0154253 A1 | 6/2014 | Ng et al. |
| 2014/0199294 A1 | 7/2014 | Mimoto et al. |
| 2014/0200331 A1 | 7/2014 | Corper et al. |
| 2015/0051889 A1 | 2/2015 | Ohrn et al. |
| 2015/0125449 A1 | 5/2015 | Ng et al. |
| 2015/0142326 A1 | 5/2015 | Lakatos et al. |
| 2015/0220681 A1 | 8/2015 | Dixit |
| 2015/0284470 A1 | 10/2015 | Spreter Von et al. |
| 2015/0307594 A1 | 10/2015 | Corper et al. |
| 2016/0083480 A1 | 3/2016 | Ng et al. |
| 2016/0114057 A1 | 4/2016 | Dixit et al. |
| 2016/0257763 A1 | 9/2016 | Von Kreudenstein et al. |
| 2016/0289328 A1 | 10/2016 | Ng et al. |
| 2016/0289335 A1 | 10/2016 | Weisser et al. |
| 2016/0297891 A1 | 10/2016 | Ng et al. |
| 2016/0355588 A1 | 12/2016 | Ng et al. |
| 2017/0158779 A1* | 6/2017 | Dixit ............... C07K 16/32 |

FOREIGN PATENT DOCUMENTS

| | | |
|---|---|---|
| EP | 368684 | 5/1990 |
| EP | 1870459 | 12/2007 |
| HK | 1200465 | 8/2015 |
| JP | 2011508604 | 3/2011 |
| WO | 9308829 | 5/1993 |
| WO | 9404690 | 3/1994 |
| WO | 96027011 | 9/1996 |
| WO | 9734631 | 9/1997 |
| WO | 9958572 | 11/1999 |
| WO | 0042072 | 7/2000 |
| WO | 03031464 | 4/2003 |
| WO | 2004029207 | 4/2004 |
| WO | 2004068820 | 8/2004 |
| WO | 2005018629 | 3/2005 |
| WO | 2006003388 | 1/2006 |
| WO | 2006030220 | 3/2006 |
| WO | 2007110205 | 10/2007 |
| WO | 2008131242 | 10/2008 |
| WO | 2009089004 | 7/2009 |
| WO | 2010068722 | 6/2010 |
| WO | 2010085682 | 7/2010 |
| WO | 2010115553 | 10/2010 |
| WO | 2011005621 | 1/2011 |
| WO | 2011028952 | 3/2011 |
| WO | 2011063348 | 5/2011 |
| WO | 2011066655 | 6/2011 |
| WO | 2011120134 | 10/2011 |
| WO | 2011120135 | 10/2011 |
| WO | 2011131749 | 10/2011 |
| WO | 2011133886 | 10/2011 |
| WO | 2011143545 | 11/2011 |
| WO | 2011147982 | 12/2011 |
| WO | 2012143523 | 12/2011 |
| WO | 2012006635 | 1/2012 |
| WO | 2012037659 | 3/2012 |
| WO | 2012040833 | 4/2012 |
| WO | 2012058768 | 5/2012 |
| WO | 2012116453 | 9/2012 |
| WO | 2013002362 | 1/2013 |
| WO | 2013063702 | 5/2013 |
| WO | 2013166594 | 11/2013 |
| WO | 2013166604 | 11/2013 |
| WO | 2014004586 | 1/2014 |
| WO | 2014012082 | 1/2014 |
| WO | 2014012085 | 1/2014 |
| WO | 2014018572 | 1/2014 |
| WO | 2014067011 | 5/2014 |
| WO | 2014082179 | 6/2014 |
| WO | 2014182970 | 11/2014 |
| WO | 2014186905 | 11/2014 |
| WO | 2015006749 | 1/2015 |
| WO | 2015181805 | 5/2015 |

OTHER PUBLICATIONS

U.S. Appl. No. 13/668,098, "Restriction Requirement", dated Dec. 5, 2014, 10 pages.

U.S. Appl. No. 13/892,198, "Non-Final Office Action", dated Oct. 6, 2015, 23 pages.

U.S. Appl. No. 13/892,198, "Restriction Requirement", dated Jul. 10, 2015, 12 pages.

U.S. Appl. No. 13/941,449, "Restriction Requirement", dated Dec. 3, 2015, 10 pages.

U.S. Appl. No. 13/941,449, "Non-Final Office Action", dated Apr. 13, 2016, 41 pages.

U.S. Appl. No. 13/949,166, "Final Office Action", dated Aug. 21, 2015, 12 pages.

U.S. Appl. No. 13/949,166, "Non-Final Office Action", dated Apr. 14, 2015, 22 pages.

U.S. Appl. No. 13/949,166, "Restriction Requirement", dated Dec. 16, 2014, 9 pages.

U.S. Appl. No. 13/949,166, "Final Office Action", dated Jun. 16, 2016, 27 pages.

U.S. Appl. No. 13/949,166, "Non-Final Office Action", dated Jan. 13, 2016, 12 pages.

U.S. Appl. No. 14/092,804, "Non-Final Office Action", dated Sep. 10, 2015, 33 pages.

U.S. Appl. No. 14/092,804, "Restriction Requirement", dated Jun. 18, 2015, 5 pages.

U.S. Appl. No. 14/092,804, "Restriction Requirement", dated May 12, 2016, 5 pages.

U.S. Appl. No. 14/399,789, "Non-Final Office Action", dated Dec. 17, 2015, 31 pages.

U.S. Appl. No. 14/399,789, "Restriction Requirement", dated Sep. 14, 2015, 11 pages.

(56) References Cited

OTHER PUBLICATIONS

U.S. Appl. No. 14/399,789, "Final Office Action", dated Jul. 20, 2016, 30 pages.
U.S. Appl. No. 14/648,222, "Restriction Requirement", dated May 9, 2016, 14 pages.
U.S. Appl. No. 14/888,580, filed Nov. 2, 2015, Titled: Bispecific HER2 and HER3 Antigen Binding Constructs.
U.S. Appl. No. 14/893,706, filed Nov. 24, 2015, Titled: Modular Protein Drug Conjugate Therapeutic.
U.S. Appl. No. 14/903,184, "Bispecific CD3 and CD19 Antigen Binding Constructs", U.S. Appl. No. filed Jan. 6, 2016.
U.S. Appl. No. 14/989,648, Heteromultimer Constructs of Immunoglobulin Heavy Chains with Mutations in the FC Domain, Jan. 6, 2016.
Aitman et al., "Copy number polymorphism in Fcgr3 predisposes to glomerulonephritis in rats and humans", Nature, vol. 439, No. 7078, Feb. 16, 2006, pp. 851-855.
Alegre et al., "A non-activating "humanized" anti-CD3 monoclonal antibody retains immunosuppressive properties in vivo", Transplantation, vol. 57(11), Jun. 15, 1994, pp. 1537-1543.
Altintas et al., "Targeting epidermal growth factor receptor in tumors: from conventional monoclonal antibodies via heavy chain-only antibodies to nanobodies", Eur J Pharm Sci., vol. 45, No. 4, Oct. 28, 2011, pp. 399-407.
Arnold et al. "The impact of glycosylation on the biological function and structure of human immunoglobulins." Annu Rev Immunol. 25:21-50 (2007).
Atwell et al., "Stable heterodimers from remodeling the domain interface of a homodimer using a phage display library", Journal of Molecular Biology, vol. 270, No. 1, Jul. 4, 1997, pp. 26-35.
Barthelemy et al., "Comprehensive analysis of the factors contributing to the stability and solubility of autonomous human VH domains", J. Bioi. Chem., vol. 283, No. 6, Feb. 2008, pp. 3639-3654.
Beck et al., "Strategies and challenges for the next generation of therapeutic antibodies", Nature Reviews Immunology, vol. 10, No. 5, May 2010, pp. 345-352.
Bell et al., "Differential tumor-targeting abilities of three single-domain antibody formats", Cancer Letters, vol. 289, 2009, pp. 81-90.
Bolon et al., "Specificity versus stability in computational protein design", Proceedings of the National Academy of Sciences, vol. 102, No. 36, Sep. 6, 2005, pp. 12724-12749.
Carter et al. "Humanization of an Andi PI85 Her2 antibody for Human Cancer Therapy." Proc Natl Acad Sci 89: 4285 (1992).
Carter, "Introduction to current and future protein therapeutics: A protein engineering perspective", Experimental Cell Research, vol. 317, No. 9, May 15, 2011, pp. 1261-1269.
Chames et al., "Therapeutic antibodies: successes, limitations and hopes for the future", British Journal of Pharmacology, vol. 157, No. 2, 2009, pp. 220-223.
Cochlovius et al., "Treatment of human B cell lymphoma xenografts with a CD3 x CD19 diabody and T cells", Journal of Immunology, vol. 165, No. 2, 2000, pp. 888-895.
Colbere-Garapin et al., "A new dominant hybrid selective marker for higher eukaryotic cell", Journal of Molecular Biology, vol. 150, No. 1, Jul. 25, 1981, pp. 1-14.
Colman, "Effects of amino acid sequence changes on antibody-antigen interactions", Research in Immunology, vol. 145, No. 1, 1994, 33-36.
Coloma et al., "Design and production of novel tetravalent bispecific antibodies", Nature Biotechnology, vol. 15, No. 2, Feb. 1997, pp. 159-163.
Dall'Acqua et al., "Contribution of Domain Interface Residues to the Stability of Antibody CH3 Domain Homodimers", Biochemistry, American Chemical Society, US, vol. 37, No. 26, Jun. 30, 1998, pp. 9266-9273.
Davis et al. "SEEDbodies: fusion proteins based on strand-exchange engineered domain (SEED) CH3 heterodimers in an Fc analogue platform for asymmetric binders or immunofusions and bispecific antibodies." Protein Eng Des Sel. 23(4):195-202.(2010) (Published online Feb. 4, 2010 at: doi: 10.1093/protein/gzp094.).
Demarest et al., "Antibody therapeutics, antibody engineering, and the merits of protein stability", Current Opinion in Drug Discovery and Development vol. 11, No. 5, Sep. 2008, pp. 675-687.
Demarest et al., "Optimization of the Antibody CH3 Domain by Residue Frequency Analysis of IgG Sequences", Journal of Molecular Biology, vol. 335, No. 1, Jan. 2, 2004, pp. 41-48.
Dockal et al., "Conformational Transitions of the Three Recombinant Domains of Human Serum Albumin Depending on pH", The Journal of Biological Chemistry, vol. 275, No. 5, Feb. 4, 2000, pp. 3042-3050.
Dockal et al., "Five recombinant fragments of human serum albumin-tools for the characterization of the warfarin binding site", Protein Science, vol. 9, No. 8, 2000, pp. 1455-1465.
Ducry et al., "Antibody-drug conjugates: linking cytotoxic payloads to monoclonal antibodies", Bioconjugate Chem., vol. 21, Issue 1, Jan. 2010, pp. 5-13.
Duncan et al., "Localization of the binding site for the human high-affinity FC receptor on IgG", Nature, vol. 332, No. 7, 1988, pp. 563-564.
Durocher et al. "High-level and high-throughput recombinant protein production by transient transdection fo suspension-growing human HEK293-EBNA1 cells." Nucleic acids research 30: E9 (2002).
EP11837370.3, "Extended European Search Report", dated Apr. 29, 2014, 14 pages.
EP12845801.5, "Extended European Search Report", dated May 8, 2015, 7 pages.
EP13788302.1, "Extended European Search Report", dated Nov. 18, 2015, 9 pages.
Grabulovski et al., "A novel, non-immunogenic Fyn SH3-derived binding protein with tumor vascular targeting properties", J Bioi Chem., vol. 282, No. 5, Feb. 2007, pp. 3196-3204.
Groot et al., "Identification by phage display of single-domain antibody fragments specific for the ODD domain in hypoxia-inducible factor 1 alpha", Lab Invest vol. 86, No. 4, Apr. 2006, pp. 345-356.
Gunasekaran et al. "Enhancing antibody Fc heterodimer formation through electrostatic steering effects: applications to bispecific molecules and monovalent IgG." J Biol Chem. 285(25):19637-46 (2010).
Guss et al. "Structure of the IgG-binding regions of streptococcal protein G." Embo J. 5(7):1567-75 (1986).
Hardy et al., "Valency of Antibody Binding to Enveloped Virus Particles as Determined by Surface Plasmon Resonance", J Viral., vol. 77, No. 2, 2003, pp. 1649-1652.
Havranek et al., "Automated design of specificity in molecular recognition", Nature Structure Biology, vol. 10, No. 1, Jan. 2003, pp. 45-52.
Hennecke et al. "Composition and arrangement of genes define the strength of IRES-driven translation in bicistronic mRNAs." Nucl. Acids Res. 29: 3327-3334 (2001).
Holt et al., "Domain antibodies: proteins for therapy", Trends in Biotechnology, Elsevier Publications, Cambridge, GB, vol. 21, No. 11, Nov. 2003, pp. 484-490.
Huang et al., "A de novo designed protein protein interface", Protein Science, vol. 16, No. 12, 2007, pp. 2770-2774.
Hust et al., "Single chain Fab (scFab) fragment", BMC Biotechnology, vol. 7, No. 14. Available online at httn://www.biomedcentral.com/1472-6750/7/14, 2007, pp. 1-15.
Hutchins et al., "Improved biodistribution, tumor targeting, and reduced immunogenicity in mice with a gamma 4 variant of Campath-1H.", Proc. Natl. Acad. Sci., vol. 92, No. 26, Dec. 1995, pp. 11980-11984.
Idusogie et al., "Engineered antibodies with increased activity to recruit complement", J. Immunol., vol. 166, No. 4, Feb. 15, 2001, pp. 2571-2575.
Idusogie et al., "Mapping of the C1q binding site on rituxan, a chimeric antibody with a human IgG1 Fc", J. Immunol., vol. 164, No. 8, Apr. 15, 2000, pp. 4178-4184.
Igawa et al., "VH/VL interface engineering to promote selective expression and inhibit conformational isomerization of thrombopoietin

(56) References Cited

OTHER PUBLICATIONS receptor against single-chain diabody", Protein Engineering, Design & Selection, vol. 23, No. 8, Aug. 2010, pp. 667-677.
Jackman et al. "Development of a two-part strategy to identify a therapeutic human bispecific antibody that inhibits IgE receptor signaling." J. biol. Chem. 285: 20850-20859 (2010).
Janeway et al., "Structure of the Antibody Molecule and Immunoglobulin Genes", Immunology Third Edition, Garland Publishing Inc. Chapter 3, tructure of the Antibody Molecule and Immunoglobulin Genes, 1997, pp. 3:1-3:11.
Jefferis et al., "Interaction sites on human IgG-Fc for FcgammaR: current models", Immunol. Lett., vol. 82, No. 1-2, 2002, pp. 57-65.
Jefferis et al., "Modulation ofFc(gamma)R and human complement activation by IgG3-core oligosaccharide interactions", Immunol. Lett., vol. 54, No. 2-3, Dec. 1996, pp. 101-104.
Jefferis et al., "Recognition sites on human IgG for Fc gamma receptors: the role of glycosylation", Immunol. Lett., vol. 44, No. 2-3, 1995, pp. 111-117.
Jin et al. "MetMAb, the one-armed 5D5 anti-c-met antibody, inhibits orthotopic pancreatic tumor growth and improves survival." Cancer Res 68:4360-4368 (2008).
Kang et al., "Engineering multivalent antibodies to target heregulin-induced HER3 signaling in breast cancer cells", MAbs, vol. 6, 2013, pp. 340-353.
Kelley, "Very large scale monoclonal antibody purification: the case for conventional unit operations", Biotechnology Progress, vol. 23, No. 5, Sep.-Oct. 2007, pp. 995-1008.
Klein et al., "Progress in overcoming the chain association issue in bispecific heterodimeric IgG antibodies", MABS, vol. 4, No. 6, Nov./Dec. 2012, pp. 653-663.
Kontermann, "Dual targeting strategies with bispecific antibodies," mABs vol. 4, No. 2, 2012, pp. 182-197.
De Kruif et al., "Leucine zipper dimerized bivalent and bispecific scFv antibodies from a semi-synthetic antibody phage display library", Journal of Biological Chemistry, vol. 271, No. 13, Mar. 29, 1996, pp. 7630-7634.
Lewis et al., "Generation of bispecific IgG antibodies by structura-based design of an orthogonal Fab interface", Nature Biotechnology, Jan. 26, 2014, pp. 1-12.
Li et al., "Bispecific antibody to ErbB2 overcomes trastuzumab resistance through comprehensive blockade of ErbB2 heterodimerization", Cancer Research, vol. 73, No. 21, Sep. 2013, pp. 6471-6483.
Lindhofer et al., "Preferential species-restricted heavy/light chain pairing in rat/mouse quadromas. Implications for a single-step purification of bispecific antibodies", The Journal of Immunology. 155, No. 1, Jul. 1, 1995, pp. 219-225.
Lorusso et al., "Trastuzumab emtansine: a unique antibody-drug conjugate in development for human epidermal growth factor receptor 2-positive cancer", Clinical Cancer Research, vol. 17, Issue 20, Oct. 15, 2011, pp. 6437-6447.
Lu et al., "Fab-scFv fusion protein: an efficient approach to production of bispecific antibody fragments", Journal of Immunological Methods, vol. 267, No. 2, 2002, pp. 213-226.
Lund et al., "Human Fc gamma RI and Fc gamma RII interact with distinct but overlapping sites on human IgG", J. Immunol., vol. 147, No. 8, Oct. 15, 1991, pp. 2657-2662.
Lund et al., "Multiple binding sites on the CH2 domain ofIgG for mouse Fc gamma R11", Mol. Immunol., vol. 29, No. 1, 1992, pp. 53-59.
Lund et al., "Multiple interactions ofIgG with its core oligosaccharide can modulate recognition by complement and human Fc gamma receptor I and influence the synthesis of its oligosaccharide chains", J. Immunol., vol. 157, No. 11, 1996, pp. 4963-4969.
Lund et al., "Oligosaccharide-protein interactions in IgG can modulate recognition by Fc gamma receptors", FASEB J., vol. 9, No. 1, Jan. 1995, pp. 115-119.
MacCallum et al., "Antibody-antigen interactions: Contact analysis and binding site topography", Journal of Molecular Biology, vol. 262 (5), Oct. 1996, pp. 732-745.

Marqusee et al., "Helix stabilization by Glu- . . . Lys+ salt bridges in short peptides of de novo design", Proc Natl Acad Sci U S A., No. 84, No. 24, 1987, pp. 8898-8902.
McDonagh et al., "Antitumor activity of a novel bispecific antibody that targets the ErbB2/ErbB3 oncogenic unit and inhibits heregulin-induced activation of ErbB3", Mol. Cancer Ther., vol. 11, No. 3, Jan. 2012, pp. 582-593.
Merchant et al. "An efficient route to human bispecific IgG." Nature Biotechnology. 16(7):677-81 (1998).
Milstein et al., "Hybrid hybridomas and their use in immunohistochemistry", Nature, vol. 305, No. 6, Oct. 6, 1983, pp. 537-540.
Moore et al. "Engineered Fc variant antibodies with enhanced ability to recruit complement and mediate effector functions." mAbs 2(2):181-189 (2010).
Moore et al., "A novel bispecific antibody format enables simultaneous bivalent and monovalent co-engagement of distinct target antigens", MAbs, vol. 3, No. 6, 2011, pp. 546-557.
Omidfar et al., "Single domain antibodies: a new concept for epidermal growth factor receptor and EGFRvIII targeting", DNA Cell Biol, vol. 31, No. 6, Jun. 2012, pp. 1015-1026.
Omidfar et al., "Studies of thermostability in Camelus bactrianus (Bactrian camel) single-domain antibody specific for the mutant epidermal-growth-factor receptor expressed by Pichia.", Biotechnol. Appl. Biochem., vol. 46, Jan. 2007, pp. 41-49.
Osborn et al., "Pharmacokinetic and Pharmacodynamics Studies of a Human Serum Albumin-Interferon-A Fusion Protein in Cynomolgus Monkeys", J. Pharamcology and Experiemental Therapeutics, vol. 330, 2002, pp. 540-548.
Paul, "Protein and polypeptide antigenic determinants", Fundamental Immunology, 3d ed, 1993, p. 242.
PCT/US2013/047725 International Preliminary Report on Patentability dated Dec. 31, 2014.
PCT/CA2011/000321, "International Search Report and Written Opinion", dated Jul. 15, 2011, 15 pages.
PCT/CA2011/000322, "International Search Report and Written Opinion", dated Jun. 27, 2011, 15 pages.
PCT/CA2011/001238, "International Search Report and written opinion", dated Jan. 26, 2012, 16 pages.
PCT/CA2012/050131, "International Search Report and Written Opinion", dated May 23, 2012, 9 pages.
PCT/CA2012/050780, "Search Report and written opinion", dated Feb. 14, 2013, 17 pages.
PCT/CA2013/000471, "International Search Report and Written Opinion", dated Aug. 15, 2013, 12 pages.
PCT/CA2013/050358, "International Search Report and Written Opinion", dated Jul. 30, 2013, 19 pages.
PCT/CA2013/050832, International Search Report and Written Opinion, dated Jan. 23, 2014, 10 pages.
PCT/CA2013/050914, "International Search Report and Written Opinion", dated Feb. 7, 2014, 11 pages.
PCT/CA2014/050486, International Search Report and Written Opinion, dated Jan. 23, 2014, 10 pages.
PCT/CA2014/051140, "International Search Report and Written Opinion", dated Feb. 18, 2015, 17 pages.
PCT/US2013/047725 Search Report and Written Opinion dated Nov. 22, 2013.
PCT/US2013/050408, "International Search Report and Written Opinion", dated Feb. 6, 2014, 14 pages.
PCT/US2013/050411, "International Search Report and Written Opinion", dated Jan. 29, 2014, 19 pages.
PCT/US2013/051747, "International Search Report and Written Opinion", dated Feb. 3, 2014, 14 pages.
PCT/US2014/046436, "International Search Report and Written Opinion", dated Jan. 2, 2015, 15 pages.
PCT/US2014/065571, "International Search Report and Written Opinion", dated Feb. 19, 2015, 13 pages.
Pham et al. Large-scale transfection of Mammalian cells for the Production of Recombinant Protein. Mol Biotechnol. 34(2): 225-237 (2006).
Pluckthun, "Antibodies from *Escherichia coli* . In: The Pharmacology of Monoclonal Antibodies", Rosenburg and Moore eds, Springer-Verlag, vol. 113, chapter 11, 1994, pp. 269-315.

(56) References Cited

OTHER PUBLICATIONS

Portolano et al., "Lack of promiscuity in autoantigen-specific H and L chain combinations as revealed by human H and L chain "roulette".", J Immunol., vol. 150, No. 3, Feb. 1, 1993, pp. 880-887.
Presta et al., "Engineering therapeutic antibodies for improved function", Biochem. Soc. Trans., vol. 30, No. 4, Aug. 2002, pp. 487-490.
PT/US2014/037401, "International Search Report and Written Opinion", dated Oct. 7, 2014, 14 pages.
Rakestraw et al., "Secretion-and-capture cell-surface display for selection of target-binding proteins", Protein Engineering, Design and Selection, vol. 24, No. 6, 2011, pp. 525-530.
Raymond et al. "A simplified polyethlyenimine-mediated transfection process for large-scale and high-throughput applications. Methods." 55(1 ): 44-51 (2011).
Reddy et al., "Elimination of Fc receptor-dependent effector functions of a modified IgG4 monoclonal antibody to human CD4", J. Immunol., vol. 164, No. 4, Feb. 15, 2000, pp. 1925-1933.
Ridgway et al. "'Knobs-into-holes' engineering of antibody CH3 domains for heavy chain heterodimerization." Protein Eng. 9(7):617-21 (1996).
Robinson et al., "Targeting ErbB2 and ErbB3 with a bispecific single-chain Fv enhances 1-5 targeting selectivity and induces a therapeutic effect in vitro", Br. J. Cancer, vol. 99, Oct. 7, 2008, 1415-1425.
Rudikoff et al., "Single Amino Acid Substitution altering Antigen-binding Specificity", Proc. Natl Acad Sci., vol. 79, No. 6, 1982, pp. 1979-1983.
Segal et al., "Introduction: bispecific antibodies", Journal of Immunological Methods, vol. 248, No. 1-2, Feb. 1, 2001, pp. 1-6.
Shields et al., "High resolution mapping of the binding site on human IgG1 for Fc gamma RI, Fc gamma RII, Fc gamma RIII, and FcRn and design of IgG1 variants with improved binding to the Fc gamma R", Journal of Biological Chemistry, vol. 276, No. 9, Mar. 2, 2001, pp. 6591-6604.
Stancovski et al., "Mechanistic Aspects of the Opposing effects of Monoclonal Antibodies to the ERBB2 receptor on Tumor Growth", Proceedings of the National Academy of Sciences, vol. 88, Nov. 1991, pp. 8691-8695.
Stanglmaier et al., "A Novel Trifunctional Bispecific Antibody (anti-CD20 3 anti-CD3), Mediates Efficient Killing of B-cell Lymphoma Cells Even With Very Low CD20 Expression Levels", International Journal of Cancer, vol. 123, 2008, pp. 1181-1189.
Strohl et al. "Cell line development." In: Therapeutic Antibody Engineering, Cambridge Woodhead Publishing, p. 420-437 (2012).
Strop et al., "Generating bispecific human IgG1 and IgG2 antibodies from any antibody pair," J. Mol. Biol. vol. 420, No. 3, 2012, pp. 204-219.
Suresh et al., "Bispecific monoclonal antibodies from hybrid hybridomas", Methods in Enzymology, vol. 121, 1983, pp. 210-228.
Tamaskovic et al., "Designed ankyrin repeat proteins (DARPins): From research to therapy", Methods in Enzymology, vol. 503, 2012, pp. 101-134.
Traunecker et al., "Bispecific single chain molecules (Janusins) target cytotoxic lymphocytes on HIV infected cells", EMBO Journal, vol. 10, No. 12, Dec. 1991, pp. 3655-3699.
Troise et al., "Differential binding of human immunoagents and Herceptin to the ErbB2 receptor", FEBS Journal, vol. 275, No. 20, 2008, pp. 4967-4979.
Verheesen et al., "Selection by phage display of single domain antibodies specific to antigens in their native conformation", Methods Mol Bioi, vol. 911, chapter 6, 2012, pp. 81-104.
Vie et al., "Human fusion proteins between interleukin 2 and IgM heavy chain are cytotoxic for cells expressing the interleukin 2 receptor", Proc. Natl. Acad. Sci., vol. 89, 1992, pp. 11337-11341.
Vitetta et al., "Considering Therapeutic Antibodies", Immunology, Science, 2006, vol. 313, No. 5785, 2006, pp. 308-309.
Von Kreudenstein et al., "Protein engineering and the use of molecular modeling and simulation: the case of heterodimeric Fc engineering", Methods, vol., 65, No. 1, Jan. 1, 2014, pp. 77-94.

Wang, "Protein aggregation and its inhibition in biopharmaceutics", International Journal of Pharmaceutics, vol. 289, No. 1-2, Jan. 31, 2005, pp. 1-30.
Ward et al., "Binding activities of a repertoire of single immunoglobulin variable domains secreted from *Escherichia coli* ", Nature, 334, 1989, pp. 544-546.
Wesolowski et al., "Single domain antibodies: promising experimental and therapeutic tools in infection and immunity", Med Microbiol Immunol., vol. 198, No. 3, 2009, pp. 157-174.
Wiens et al., "Mutation of a single conserved residue in VH complementarity-determining region 2 results in a severe Ig secretion defect.", J Immunology, vol. 167, No. 4, Aug. 2001, pp. 2179-2186.
Woods et al., "LC-MS characterization and purity assessment of a prototype bispecific antibody", MABS, vol. 5, No. 5, Sep. 1, 2013, pp. 711-722.
Wu et al., "Arming antibodies: prospects and challenges for immunoconjugates", Nature Biotech., vol. 23, Issue 9, Sep. 2005, pp. 1137-1146.
Wu et al., "Humanization of a Murine Monoclonal Antibody by Simultaneous Optimization of Framework and CDR Residues", Journal of Molecular Biology, vol. 294, Nov. 1999, pp. 151-62.
Xu et al., "In vitro characterization of five humanized OKT3 effector function variant antibodies", Cell. Immunol., vol. 200, No. 1, Feb. 25, 2000, pp. 16-26.
Zhu et al., "Remodeling domain interfaces to enhance heterodimer formation", Protein Science, vol. 6, No. 4, Apr. 1997, pp. 781-788.
U.S. Appl. No. 14/092,804, Final Office Action dated Dec 29, 2016.
U.S. Appl. No. 14/092,804, Notice of Allowance dated Jan. 11, 2017.
U.S. Appl. No. 14/648,222, Restriction Requirement dated May 9, 2016.
U.S. Appl. No. 14/648,222, Restriction Requirement dated Dec. 2, 2016.
U.S. Appl. No. 14/648,222, Office Action dated May 16, 2017.
U.S. Appl. No. 14/648,222, Final Office Action dated Dec. 29, 2017.
U.S. Appl. No. 13/941,449, Final Office Action dated Oct. 31, 2016.
U.S. Appl. No. 13/941,449, Office Action dated Dec. 21, 2017.
U.S. Appl. No. 14/903,184, filed Jul. 11, 2014 (US 20160355588; ZW; Dec. 8, 2016).
U.S. Appl. No. 14/903,184, Restriction Requirement dated Jun. 23, 2017.
U.S. Appl. No. 14/903,184, Office Action dated Feb. 2, 2018.
U.S. Appl. No. 15/741,984, filed Jul. 15, 2016 (new NPE, not pub yet), application can be found in IFW in Pair.
U.S. Appl. No. 15/036,176, filed Nov. 11, 2014 (US 20160289335; ZW; Oct 6, 2016).
U.S. Appl. No. 15/036,176, Restriction Requirement dated Jul. 28, 2017.
U.S. Appl. No. 15/036,175, (US 20160297891; ZW; Oct 13, 2016).
U.S. Appl. No. 15/572,362, filed May 13, 2016 (new NPE, not pub yet), application can be found in IFW in Pair.
U.S. Appl. No. 15/526,888, filed Nov. 26, 2015 (new NPE, not pub yet), application can be found in IFW in Pair.
U.S. Appl. No. 15/036,174, filed Nov. 13, 2014 (US 20160289328; ZW, Oct. 6, 2016).
U.S. Appl. No. 15/036,174, Restriction Response dated Jul. 20, 2017.
U.S. Appl. No. 15/036,174, Office Action dated Dec. 14, 2017.
U.S. Appl. No. 14/888,580, Restriction Response dated Jan. 30, 2017.
U.S. Appl. No. 14/888,580, Office Action dated Apr. 12, 2017.
U.S. Appl. No. 14/888,580, Final Office Action dated Sep. 7, 2017.
U.S. Appl. No. 13/892,198, Restriction Requirement dated Jan. 9, 2018.
U.S. Appl. No. 14/439,532, Restriction Requirement dated Nov. 8, 2011.
U.S. Appl. No. 14/439,532, Notice of Allowance dated Feb. 9, 2017.
U.S. Appl. No. 14/439,532; Notice of Allowance dated May 19, 2017.
U.S. Appl. No. 14/893,706, Restriction Requirement dated Apr. 4, 2017.
U.S. Appl. No. 14/893,706, Office Action dated Jun. 30, 2017.

(56) References Cited

OTHER PUBLICATIONS

U.S. Appl. No. 15/409,456 Restriction Requirement dated Jan. 10, 2019; 9 pgs.
U.S. Appl. No. 15/411,799 Restriction Requirement dated Jan. 25, 2019; 9 pgs.

* cited by examiner

FIG. 1

| Pools | LC % | HC % | |
|---|---|---|---|
| | | Chain A | Chain B |
| J | 50 | 33.3 | 16.7 |
| K | 50 | 25 | 25 |
| L | 50 | 16.7 | 33.3 |
| M | 60 | 26.7 | 13.3 |
| N | 60 | 20 | 20 |
| O | 60 | 13.3 | 26.7 |
| P | 40 | 40 | 20 |
| Q | 40 | 30 | 30 |
| R | 40 | 20 | 40 |

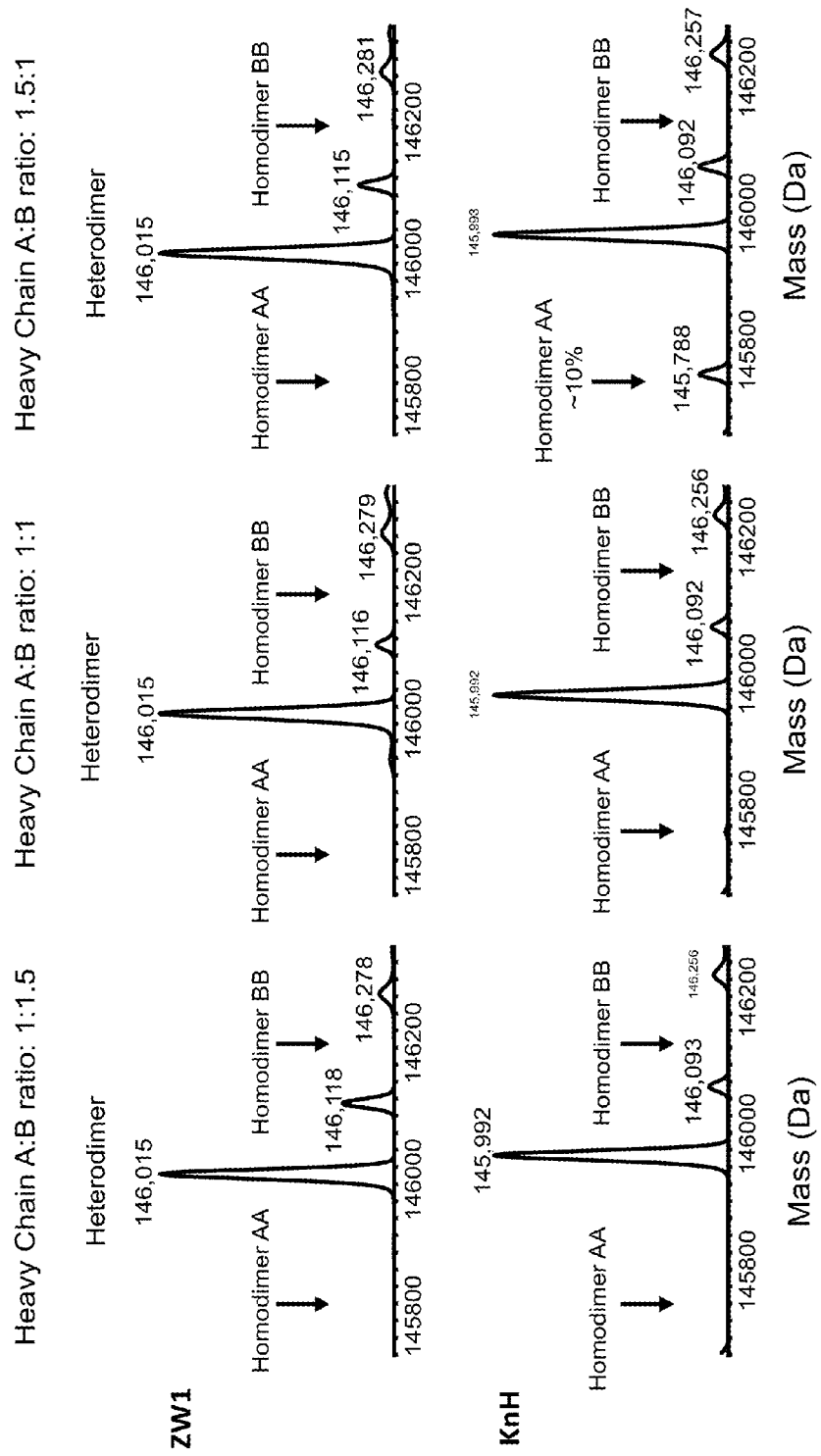

FIG. 6A
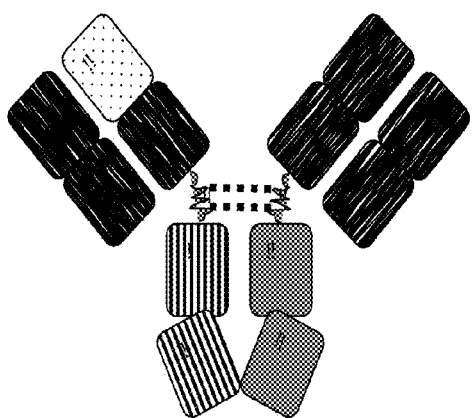
Asymmetric form of the antibody
FIG. 6B  FIG. 6C
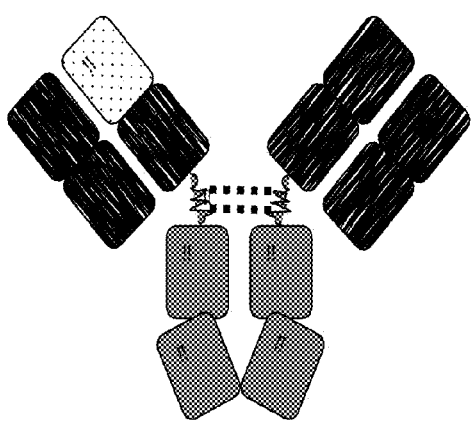 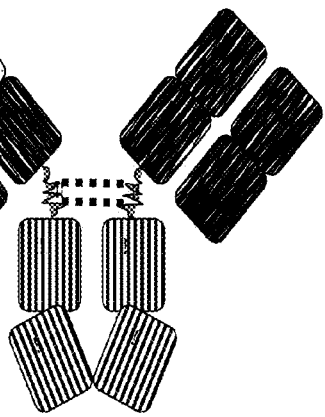
Two symmetric forms of the antibody

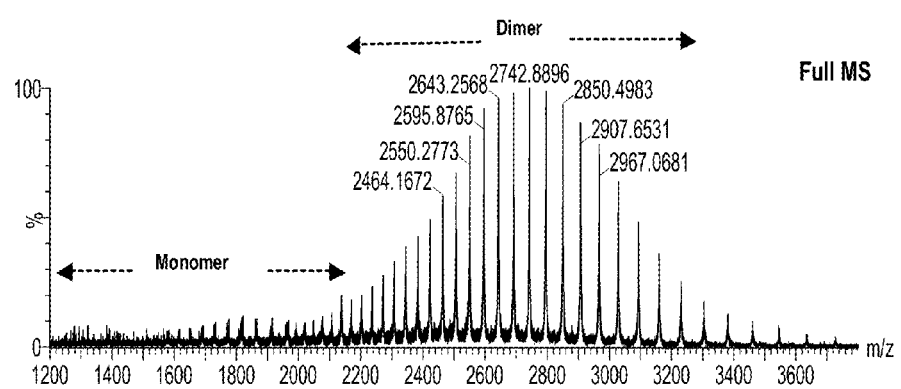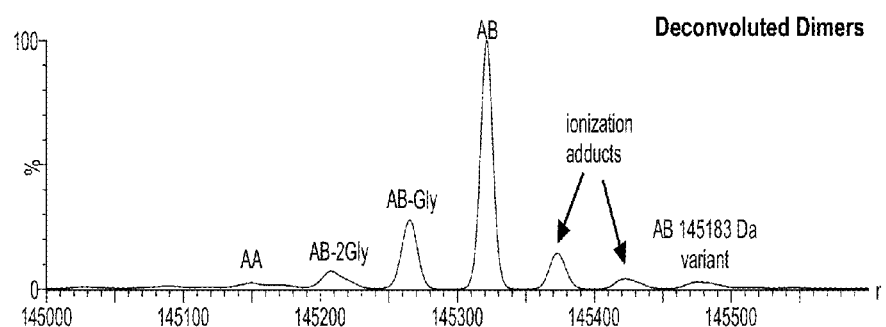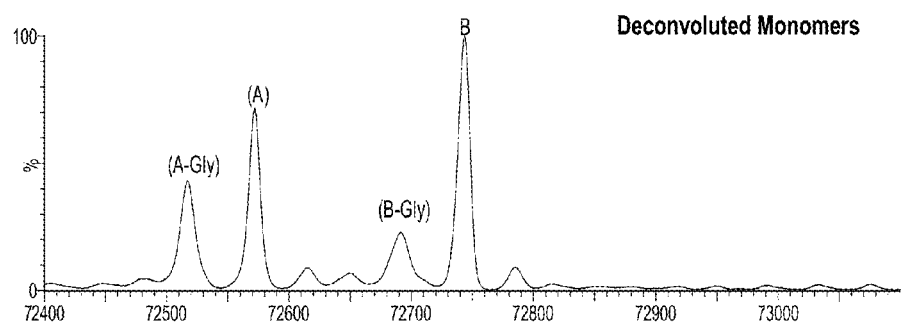
FIG. 9

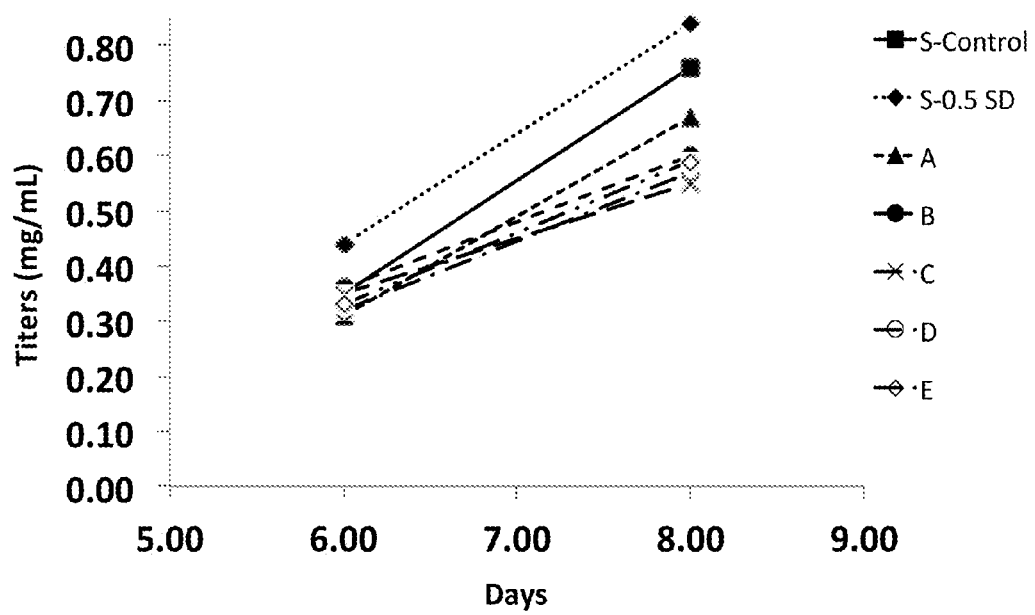

FIG. 14A
Wildtype LC amino acid sequence
DIQMTQSPSSLSASVGDRVTITCRASQDVNTAVAWYQQKPGKAPKLLIYSASFLYSGVPSR
FSGSRSGTDFTLTISSLQPEDFATYYCQQHYTTPPTFGQGTKVEIKRTVAAPSVFIFPPSD
EQLKSGTASVVCLLNNFYPREAKVQWKVDNALQSGNSQESVTEQDSKDSTYSLSSTLTLSK
ADYEKHKVYACEVTHQGLSSPVTKSFNRGEC

FIG. 14B
Wildtype LC nucleotide sequence
GACATCCAGATGACCCAGTCTCCATCCTCCCTGTCTGCATCTGTAGGAGACAGAGTCACCA
TCACTTGCCGGGCAAGTCAGGACGTTAACACCGCTGTAGCTTGGTATCAGCAGAAACCAGG
GAAAGCCCCTAAGCTCCTGATCTATTCTGCATCCTTTTTGTACAGTGGGGTCCCATCAAGG
TTCAGTGGCAGTCGATCTGGGACAGATTTCACTCTCACCATCAGCAGTCTGCAACCTGAAG
ATTTTGCAACTTACTACTGTCAACAGCATTACACTACCCCACCCACTTTCGGCCAAGGGAC
CAAAGTGGAGATCAAACGAACTGTGGCTGCACCATCTGTCTTCATCTTCCCGCCATCTGAT
GAGCAGTTGAAATCTGGAACTGCCTCTGTTGTGTGCCTGCTGAATAACTTCTATCCCAGAG
AGGCCAAAGTACAGTGGAAGGTGGATAACGCCCTCCAATCGGGTAACTCCCAAGAGAGTGT
CACAGAGCAGGACAGCAAGGACAGCACCTACAGCCTCAGCAGCACCCTGACGCTGAGCAAA
GCAGACTACGAGAAACACAAAGTCTACGCCTGCGAAGTCACCCATCAGGGCCTGAGCTCGC
CCGTCACAAAGAGCTTCAACAGGGGAGAGTGTTGA

FIG. 15A
Wildtype HC amino acid sequence
EVQLVESGGGLVQPGGSLRLSCAASGFNIKDTYIHWVRQAPGKGLEWVARIYPTNGYTRYA
DSVKGRFTISADTSKNTAYLQMNSLRAEDTAVYYCSRWGGDGFYAMDYWGQGTLVTVSSAS
TKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNVFS
CSVMHEALHNHYTQKSLSLSPGK

FIG. 15B

Wildtype HC nucleotide sequence
GAGGTGCAGCTGGTGGAAAGCGGAGGAGGACTGGTGCAGCCAGGAGGATCTCTGCGACTGA
GTTGCGCCGCTTCAGGATTCAACATCAAGGACACCTACATTCACTGGGTGCGACAGGCTCC
AGGAAAAGGACTGGAGTGGGTGGCTCGAATCTATCCCACTAATGGATACACCCGGTATGCC
GACTCCGTGAAGGGGAGGTTTACTATTAGCGCCGATACATCCAAAAACACTGCTTACCTGC
AGATGAACAGCCTGCGAGCCGAAGATACCGCTGTGTACTATTGCAGTCGATGGGGAGGAGA
CGGATTCTACGCTATGGATTATTGGGGACAGGGGACCCTGGTGACAGTGAGCTCCGCCTCT
ACCAAGGGCCCCAGTGTGTTTCCCCTGGCTCCTTCTAGTAAATCCACCTCTGGAGGGACAG
CCGCTCTGGGATGTCTGGTGAAGGACTATTTCCCCGAGCCTGTGACCGTGAGTTGGAACTC
AGGCGCCCTGACAAGCGGAGTGCACACTTTTCCTGCTGTGCTGCAGTCAAGCGGGCTGTAC
TCCCTGTCCTCTGTGGTGACAGTGCCAAGTTCAAGCCTGGGCACACAGACTTATATCTGCA
ACGTGAATCATAAGCCCTCAAATACAAAAGTGGACAAGAAAGTGGAGCCCAAGAGCTGTGA
TAAGACCCACACCTGCCCTCCCTGTCCAGCTCCAGAACTGCTGGGAGGACCTAGCGTGTTC
CTGTTTCCCCCTAAGCCAAAAGACACTCTGATGATTTCCAGGACTCCCGAGGTGACCTGCG
TGGTGGTGGACGTGTCTCACGAGGACCCCGAAGTGAAGTTCAACTGGTACGTGGATGGCGT
GGAAGTGCATAATGCTAAGACAAAACCAAGAGAGGAACAGTACAACTCCACTTATCGCGTC
GTGAGCGTGCTGACCGTGCTGCACCAGGACTGGCTGAACGGGAAGGAGTATAAGTGCAAAG
TCAGTAATAAGGCCCTGCCTGCTCCAATCGAAAAAACCATCTCTAAGGCCAAAGGCCAGCC
AAGGGAGCCCCAGGTGTACACACTGCCACCCAGCAGAGACGAACTGACCAAGAACCAGGTG
TCCCTGACATGTCTGGTGAAAGGCTTCTATCCTAGTGATATTGCTGTGGAGTGGGAATCAA
ATGGACAGCCAGAGAACAATTACAAGACCACACCTCCAGTGCTGGACAGCGATGGCAGCTT
CTTCCTGTATTCCAAGCTGACAGTGGATAAATCTCGATGGCAGCAGGGGAACGTGTTTAGT
TGTTCAGTGATGCATGAAGCCCTGCACAATCATTACACTCAGAAGAGCCTGTCCCTGTCTC
CCGGCAAATGA

FIG. 16A

Fc amino acid sequence: Chain A
EPKSSDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTIS
KAKGQPREPQVYVYPPSRDELTKNQVSLTCLVKGFYPSDIAVEWESNGQPENNYKTTPPVL
DSDGSFALVSKLTVDKSRWQQGNVFSCSVMHEALHNHYTQKSLSLSPGK

FIG. 16B
Fc nucleic acid sequence: Chain A
GAATTCGCCACCATGGCCGTGATGGCACCTAGAACCCTGGTCCTGCTGCTGAGCGGGGCAC
TGGCACTGACACAGACTTGGGCTGGGGAACCTAAGAGCAGCGACAAGACTCACACCTGCCC
ACCTTGTCCAGCACCAGAACTGCTGGGAGGACCAAGCGTGTTCCTGTTTCCACCCAAGCCC
AAAGATACCCTGATGATCAGCCGAACACCCGAAGTGACTTGCGTGGTCGTGGACGTGTCCC
ACGAGGACCCCGAAGTCAAGTTCAACTGGTACGTGGACGGCGTCGAAGTGCATAATGCTAA
GACAAAACCACGGGAGGAACAGTACAACTCTACTTATAGAGTCGTGAGTGTCCTGACCGTG
CTGCATCAGGATTGGCTGAACGGCAAGAGTATAAGTGCAAAGTGTCTAATAAGGCCCTGC
CTGCTCCAATCGAGAAAACCATTAGTAAGGCTAAAGGGCAGCCCAGGGAACCTCAGGTCTA
CGTGTATCCTCCAAGTCGCGACGAGCTGACCAAGAACCAGGTCTCACTGACATGTCTGGTG
AAAGGATTTTACCCTTCCGATATTGCAGTGGAGTGGGAATCTAATGGCCAGCCAGAGAACA
ATTATAAGACCACACCCCCTGTGCTGGACAGCGATGGGTCCTTCGCACTGGTCTCAAAGCT
GACAGTGGACAAAAGCAGATGGCAGCAGGGAAACGTCTTTAGCTGTTCCGTGATGCACGAA
GCCCTGCACAATCATTACACTCAGAAGTCTCTGAGTCTGTCACCTGGCAAATGAGGATCC

FIG. 16C
Fc amino acid sequence: Chain B
EPKSSDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTIS
KAKGQPREPQVYVLPPSRDELTKNQVSLLCLVKGFYPSDIAVEWESNGQPENNYLTWPPVL
DSDGSFFLYSKLTVDKSRWQQGNVFSCSVMHEALHNHYTQKSLSLSPGK*GS

FIG. 16D

Fc nucleic acid sequence: Chain B
GAATTCGCCACCATGGCTGTGATGGCTCCACGCACCCTGGTCCTGCTGCTGTCCGGGGCAC
TGGCACTGACTCAGACTTGGGCTGGGGAACCTAAAAGCAGCGACAAGACCCACACATGCCC
CCCTTGTCCAGCTCCAGAACTGCTGGGAGGACCAAGCGTGTTCCTGTTTCCACCCAAGCCC
AAAGATACACTGATGATCAGCCGAACTCCCGAGGTCACCTGCGTGGTCGTGGACGTGTCCC
ACGAGGACCCCGAAGTCAAGTTCAACTGGTACGTGGACGGCGTCGAAGTGCATAATGCAAA
GACTAAACCACGGGAGGAACAGTACAACTCTACATATAGAGTCGTGAGTGTCCTGACTGTG
CTGCATCAGGATTGGCTGAACGGCAAGAGTATAAGTGCAAAGTGTCTAATAAGGCCCTGC
CTGCTCCAATCGAGAAAACTATTAGTAAGGCAAAAGGGCAGCCCAGGGAACCTCAGGTCTA
CGTGCTGCCTCCAAGTCGCGACGAGCTGACCAAGAACCAGGTCTCACTGCTGTGTCTGGTG
AAAGGATTCTATCCTTCCGATATTGCCGTGGAGTGGGAATCTAATGGCCAGCCAGAGAACA
ATTACCTGACCTGGCCCCCTGTGCTGGACAGCGATGGGTCCTTCTTTCTGTATTCAAAGCT
GACAGTGGACAAAAGCAGATGGCAGCAGGGAAACGTCTTTAGCTGTTCCGTGATGCACGAA
GCCCTGCACAATCATTACACCCAGAAGTCTCTGAGTCTGTCACCTGGCAAATGAGGATCC

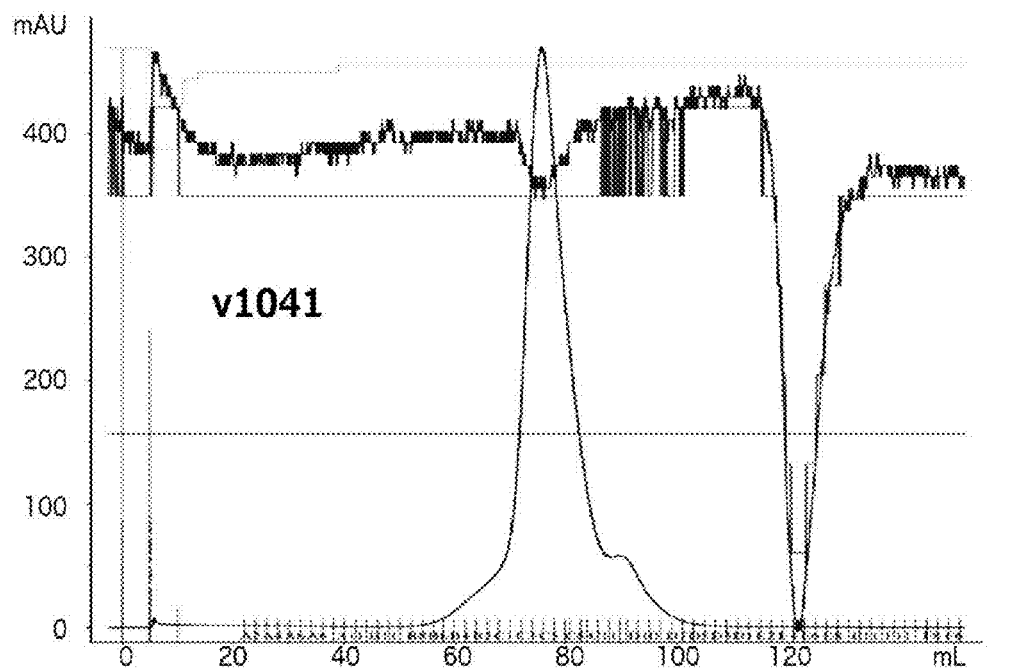
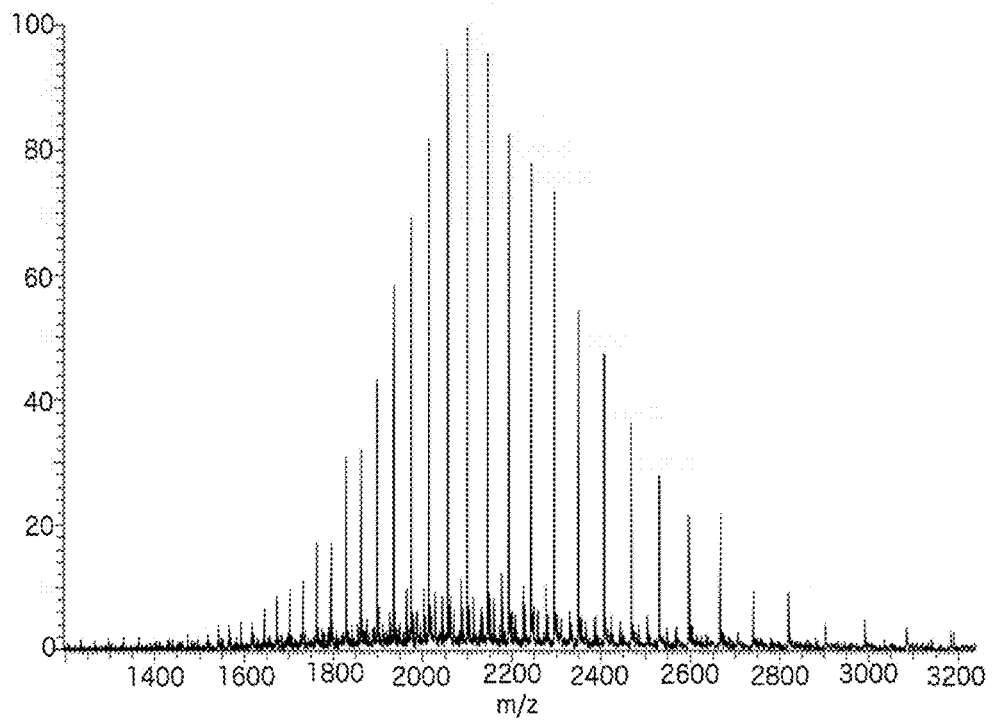
FIG. 17B Cont.

Figure 18A
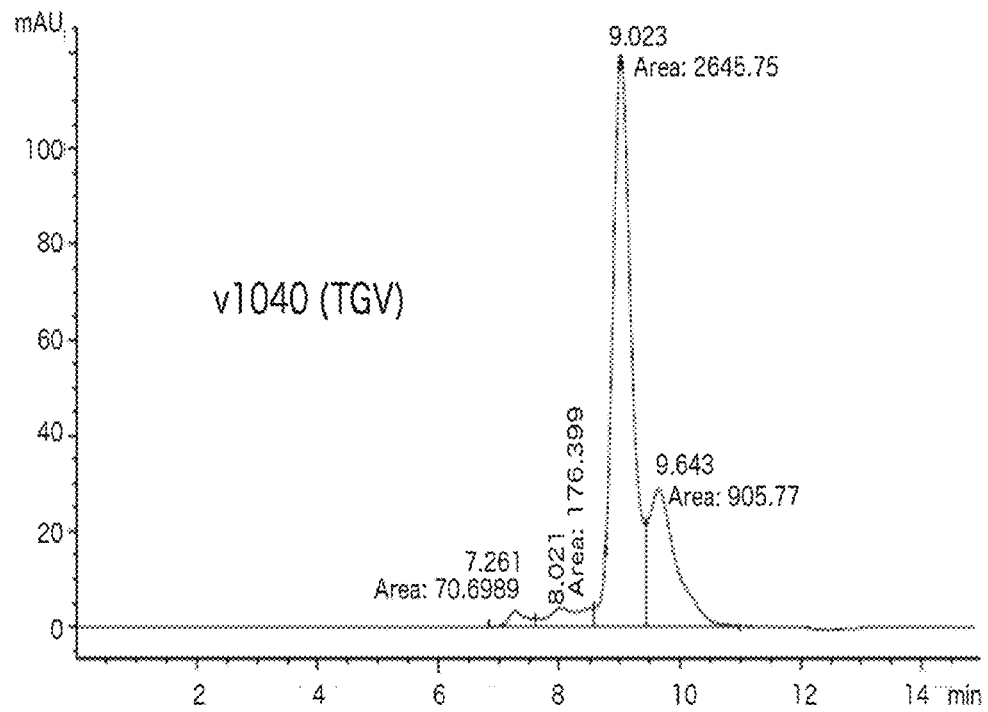
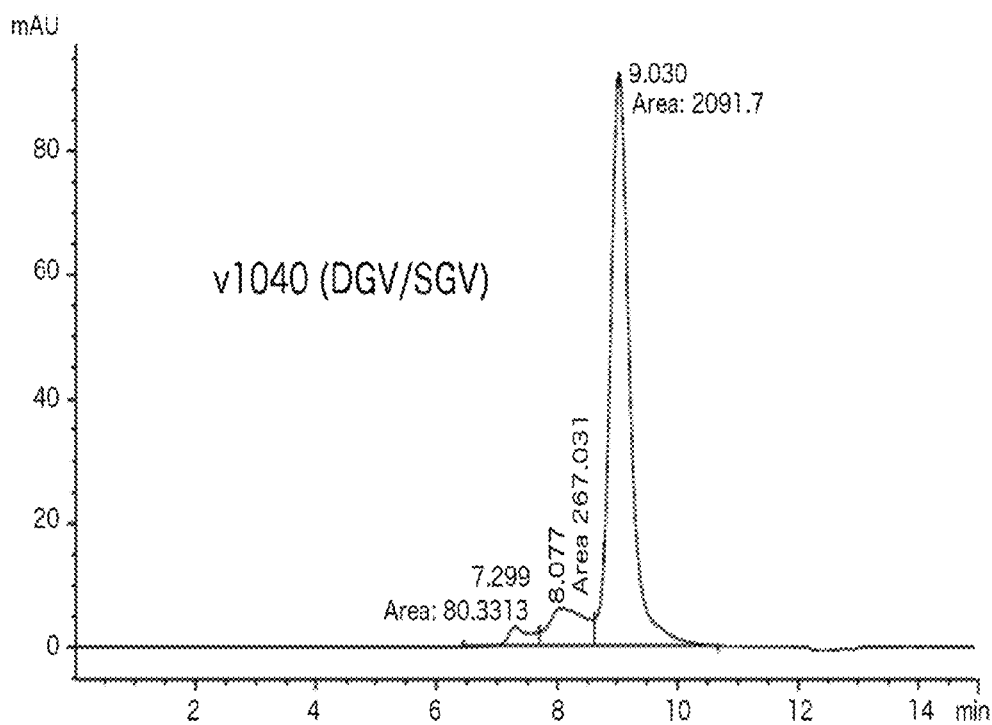

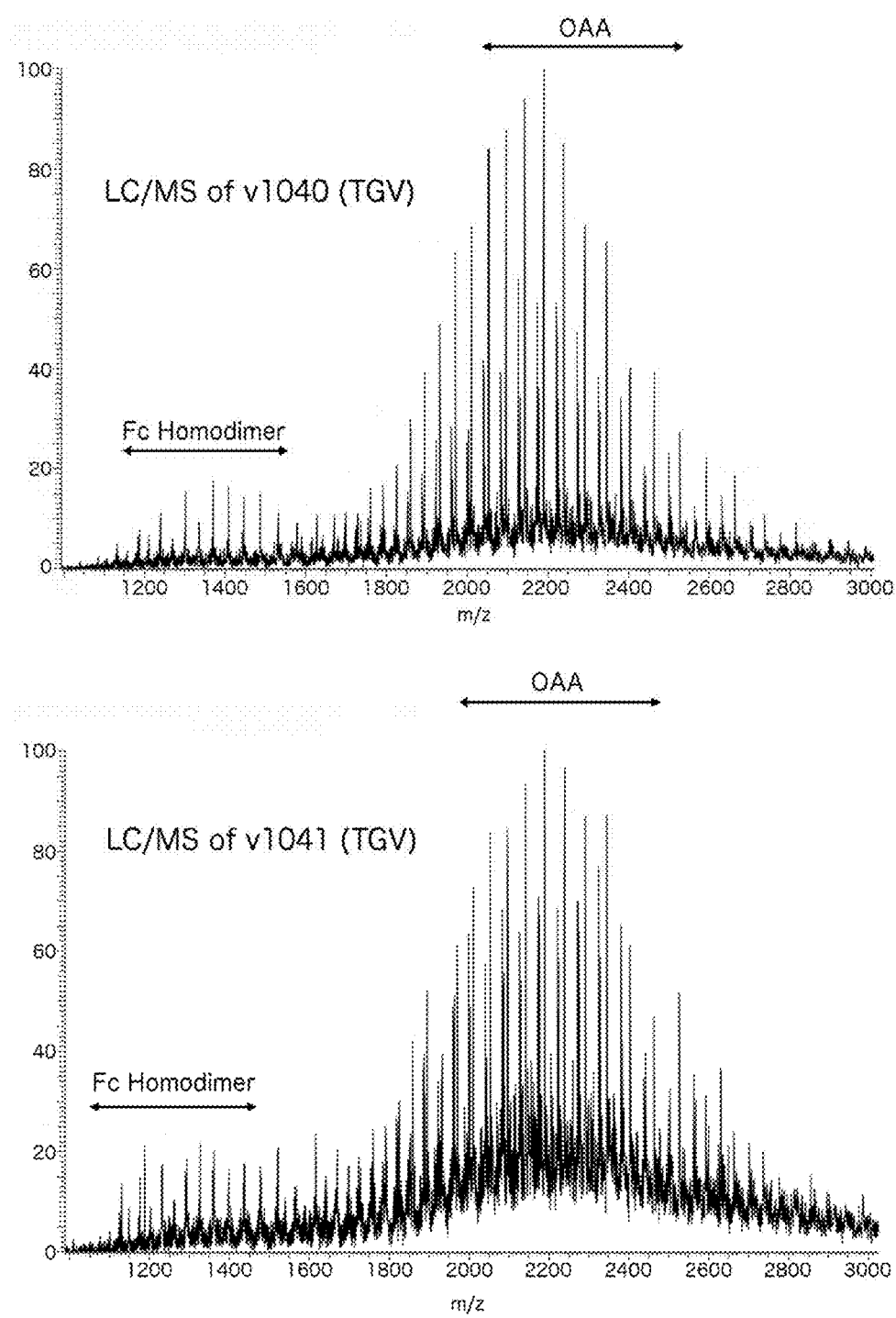

FIG. 20A
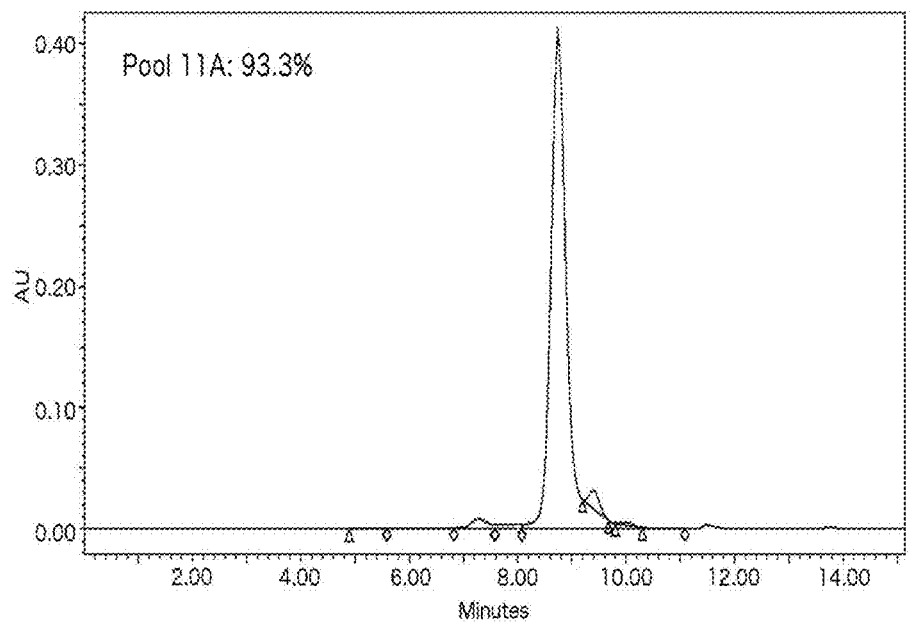
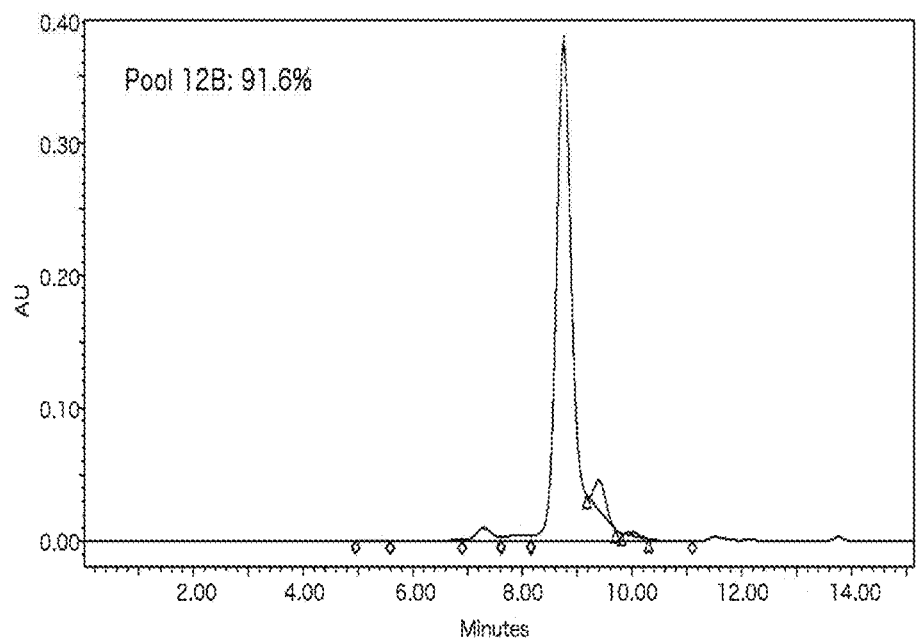

FIG. 20A Cont.
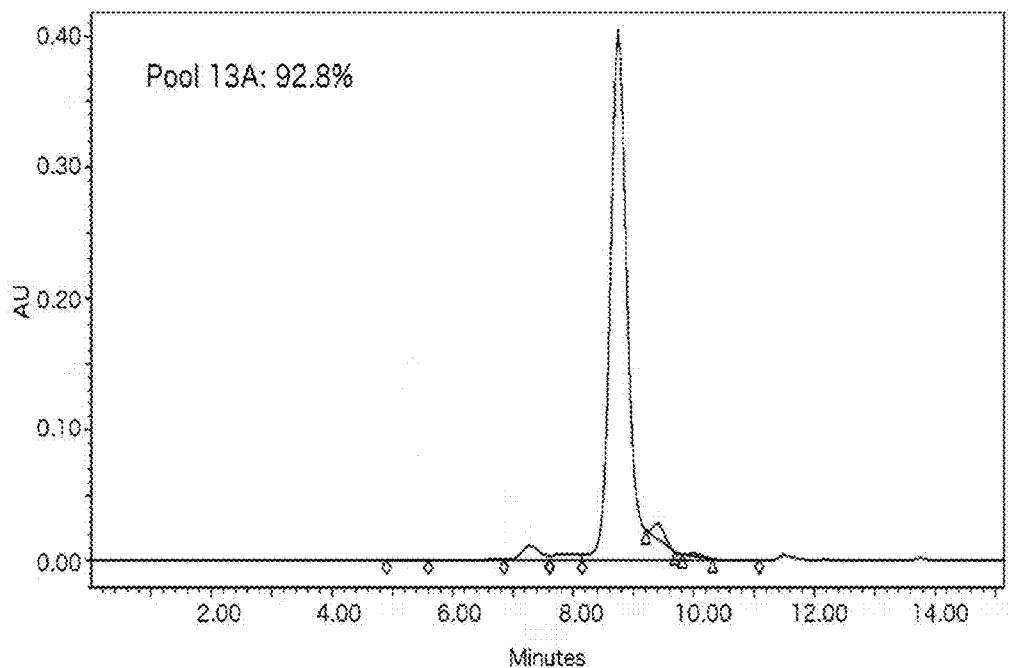
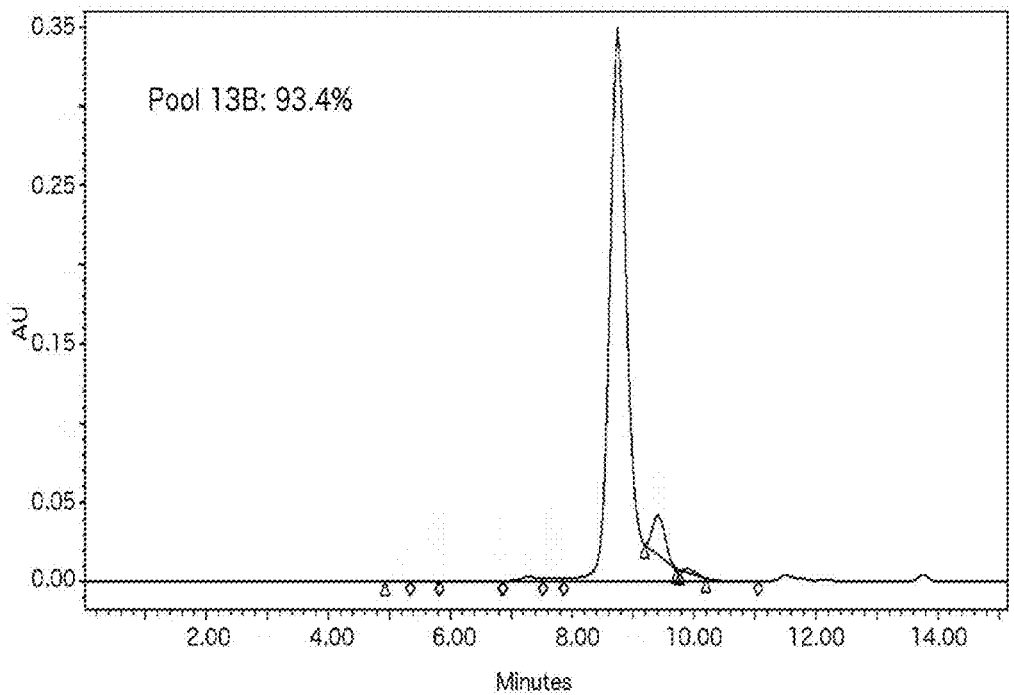

FIG. 20B
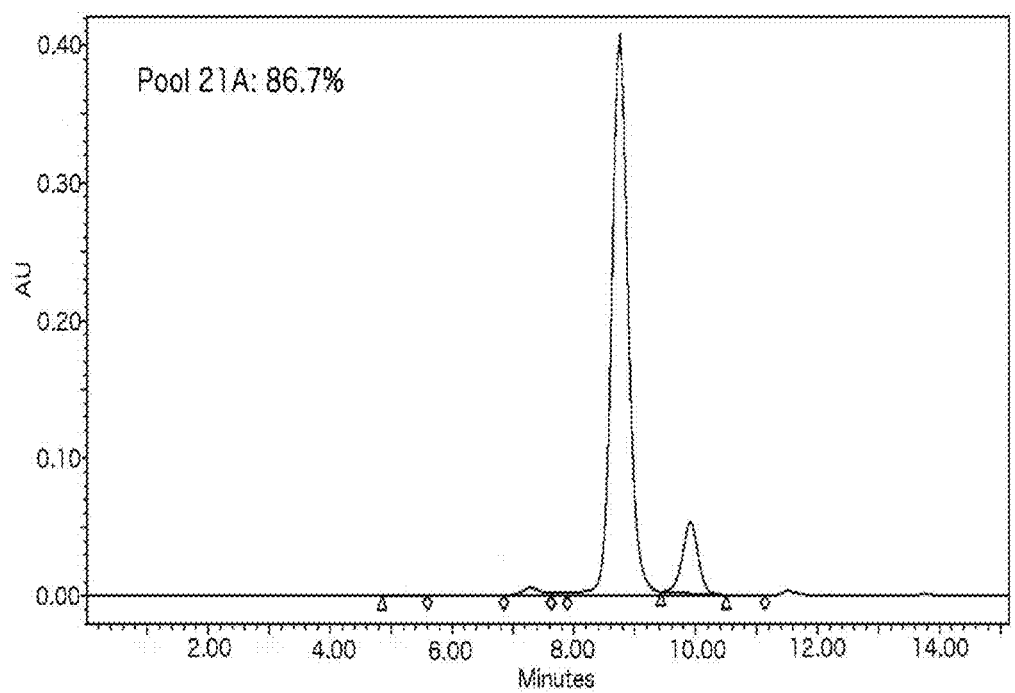
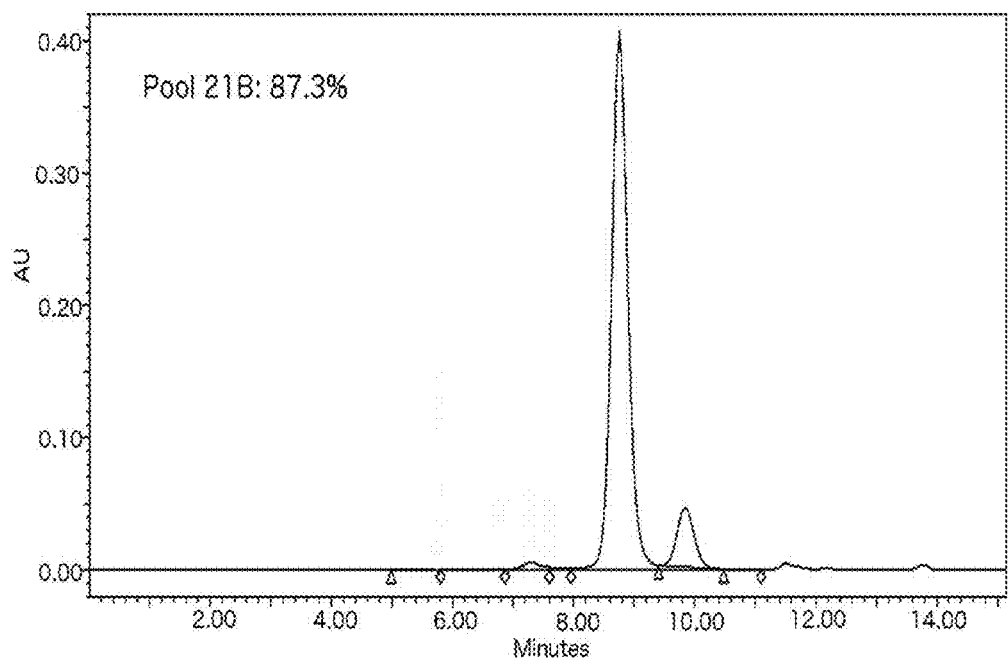

FIG. 20B Cont.
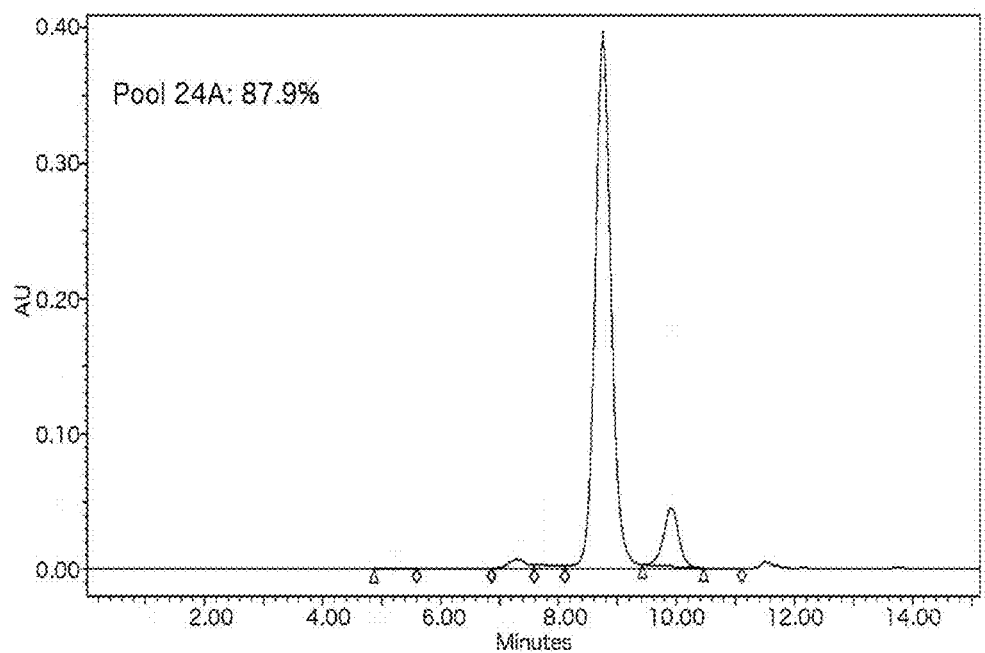
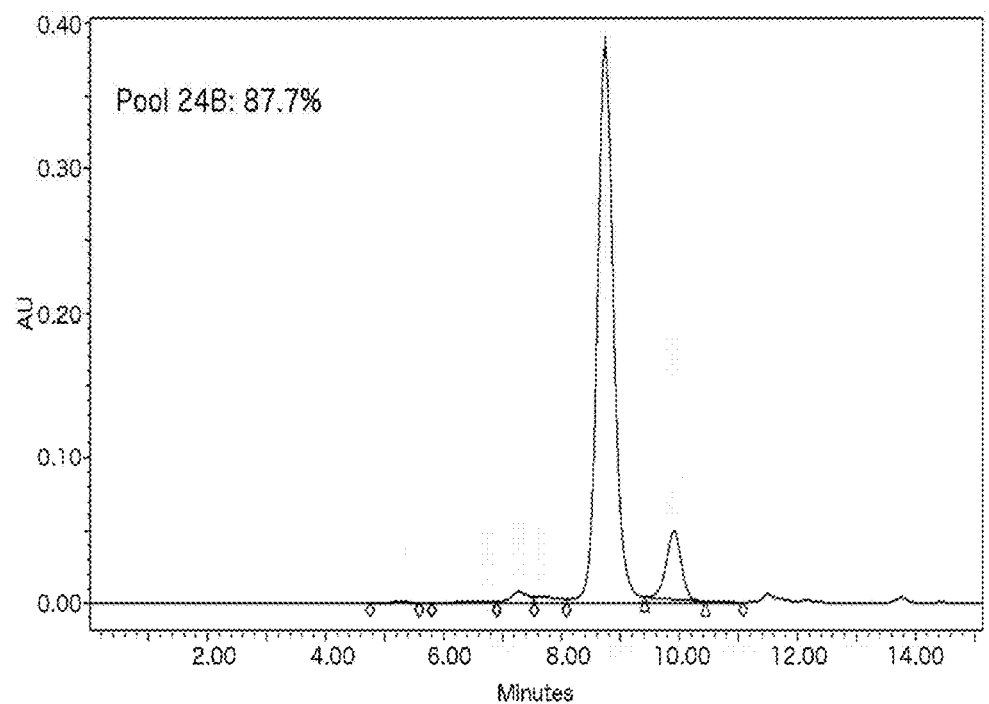

SEQUENCE LISTING

```
<160> NUMBER OF SEQ ID NOS: 8

<210> SEQ ID NO 1
<211> LENGTH: 214
<212> TYPE: PRT
<213> ORGANISM: Homo sapiens

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80
```

Glu Asp Phe Ala Thr Tyr Tyr Cys Gln Gln His Tyr Thr Pro Pro
                    85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 2
<211> LENGTH: 645
<212> TYPE: DNA
<213> ORGANISM: Homo sapiens

<400> SEQUENCE: 2
gacatccaga tgacccagtc tccatcctcc ctgtctgcat ctgtaggaga cagagtcacc    60
atcacttgcc gggcaagtca ggacgttaac accgctgtag cttggtatca gcagaaacca   120
gggaaagccc ctaagctcct gatctattct gcatcctttt tgtacagtgg ggtcccatca   180
aggttcagtg gcagtcgatc tgggacagat ttcactctca ccatcagcag tctgcaacct   240
gaagattttg caacttacta ctgtcaacag cattacacta ccccacccac tttcggccaa   300
gggaccaaag tggagatcaa acgaactgtg gctgcaccat ctgtcttcat cttccgcca   360 tctgatgagc agttgaaatc tggaactgcc tctgttgtgt gcctgctgaa taacttctat   420
cccagagagg ccaaagtaca gtggaaggtg gataacgccc tccaatcggg taactcccaa   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gttga                   645

<210> SEQ ID NO 3
<211> LENGTH: 450
<212> TYPE: PRT
<213> ORGANISM: Homo sapiens

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr

```
            65                  70                  75                  80
Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 4
<211> LENGTH: 1353
<212> TYPE: DNA
<213> ORGANISM: Homo sapiens
```

<400> SEQUENCE: 4

```
gaggtgcagc tggtggaaag cggaggagga ctggtgcagc caggaggatc tctgcgactg        60
agttgcgccg cttcaggatt caacatcaag gacacctaca ttcactgggt gcgacaggct       120
ccaggaaaag gactggagtg ggtggctcga atctatccca ctaatggata cacccggtat       180
gccgactccg tgaaggggag gtttactatt agcgccgata catccaaaaa cactgcttac       240
ctgcagatga acagcctgcg agccgaagat accgctgtgt actattgcag tcgatgggga       300
ggagacggat tctacgctat ggattattgg ggacagggga ccctggtgac agtgagctcc       360
gcctctacca agggccccag tgtgtttccc ctggctcctt ctagtaaatc cacctctgga       420
gggacagccg ctctgggatg tctggtgaag gactatttcc ccgagcctgt gaccgtgagt       480
tggaactcag gcgccctgac aagcggagtg cacacttttc ctgctgtgct gcagtcaagc       540
gggctgtact ccctgtcctc tgtggtgaca gtgccaagtt caagcctggg cacacagact       600
tatatctgca acgtgaatca taagccctca aatacaaaag tggacaagaa agtggagccc       660
aagagctgtg ataagaccca cacctgccct ccctgtccag ctccagaact gctgggagga       720
cctagcgtgt tcctgtttcc ccctaagcca aaagacactc tgatgatttc caggactccc       780
gaggtgacct gcgtggtggt ggacgtgtct cacgaggacc ccgaagtgaa gttcaactgg       840
tacgtggatg gcgtggaagt gcataatgct aagacaaaac aagagagga cagtacaaac       900
tccacttatc gcgtcgtgag cgtgctgacc gtgctgcacc aggactggct gaacgggaag       960
gagtataagt gcaaagtcag taataaggcc ctgcctgctc aatcgaaaaa aaccatctct      1020
aaggccaaag gccagccaag ggagccccag gtgtacacac tgccacccag cagagacgaa      1080
ctgaccaaga accaggtgtc cctgacatgt ctggtgaaag gcttctatcc tagtgatatt      1140
gctgtggagt gggaatcaaa tggacagcca gagaacaatt acaagaccac acctccagtg      1200
ctggacagcg atggcagctt cttcctgtat tccaagctga cagtggataa atctcgatgg      1260
cagcagggga acgtgtttag ttgttcagtg atgcatgaag ccctgcacaa tcattacact      1320
cagaagagcc tgtccctgtc tcccggcaaa tga                                   1353
```

<210> SEQ ID NO 5
<211> LENGTH: 232
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
```

```
               100                 105                 110
Leu Pro Ala Pro Ile Glu Lys Thr Ile Ser Lys Ala Lys Gly Gln Pro
            115                 120                 125

Arg Glu Pro Gln Val Tyr Val Tyr Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Ala Leu Val
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 6
<211> LENGTH: 792
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
gaattcgcca ccatggccgt gatggcacct agaaccctgg tcctgctgct gagcggggca      60
ctggcactga cacagacttg ggctggggaa cctaagagca gcgacaagac tcacacctgc     120
ccaccttgtc agcaccagaa actgctggga ggaccaagcg tgttcctgtt ccacccaag     180 cccaaagata ccctgatgat cagccgaaca cccgaagtga cttgcgtggt cgtggacgtg    240
tcccacgagg accccgaagt caagttcaac tggtacgtgg acggcgtcga agtgcataat     300
gctaagacaa accacgggaa ggaacagtac aactctactt atagagtcgt gagtgtcctg     360
accgtgctgc atcaggattg gctgaacggc aaagagtata agtgcaaagt gtctaataag     420
gccctgcctg ctccaatcga gaaaaccatt agtaaggcta agggcagcc cagggaacct      480 caggtctacg tgtatcctcc aagtcgcgac gagctgacca gaaccaggt ctcactgaca       540 tgtctggtga aggatttta cccttccgat attgcagtgg agtgggaatc taatggccag      600
ccagagaaca attataagac cacacccct gtgctggaca gcgatgggtc cttcgcactg      660
gtctcaaagc tgacagtgga caaaagcaga tggcagcagg gaaacgtctt agctgttcc      720 gtgatgcacg aagccctgca caatcattac actcagaagt ctctgagtct gtcacctggc     780
aaatgaggat cc                                                         792

<210> SEQ ID NO 7
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Pro Lys Ser Ser Asp Lys Thr His Thr Cys Pro Pro Cys Pro Ala
1               5                   10                  15
```

Pro Glu Leu Leu Gly Gly Pro Ser Val Phe Leu Phe Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Val Leu Pro Pro Ser Arg Asp Glu Leu Thr
    130                 135                 140

Lys Asn Gln Val Ser Leu Leu Cys Leu Val Lys Gly Phe Tyr Pro Ser
145                 150                 155                 160

Asp Ile Ala Val Glu Trp Ser Asn Gly Gln Pro Glu Asn Asn Tyr
                165                 170                 175

Leu Thr Trp Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 8
<211> LENGTH: 792
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
gaattcgcca ccatggctgt gatggctcca cgcaccctgg tcctgctgct gtccggggca      60
ctggcactga ctcagacttg ggctggggaa cctaaaagca gcgacaagac ccacacatgc     120 ccccttgtc cagctccaga actgctggga ggaccaagcg tgttcctgtt ccacccaag      180 cccaaagata cactgatgat cagccgaact cccgaggtca cctgcgtggt cgtggacgtg    240
tcccacgagg accccgaagt caagttcaac tggtacgtgg acggcgtcga agtgcataat    300
gcaaagacta aaccacggga ggaacagtac aactctacat atagagtcgt gagtgtcctg    360
actgtgctgc atcaggattg gctgaacggc aaagagtata gtgcaaagt gtctaataag    420 gccctgcctg ctccaatcga gaaaactatt agtaaggcaa aaggcagcc cagggaacct    480 caggtctacg tgctgcctcc aagtcgcgac gagctgacca agaaccaggt ctcactgctg    540
tgtctggtga aaggattcta tccttccgat attgccgtgg agtgggaatc taatggccag    600
ccagagaaca attacctgac ctggccccct gtgctggaca gcgatgggtc cttctttctg    660

```
tattcaaagc tgacagtgga caaaagcaga tggcagcagg gaaacgtctt tagctgttcc    720
gtgatgcacg aagccctgca caatcattac acccagaagt ctctgagtct gtcacctggc    780
aaatgaggat cc                                                        792
```

PROCESS AND METHODS FOR EFFICIENT MANUFACTURING OF HIGHLY PURE ASYMMETRIC ANTIBODIES IN MAMMALIAN CELLS

1.1 CROSS REFERENCE TO RELATED APPLICATIONS

This application is a continuation of U.S. application Ser. No. 13/927,065, filed Jun. 25, 2013, which claims the benefit under 35 U.S.C. §119(e) of U.S. Provisional Patent Application No. 61/664,102, filed Jun. 25, 2012, which are herein incorporated by reference in its entirety.

1.2 FIELD OF THE INVENTION

The present invention relates to the field of therapeutic antibodies, in particular to a highly efficient and rapid process for the generation of mammalian cell lines expressing a high titre and purity of an asymmetric antibody as well as a method of producing and purifying therapeutic antibodies for pre-clinical and clinical use.

1.3 BACKGROUND

Heterodimeric polypeptides have been designed by engineering the CH3 domain in the Fc region of an antibody (for instance: Ridgway et. al. Protein Engineering 1996, 9, 617-621; U.S. Pat. No. 5,731,168; U.S. Pat. No. 5,821,333; U.S. Pat. No. 5,807,706; U.S. Pat. No. 7,183,076; U.S. Pat. No. 7,642,228; U.S. Pat. No. 7,695,936; US20100286374; US20070287170 and US20120149876). This method has been used to design bi-specific antibodies, and express non-glycosylated forms of such antibodies from non-mammalian cell lines such as *E. coli* (see, for instance, Merchant et. al. Nat. Biotechnol. 1998; 16; 677-681, or Jin et al. Cancer Res 2008; 68; 4360-4368). Typically, screening for a stable cell culture expressing the pure or homogeneous product molecule in the heterodimeric form without contaminant homodimers is challenging. The heterodimeric product of interest is co-expressed in the cell with contaminant homodimers and monomers and it is challenging to obtain the pure heterodimeric species (see for example, US Patent Publication No. 20090232811).

Large scale expression of these engineered Fc heterodimers and bi-specific antibodies comprising the same in mammalian cell lines, has been hindered by the unreliable and variable purity of the heterodimer obtained (see for instance Jackman et. al. J. Bioi. Chem. 2010, 285, 20850-20859). Among other approaches, currently, an *E. coli* based expression strategy is used for large-scale expression. Alternately, two heavy chains of the asymmetric antibody are expressed as separate heavy-light chain fragments in two different cell lines. The two purified fragments are then annealed in a one-to-one ratio. A similar procedure for producing asymmetric antibodies by mixing two different antibodies is utilized by Schuurman et. al. (US201 001 05874A1). This is a multistep process and leads to high cost of goods.

Some methods of co-expression of the heavy chains of a symmetric antibody in *E. coli* have been developed (for instance Cabilly et. al: U.S. Pat. No. 4,816,567; U.S. Pat. No. 6,331,415; U.S. Pat. No. 7,923,221). However, these methods are not developed for expression of asymmetric antibodies, and the process of expression in *E. coli* results in an aglycosylated antibody Fc which has characteristics that are very different from the intrinsic characteristics of the wild type antibody which is glycosylated. Accordingly, the large scale production of asymmetric antibody has been limited and it has been difficult to achieve high purity and yield in stable mammalian cell lines.

2. SUMMARY OF THE INVENTION

Provided herein is a process and methods for efficient manufacturing of highly pure asymmetric antibodies in mammalian cells. In accordance with an aspect of the invention, there is provided a method of producing an expression product containing an asymmetric antibody product comprising a first heavy chain polypeptide, a second heavy chain polypeptide, and at least one light chain polypeptide in stable mammalian cells, the method comprising: transfecting at least one mammalian cell with: i) a first DNA sequence encoding the first heavy chain polypeptide, wherein the first heavy chain polypeptide comprises a variant CH3 sequence; ii) a second DNA sequence encoding the second heavy chain polypeptide, wherein the second heavy chain polypeptide comprises a variant CH3 sequence different from the first heavy chain polypeptide, and wherein: a) the variant CH3 sequences of the first and second heavy chain polypeptides promote the formation of a heterodimeric Fc region with a CH3 domain having a Tm greater than 75° C.; and b) the first and second heavy chain polypeptides preferentially exist as monomers rather than homodimers when not in the form of a heterodimer pair; and iii) at least one DNA sequence encoding a light chain polypeptide; such that said first DNA sequence, said second DNA sequence and said at least one DNA sequence encoding a light chain polypeptide are transfected in said at least one mammalian cell in a pre-determined ratio to generate stable mammalian cells; culturing said stable mammalian cells to produce an expression product comprising greater than 75% asymmetric antibody product, less than 10% monomers, and undetectable amounts of homodimers of said first or second heavy chain polypeptide.

In accordance with another aspect described herein is provided a method of producing an expression product containing an asymmetric antibody product comprising at least a first heavy chain polypeptide and at least a second heavy chain polypeptide in stable mammalian cells, the method comprising: a. transfecting at least one mammalian cell with: i) a first DNA sequence encoding the first heavy chain polypeptide, wherein the first heavy chain polypeptide comprises a variant CH3 sequence; and ii) a second DNA sequence encoding at least the second heavy chain polypeptide, wherein the second heavy chain polypeptide comprises a variant CH3 sequence different from the first heavy chain polypeptide, and wherein: a) the variant CH3 sequences of the first and second heavy chain polypeptides promote the formation of a heterodimeric Fc region with a Tm greater than 75° C.; b) the first and second heavy chain polypeptides preferentially exist as monomers rather than homodimers while not in the form of heterodimeric pair; and such that said first DNA sequence and said second DNA sequence are transfected in said at least one mammalian cell in a pre-determined ratio to generate stable mammalian cells; and b. culturing said stable mammalian cells to produce an expression product comprising greater than 75% asymmetric antibody product, less than 10% monomers, and undetectable amounts of homodimers of said first or second heavy chain polypeptide.

In accordance with another aspect described herein is provided a expression product produced by the method according to the invention.

In accordance with another aspect described herein is provided a purified asymmetric antibody product produced by the method according to the invention.

In accordance with another aspect of the invention there is provided a set of expression vectors comprising a first DNA sequence encoding a first heavy chain polypeptide, wherein the first heavy chain polypeptide comprises a variant CH3 sequence, and a second DNA sequence encoding the second heavy chain polypeptide, wherein the second heavy chain polypeptide comprises a variant CH3 sequence different from the first heavy chain polypeptide, and wherein: a) the variant CH3 sequences of the first and second heavy chain polypeptides promote the formation of a heterodimeric Fc region comprising a CH3 domain with a Tm greater than 75° C.; and b) the first and second heavy chain polypeptides preferentially exist as monomers rather than homodimers when not in the heterodimeric form.

In accordance with another aspect of the invention there is provided a multi-cistronic expression vector comprising i) a first DNA sequence encoding a first heavy chain polypeptide, wherein the first heavy chain polypeptide comprises a variant CH3 sequence; ii) a second DNA sequence encoding the second heavy chain polypeptide, wherein the second heavy chain polypeptide comprises a variant CH3 sequence different from the first heavy chain polypeptide, and wherein: a) the variant CH3 sequences of the first and second heavy chain polypeptides promote the formation of a heterodimeric Fc region comprising a CH3 domain with a Tm greater than 75° C.; b) the first and second heavy chain polypeptides preferentially exist as monomers rather than homodimers when not in the heterodimeric form; and iii) at least one DNA sequence encoding a light chain polypeptide.

In accordance with another aspect of the invention there is provided a stable mammalian cell line comprising an expression vector according to the invention.

In accordance with another aspect of the invention there is provided a stable mammalian cell producing an asymmetric antibody product according to the method of the invention.

In accordance with another aspect of the invention there is provided a mammalian cell producing an expression product containing an asymmetric antibody product comprising a first heavy chain polypeptide, a second heavy chain polypeptide, and at least one light chain polypeptide, said mammalian cell comprising i) a first DNA sequence encoding the first heavy chain polypeptide, wherein the first heavy chain polypeptide comprises a variant CH3 sequence; ii) a second DNA sequence encoding the second heavy chain polypeptide, wherein the second heavy chain polypeptide comprises a variant CH3 sequence different from the first heavy chain polypeptide, and wherein: a) the variant CH3 sequences of the first and second heavy chain polypeptides promote the formation of a heterodimeric Fc region comprising a CH3 domain with a Tm greater than 75° C.; b) the first and second heavy chain polypeptides preferentially exist as monomers rather than homodimers when not in the heterodimeric form; and iii) at least one DNA sequence encoding a light chain polypeptide; wherein the first DNA sequence, the second DNA sequence, and the at least one DNA sequence encoding a light chain polypeptide are transfected in the mammalian cell in a pre-determined ratio, and wherein the expression product comprises greater than 75% asymmetric antibody product, less than 10% monomers, and undetectable amounts of homodimers of said first or second heavy chain polypeptide.

In accordance with another aspect of the invention there is provided a mammalian cell producing an expression product containing an asymmetric antibody product comprising at least a first heavy chain polypeptide and at least a second heavy chain polypeptide in mammalian cells, said mammalian cell comprising: i) a first DNA sequence encoding the first heavy chain polypeptide, wherein the first heavy chain polypeptide comprises a variant CH3 sequence; and ii) a second DNA sequence encoding at least the second heavy chain polypeptide, wherein the second heavy chain polypeptide comprises a variant CH3 sequence different from the first heavy chain polypeptide, and wherein: a) the variant CH3 sequences of the first and second heavy chain polypeptides promote the formation of a heterodimeric Fc region comprising a CH3 domain with a Tm greater than 75° C.; b) the first and second heavy chain polypeptides preferentially exist as monomers rather than homodimers when not in the heterodimeric form; and wherein the first and second DNA sequences are transfected in the mammalian cell in a pre-determined ratio, and wherein the expression product comprises greater than 75% asymmetric antibody product, less than 10% monomers, and undetectable amounts of homodimers of said first or second heavy chain polypeptide.

In accordance with another aspect of the invention there is provided a kit for expression of asymmetric antibodies in stable mammalian cell lines comprising a mammalian cell line of the invention and instructions for use thereof.

In accordance with another aspect of the invention there is provided a method of screening monoclonal mammalian cells to identify a cell expressing an asymmetric antibody product with high titer and less than 10% monomer, said method comprising: a. transfecting mammalian cells with different ratios of a first DNA sequence encoding a first heavy chain polypeptide; a second DNA sequence encoding a second heavy chain polypeptide different from the first heavy chain polypeptide; and a third DNA sequence encoding a light chain polypeptide, to generate transfected mammalian cells, b. culturing the transfected mammalian cells to generate an expression product comprising the asymmetric antibody product; c. identifying the transfected monoclonal mammalian cells which generate an expression product comprising the asymmetric antibody product with maximum purity, by i. performing protein A purification on the expression product to isolate the asymmetric antibody product as well as monomeric species; and ii. determining the titer or purity of the asymmetric antibody product and monomers in the expression product, and iii. identifying the transfected monoclonal mammalian cell that generates an expression product with high titer of asymmetric antibody product and less than 10% monomer.

In accordance with another aspect of the invention there is provided a A method of screening monoclonal mammalian cells to identify a cell expressing an asymmetric antibody product with high titer and less than 5% monomer, said method comprising: a. transfecting mammalian cells with different ratios of a first DNA sequence encoding a first heavy chain polypeptide; a second DNA sequence encoding a second heavy chain polypeptide different from the first heavy chain polypeptide; to generate transfected mammalian cells, b. culturing the transfected mammalian cells to generate an expression product comprising the asymmetric antibody product; c. identifying the transfected monoclonal mammalian cells which generate an expression product comprising the asymmetric antibody product with maximum purity, by i. performing protein A purification on the expression product to isolate the asymmetric antibody product as well as monomeric species; and ii. determining the titer or purity of the asymmetric antibody product and monomers in the expression product, and iii. identifying the transfected monoclonal mammalian cell that generates an expression product with high titer of asymmetric antibody product and less than 5% monomer.

In accordance with another aspect of the invention there is provided a method of producing an asymmetric antibody product comprising a first heavy chain polypeptide a second heavy chain polypeptide, and at least one light chain polypeptide in mammalian cells, the method comprising: transiently transfecting at least one mammalian cell pool with: i) a first DNA sequence encoding the first heavy chain polypeptide, wherein the first heavy chain polypeptide comprises a variant CH3 sequence; ii) a second DNA sequence encoding the second heavy chain polypeptide, wherein the second heavy chain polypeptide comprises a variant CH3 sequence different from the first heavy chain polypeptide; and wherein: a) the variant CH3 sequences of the first and second heavy chain polypeptides promote the formation of a heterodimeric Fc region comprising a CH3 domain with a Tm of greater than 75° C.; b) the first and second heavy chain polypeptides preferentially exist as monomers rather than homodimers when not present in the heterodimeric form; and iii) at least one DNA sequence encoding a light chain polypeptide; such that said first DNA sequence, said second DNA sequence and said at least one DNA sequence encoding a light chain polypeptide are transfected in said pool of mammalian cell in a pre-determined ratio to generate a pool of transiently transfected mammalian cells; culturing said transiently transfected pool of mammalian cells to produce an expression product comprising greater than 95% asymmetric antibody product, less than 5% monomers, and undetectable amounts of homodimers of said first or second heavy chain polypeptide.

In accordance with another aspect of the invention there is provided a method of producing an asymmetric antibody product comprising at least a first heavy chain polypeptide and at least a second heavy chain polypeptide in mammalian cells, the method comprising: a. transiently transfecting at least one mammalian cell pool with: i) a first DNA sequence encoding the first heavy chain polypeptide, wherein the first heavy chain polypeptide comprises a variant CH3 sequence; and ii) a second DNA sequence encoding at least the second heavy chain polypeptide, wherein the second heavy chain polypeptide comprises a variant CH3 sequence different from the first heavy chain polypeptide; and wherein: a) the variant CH3 sequences of the first and second heavy chain polypeptides promote the formation of a heterodimeric Fc region comprising a CH3 domain with a Tm of greater than 75° C.; b) the first and second heavy chain polypeptides preferentially exist as monomers rather than homodimers when not present in the heterodimeric form; and such that said first DNA sequence and said second DNA sequence are transfected in said mammalian cell in a pre-determined ratio to generate transiently transfected mammalian cells; and b. culturing said transiently transfected mammalian cells to produce an expression product comprising greater than 95% asymmetric antibody product, less than 5% monomers, and undetectable amounts of homodimers of said first or second heavy chain polypeptide.

The present disclosure relates to stable mammalian cell lines for the production of glycosylated antibody variants, and for the production of heteromultimers comprising heterodimeric Fc domains. More specifically, provided herein are methods of producing a glycosylated asymmetric antibody in a stable mammalian cell and methods of screening cell-lines to produce a substantially pure glycosylated asymmetric antibody.

Provided herein is a method of producing a glycosylated asymmetric antibody in stable mammalian cells, comprising: transfecting at least one stable mammalian cell with a first DNA sequence encoding a first heavy chain polypeptide; a second DNA sequence encoding a second heavy chain polypeptide different from the first heavy chain polypeptide; and a third DNA sequence encoding a light chain polypeptide, such that the said first, second and third DNA sequences are transfected in said mammalian cell in a pre-determined ratio; and translating the first, second and third DNA sequences in the at least one mammalian cell such that said heavy and light chain polypeptides are expressed as the desired glycosylated asymmetric antibody in the at least one stable mammalian cell. In certain embodiments, a stable cell line clone is derived from the stable mammalian cell. In certain embodiments is a method of producing a glycosylated asymmetric antibody in stable mammalian cells, comprising transfecting at least two different stable mammalian cells with different pre-determined ratios of the first DNA sequence, said second DNA sequence and said third DNA sequence such that each of the two cells expresses the heavy chain polypeptides and the light chain polypeptide in a different ratio. In some embodiment is a method of selecting one stable cell line clone from the at least two different stable mammalian cell lines. In certain embodiments provided is a method of producing glycosylated asymmetric antibody in a pool of stable mammalian cells, each cell transfected with the first, second and third DNA sequence. In certain embodiments provided is a method of producing glycosylated asymmetric antibody in a pool of stable mammalian cells, where in each cell in the pool of cells is a clone of the same stable cell.

In certain embodiments of the methods provided herein, the predetermined ratio of the first DNA sequence, second DNA sequence and third DNA sequence is about 1:1:3. In certain embodiments, the predetermined ratio of the first DNA sequence, second DNA sequence and third DNA sequence is such that the amount of translated first heavy chain polypeptide is about equal to the amount of the second heavy chain polypeptide, and the amount of the light chain polypeptide is at least about two fold greater than the amounts of either of the heavy chain polypeptides. In certain embodiments, the predetermined ratio of the first DNA sequence:second DNA sequence:third DNA sequence is such that the amount of translated first heavy chain polypeptide is greater than the amount of the second heavy chain polypeptide, and the amount of the light chain polypeptide is at least about two fold greater than the amount of the first heavy chain polypeptide. In certain embodiments, the predetermined ratio of the first DNA sequence:second DNA sequence is such that the amount of first DNA sequence is greater than the amount of second DNA sequence but the amount of translated first heavy chain polypeptide is about equal to the amount of the second heavy chain polypeptide and the amount third DNA sequence is such that the amount of the light chain polypeptide is at least about two fold greater than the amount of the first heavy chain polypeptide. In certain embodiments, the predetermined ratio of the first DNA:the second DNA:the third DNA is such that the amount of translated first heavy chain polypeptide is less than the amount of the second heavy chain polypeptide, and the amount of the light chain polypeptide is at least about two fold greater than the amount of the second heavy chain polypeptide. In certain embodiments, the predetermined ratio of the first DNA:the second DNA is such that the amount of first DNA sequence is less than the amount of second DNA sequence but the amount of translated first heavy chain polypeptide is equal to the amount of the second heavy chain polypeptide, and the amount of third DNA sequence is such that the amount of the light chain polypeptide is at least about two fold greater than the amount of the second heavy chain polypeptide.

In certain embodiments, the method comprises transfecting the at least one mammalian cell with a multi-cistronic vector comprising said first, second and third DNA sequence. In certain embodiments, the at least one mammalian cell is selected from the group consisting of a VERO, Hela, HEK, NSO, Chinese Hamster Ovary (CHO), W138, BHK, COS-7, Caco-2 and MOCK cell, and subclasses and variants thereof.

Provided herein is a method of producing a glycosylated asymmetric antibody in stable mammalian cells, comprising: transfecting at least one stable mammalian cell with a first DNA sequence encoding a first heavy chain polypeptide, a second DNA sequence encoding a second heavy chain polypeptide different from the first heavy chain polypeptide, and a third DNA sequence encoding a light chain polypeptide, such that the said first, second and third DNA sequences are transfected in said mammalian cell in a pre-determined ratio; translating the first, second and third DNA sequences in the at least one mammalian cell such that said heavy and light chain polypeptides are expressed as the desired glycosylated asymmetric antibody in the at least one stable mammalian cell; and identifying and purifying the desired glycosylated asymmetric antibody. In certain embodiments, the identification is by a standard protein analytical technique. In certain embodiments, the standard protein analytical technique is one or more of SDS-PAGE, liquid chromatography, mass spectrometry and combinations thereof.

Provided herein is a method of producing a glycosylated asymmetric antibody in stable mammalian cells, comprising: transfecting at least one stable mammalian cell with a first DNA sequence encoding a first heavy chain polypeptide; a second DNA sequence encoding a second heavy chain polypeptide different from the first heavy chain polypeptide; and a third DNA sequence encoding a light chain polypeptide, such that the said first, second and third DNA sequences are transfected in the mammalian cell in a pre-determined ratio; translating the first, second and third DNA sequences in the at least one mammalian cell such that the heavy and light chain polypeptides are expressed as the desired glycosylated asymmetric antibody in the at least one stable mammalian cell; and wherein the expression product of the at least one mammalian cell comprises a larger percentage of the desired glycosylated asymmetric antibody as compared to the monomeric heavy or light chain polypeptides, or other antibodies. In certain embodiments, the expression product of the at least one stable mammalian cell comprises a greater percentage of the glycosylated asymmetric antibody compared to symmetric antibodies. In certain embodiments, the expression product comprises a greater than two fold excess of the asymmetric antibodies compared to the symmetric antibodies. In certain embodiments, the expression product of the at least one stable mammalian cell comprises of only the glycosylated asymmetric antibody and none of the symmetric antibodies.

Provided herein is a method of producing a glycosylated heteromultimer in a stable mammalian cell-line, comprising: transfecting at least one stable mammalian cell with: a first DNA sequence encoding at least a first immunoglobulin heavy chain polypeptide, and a second DNA sequence encoding at least a second immunoglobulin heavy chain polypeptide different from the first heavy chain polypeptide; such that said first and second DNA sequences are transfected in the mammalian cell in a pre-determined ratio; and translating the first and the second DNA sequences in the mammalian cell such that the immunoglobulin heavy chain polypeptides are expressed as the desired glycosylated heteromultimer in the stable mammalian cell-line.

Provided herein is a method of producing a heteromultimer in stable mammalian cells, comprising: transfecting at least one stable mammalian cell with: a first DNA sequence encoding at least a first immunoglobulin heavy chain polypeptide; and a second DNA sequence encoding at least a second immunoglobulin heavy chain polypeptide different from the first heavy chain polypeptide such that the first and second DNA sequences are transfected in said mammalian cell in a pre-determined ratio; and translating the first and second DNA sequences in the mammalian cell such that the immunoglobulin heavy chain polypeptides are expressed as the desired heteromultimer in the transformed at least one mammalian cell. In certain embodiments, at least one of the first and second DNA sequences also encodes one or more of a single-chain Fv segment and a single-chain Fab segment. In certain embodiments, at least one of the first and second DNA sequences also encodes one or more of a non-antibody protein segment. In certain embodiments, the method of producing a heteromultimer in stable mammalian cells comprises identifying and purifying the desired heteromultimer. In some embodiments, the identification is by one or both of liquid chromatography and mass spectrometry. In certain embodiments, the predetermined ratio of the first DNA sequence to second DNA sequence is such that amount of translated first immunoglobulin heavy chain polypeptide is about equal to the amount of translated second immunoglobulin heavy chain polypeptide. In certain embodiments, the predetermined ratio of said first DNA sequence to second DNA sequence is such that the amount of translated first immunoglobulin heavy chain polypeptide is less than the amount of translated second immunoglobulin heavy chain polypeptide. In certain embodiments, the predetermined ratio of said first DNA sequence to second DNA sequence is such that the amount of translated second immunoglobulin heavy chain polypeptide is less than amount of second immunoglobulin heavy chain polypeptide. In certain embodiments described herein, the mammalian cell is selected from the group consisting of a VERO, Hela, HEK, NSO, Chinese Hamster Ovary (CHO), W138, BHK, COS-7, Caco-2 and MOCK cell, and subclasses and variants thereof. In certain embodiments, the method comprises producing said heteromultimer in a pool of mammalian cells, each cell transfected with said first, and second DNA sequence.

Provided herein is a method of screening mammalian cell-lines to produce a substantially pure glycosylated asymmetric antibody, said method comprising: transfecting mammalian cells with different ratios of a first DNA sequence encoding a first heavy chain polypeptide; a second DNA sequence encoding a second heavy chain polypeptide different from the first heavy chain polypeptide; expressing said first and second DNA sequences in the mammalian cell such that the heavy chain polypeptides are expressed as the desired glycosylated asymmetric antibody in the transformed mammalian cell; determining the purity of desired glycosylated asymmetric antibody expressed by the different cells; identifying and isolating the mammalian cell which expresses the desired glycosylated asymmetric antibody with maximum purity, thereby identifying the optimum ratio of the first DNA sequence:second DNA sequence for transfecting the mammalian cell type. In certain embodiments, a stable cell line clone is derived from the selected stable cell.

In certain embodiments the purity is determined by one or both of liquid chromatography and mass spectrometry. In some embodiments, the purity is determined by ion exchange chromatography or by gel isolation. In some embodiments, the mammalian cell-line is selected from the group consisting of a VERO, Hela, HEK, NSO, Chinese Hamster Ovary (CHO), W138, BHK, COS-7 Caco-2, MOCK cell and subclasses and variants thereof.

3. BRIEF DESCRIPTION OF THE FIGURES

These and other features of the invention will become more apparent in the following detailed description in which reference is made to the appended drawings.

FIG. 1 depicts 9 stable CHO pools that were generated by transfection with different ratios of the light chain polypeptide and two different heavy chain polypeptides of an asymmetric antibody construct.

FIGS. 2 A and 2B provide LC/MS screening results of the proteins expressed by the 9 stable CHO pools described in FIG. 1, and Example 1. FIG. 2A depicts the results of pools J to M. FIG. 2B depicts the results of pools N to R.

FIGS. 3A and 3B provide further LC/MS characterization of the protein A purified samples of proteins expressed by the 9 stable CHO pools described in FIG. 1, and Example 1. The figure shows that the preferred pool (N) does not form any homodimer. FIG. 3B Provides LC/MS analysis of the stable CHO pools described in FIG. 1 and Example 1. Describes the ratio of heterodimers to homodimers to monomers, expressed as a percentage of total antibody content.

FIG. 4 shows use of LC/MS to analyze purity of different heterodimers that comprise two different antibody heavy chain polypeptides, and a common light chain. The figure provides LC/MS characterization of asymmetric antibodies produced by transient co-expression (3 plasmids for light chain, heavy chain A and heavy chain B) using 3 different DNA ratios of the two heavy chains A and B (e.g. ratios A:B=1:1.5; 1:1; 1.5:1).

FIGS. 6A, 6B and 6C represent the asymmetric form of antibody derived from two different heavy chains compared to the two other symmetric forms derived from the association of similar heavy chains.

FIG. 9 is a LCMS spectrum analysis of Ncp104, as described in Example 4. The top graph is a full spectrum, demonstrating that the Ncp104 construct produces significantly more of the dimer than the monomer product. The middle graph represents deconvoluted dimers. The bottom graph represents deconvoluted monomers.

Figure 10:
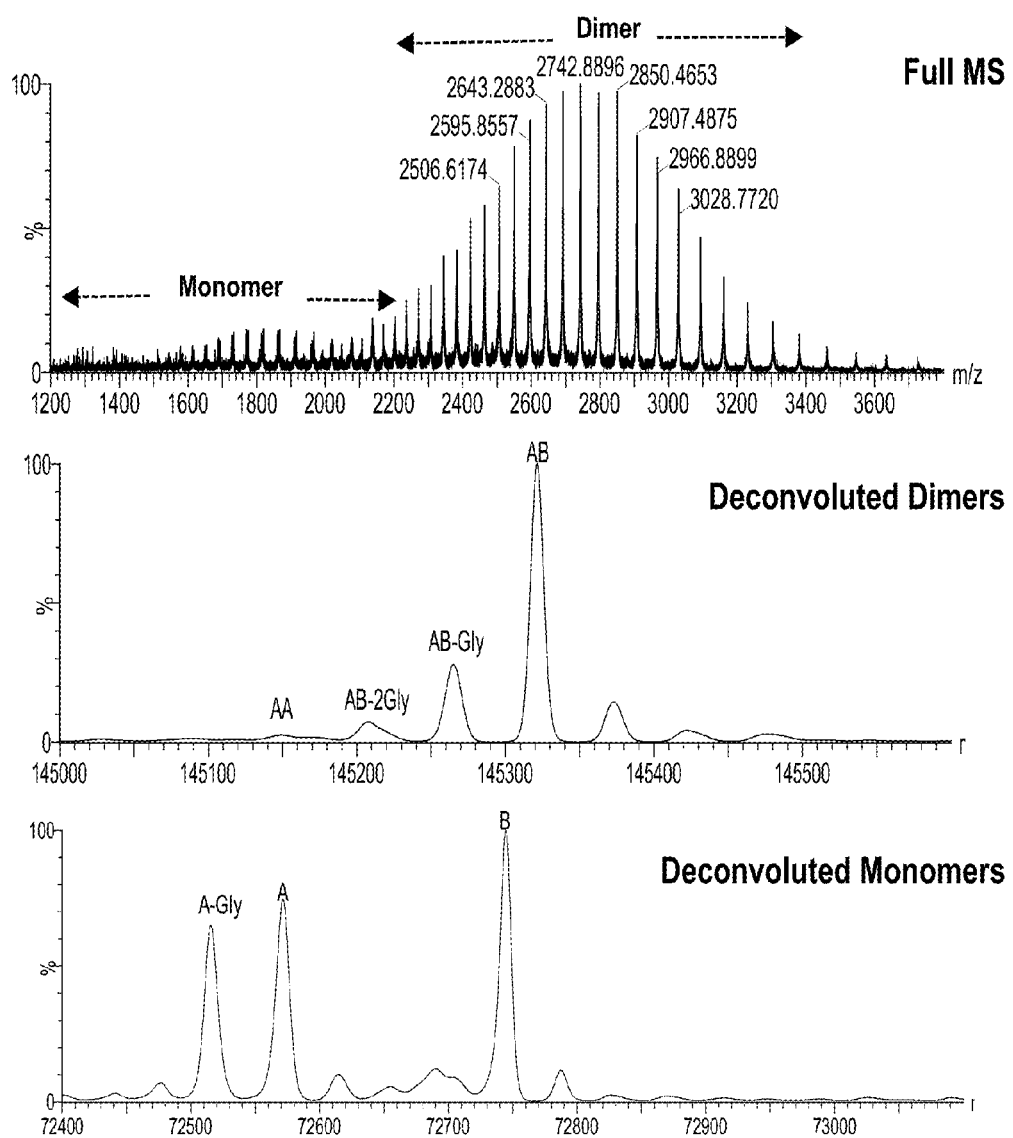

FIG. 10 is a LCMS spectrum analysis of Ncp110, as described in Example 4. The top graph is a full spectrum, demonstrating that the Ncp110 construct produces significantly more of the dimer than the monomer product. The middle graph represents deconvoluted dimers. The bottom graph represents deconvoluted monomers.

Figure 11A:
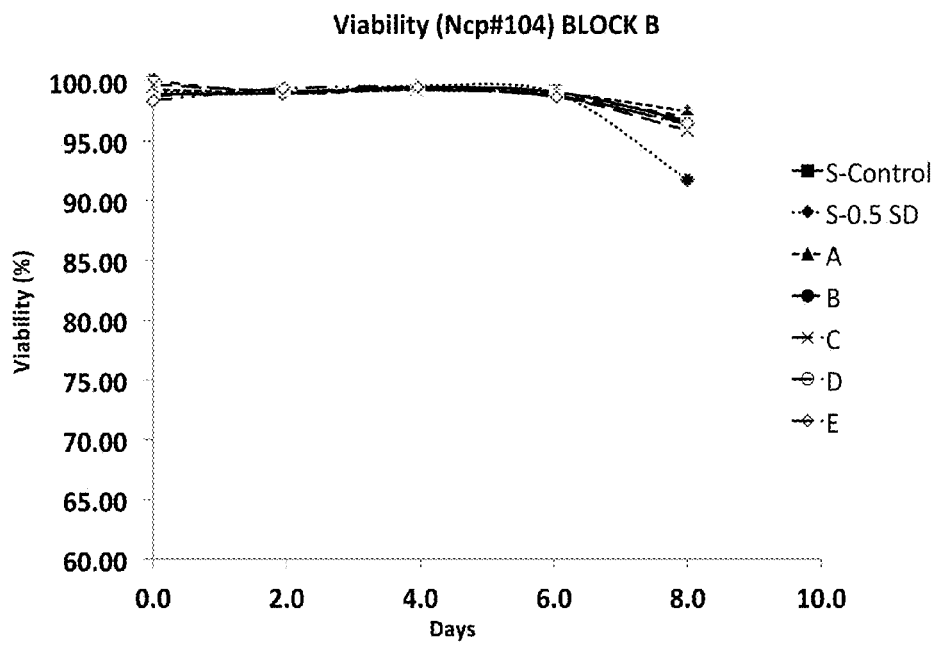
Figure 11B:
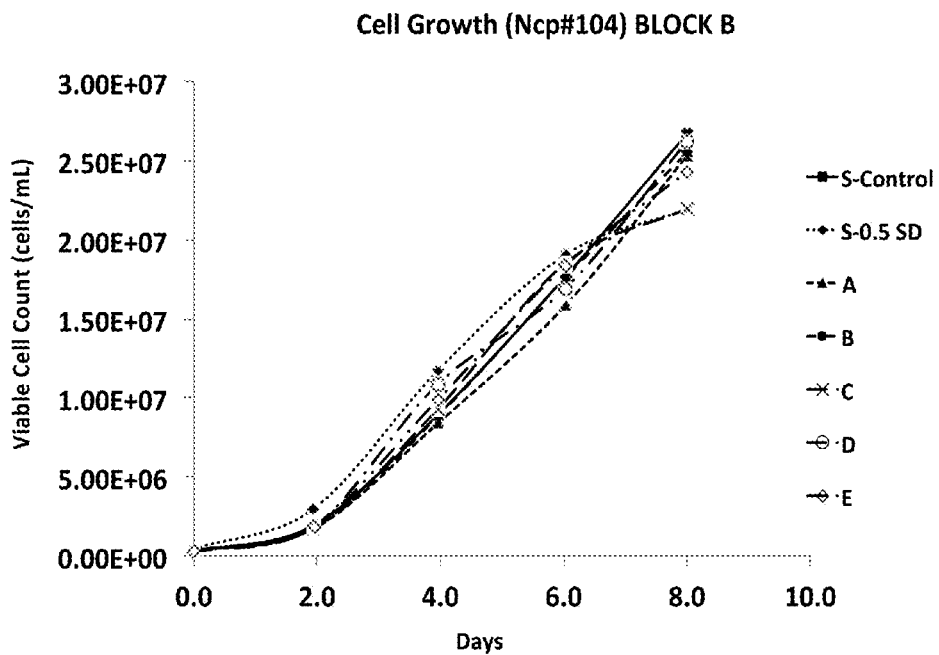
Figure 11C:
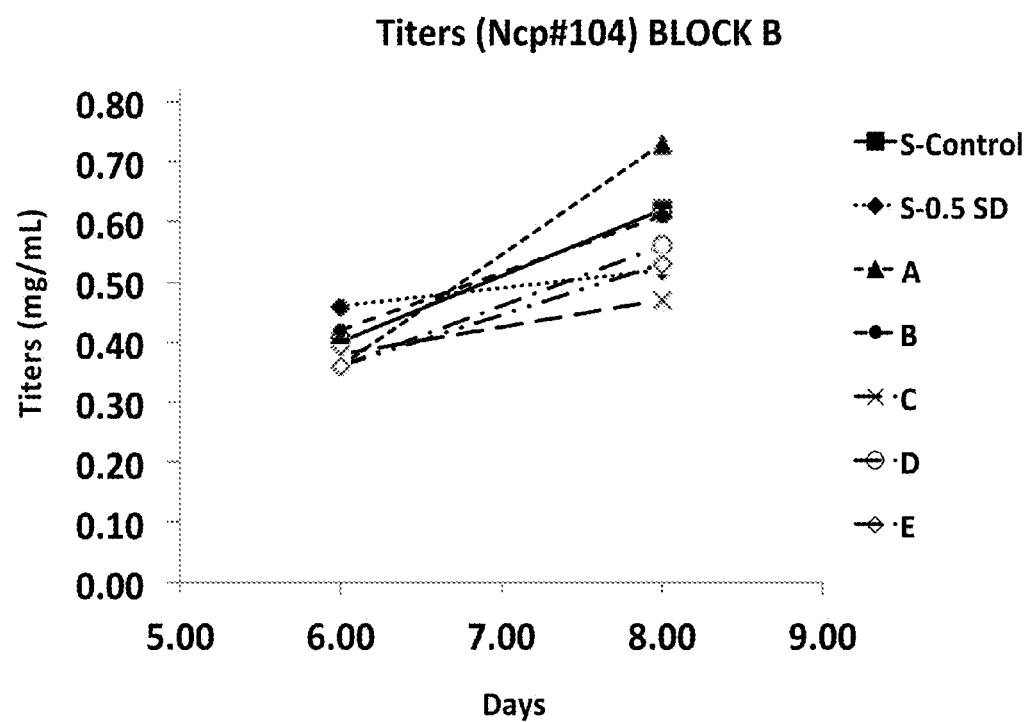

FIGS. 11A, 11B and 11C are a comparison of the percentage cell viability of the Ncp104 construct cultured in seven different growth/feed conditions, as described in Example 6. FIG. 11B Is a comparison of the cell growth concentration in cells/ml of the Ncp104 construct cultured in seven different growth/feed conditions, as described in Example 6. FIG. 11C is a comparison of antibody titer in mg/ml of the Ncp104 construct cultured in seven different growth/feed conditions, as described in Example 6.

Figure 12A:
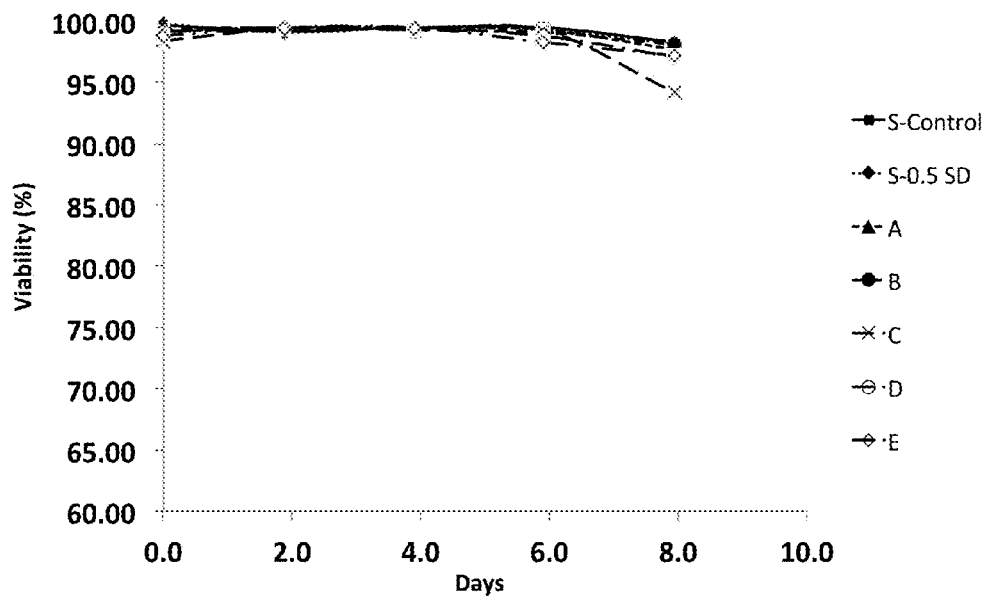
Figure 12B:
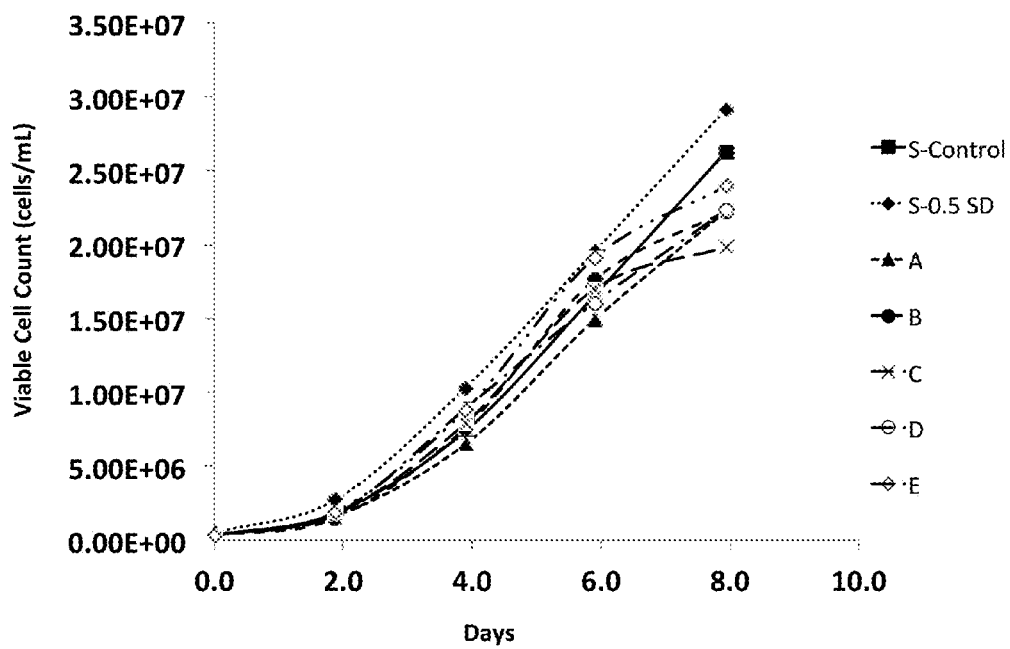

FIGS. 12A, 12B and 12C are a comparison of the percentage cell viability of the Ncp110 construct cultured in even different growth/feed conditions, as described in Example 6. FIG. 12B is a comparison of the cell growth concentration in cells/ml of the Ncp110 construct cultured in seven different growth/feed conditions, as described in Example 6. FIG. 12C is a comparison of antibody titer in mg/ml of the Ncp104 construct cultured in seven different growth/feed conditions, as described in Example 6.

Figure 13:
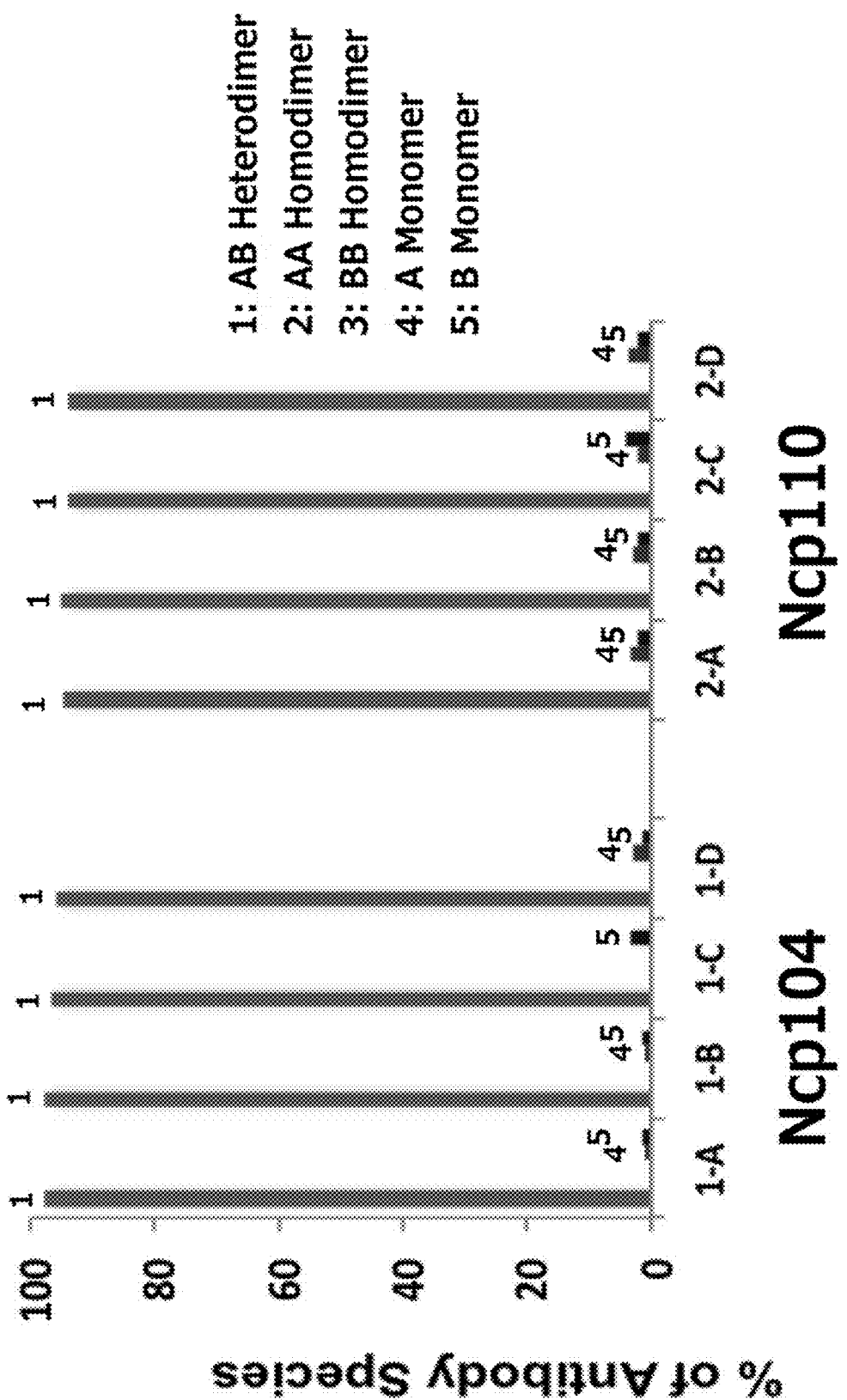

FIG. 13 is a normalized LC/MS analysis of the heterodimeric purity of the two stable CHO clones, Ncp104 and Ncp110, as described in Example 7. The figure expresses the ratio of homodimer to heterodimer to monomer antibody products as a percentage of total antibody species.

FIGS. 14A and 14B provide the amino acid sequence of the wildtype antibody light chain described in Example 3 while FIG. 14B provides the corresponding nucleotide sequence.

FIGS. 15A and 15B provide the amino acid sequence of the wildtype antibody heavy chain described in Example 3 while FIG. 15B provides the corresponding nucleotide sequence.

FIGS. 16A, 16B, 16C and 16D represent the amino acid sequence of the ful-length heavy chain polypeptide (chain A) described in Example 10 prior to variant mutation. FIG. 16B represents the corresponding nucleotide sequence of chain A. FIG. 16C represents the amino acid sequence of the Fc heavy chain fragment (chain B) described in Example 10 prior to variant mutation. FIG. 16D represents the chain B's corresponding nucleotide sequence.

Figure 17A:
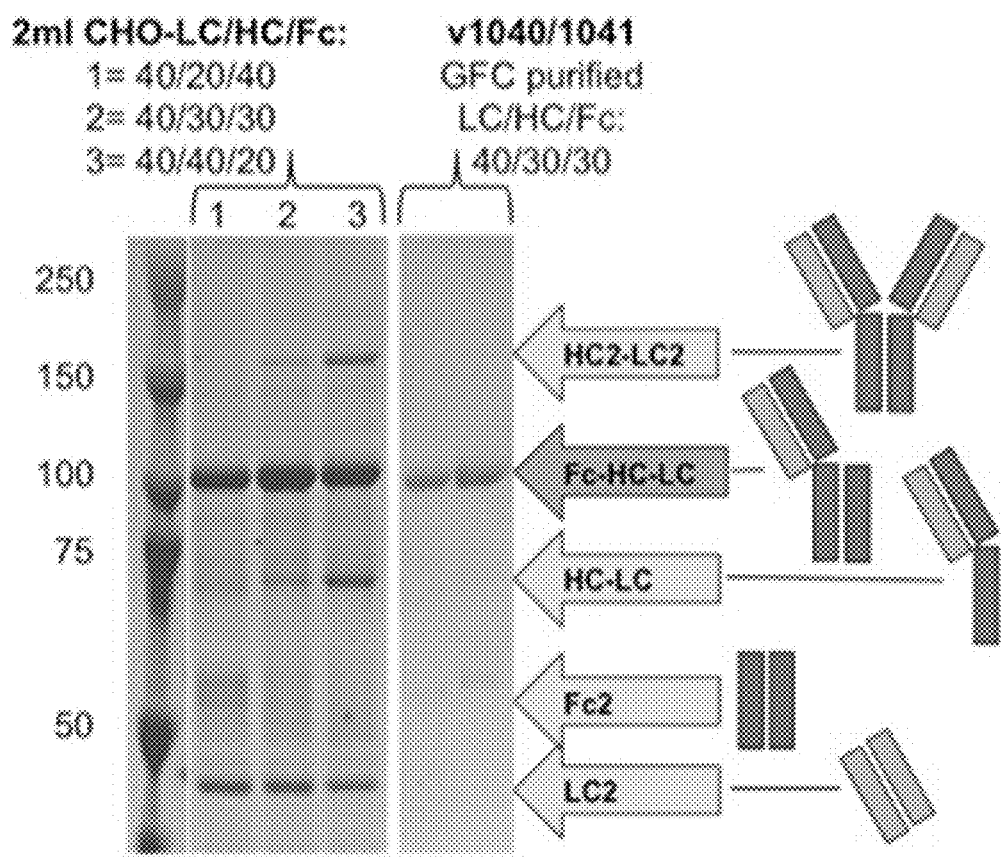
Figure 17B:
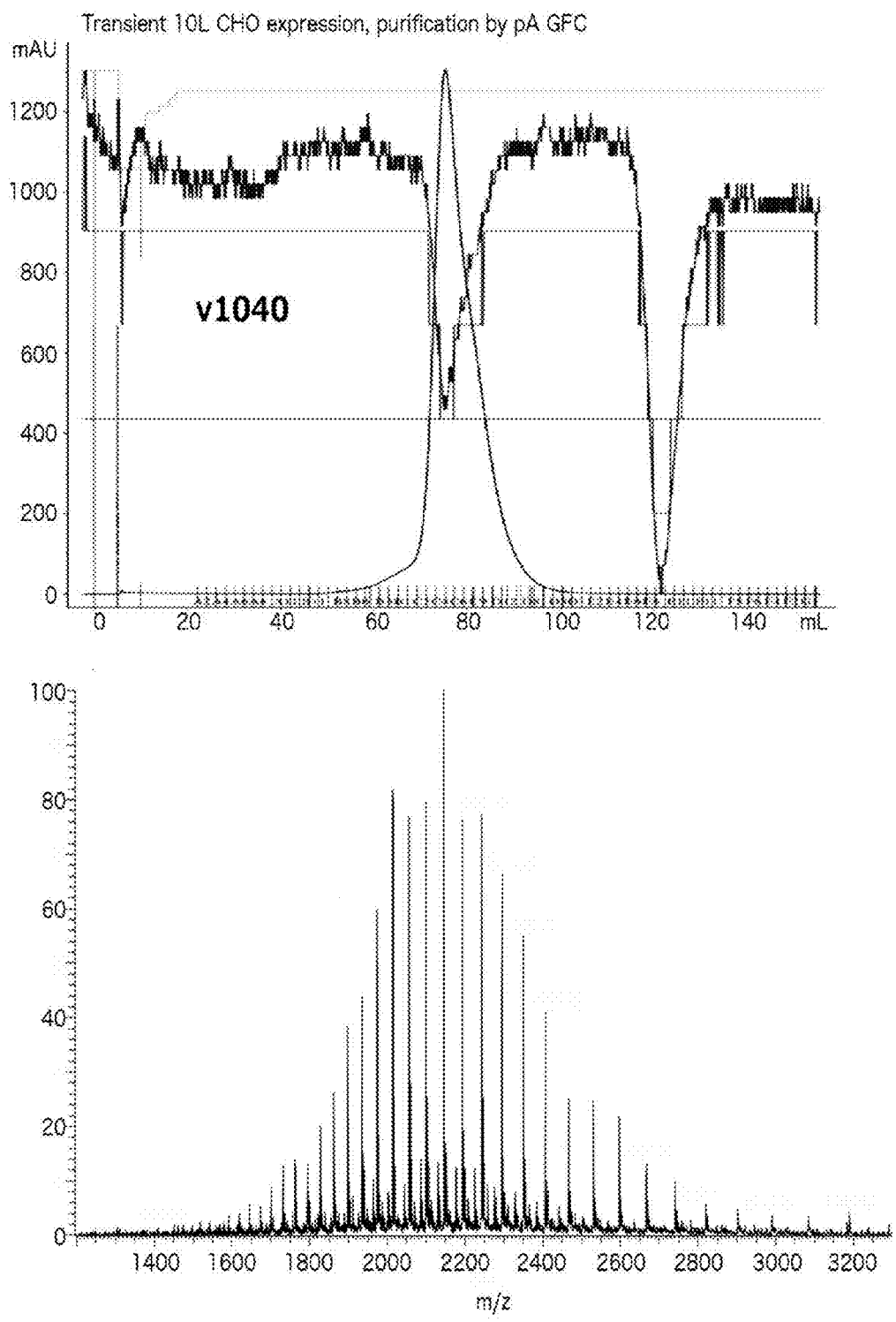

FIGS. 17A and 17B are an SDS-PAGE analysis of the expression products the two variants, v1040 and v1041, at different LC/HC/Fc ratios. The figures also demonstrate heterodimeric product purity after protein A and GFC processing. FIG. 17B is the chromatogram and corresponding mass spectrogram of the expression products after said protein A and GFC purification.

Figure 18A:
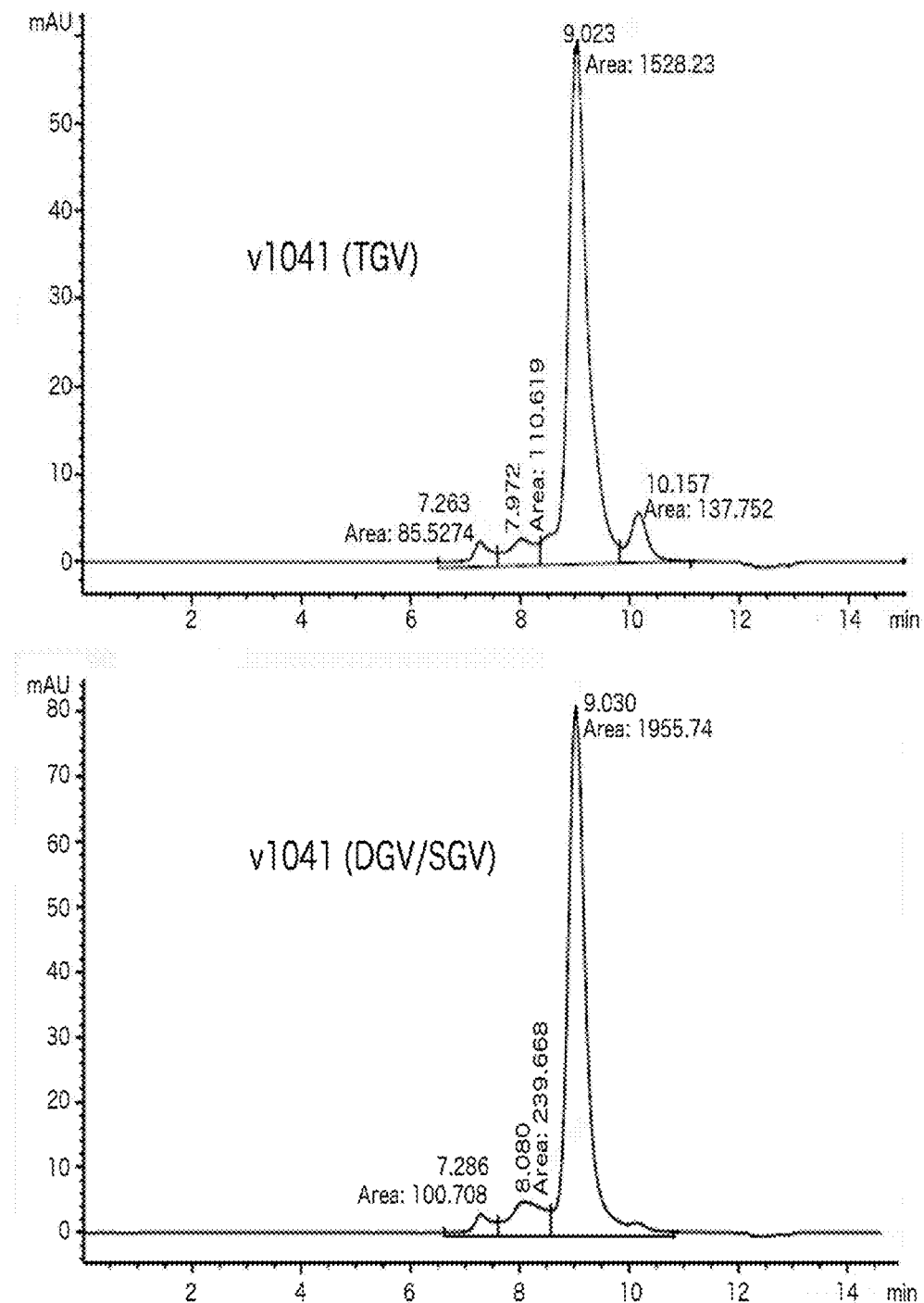

FIGS. 18A and 18B show the results of the HPLC-SEC analysis of protein A purified expression products for both v1040 and v1041 transfected using either the triple gene vector (TGV) or the combination of the double gene vector and single gene vector (DGV/SGV). FIG. 18B is mass spectrograms of the expression products of both variants from transfection using the TGV system.

Figure 19:
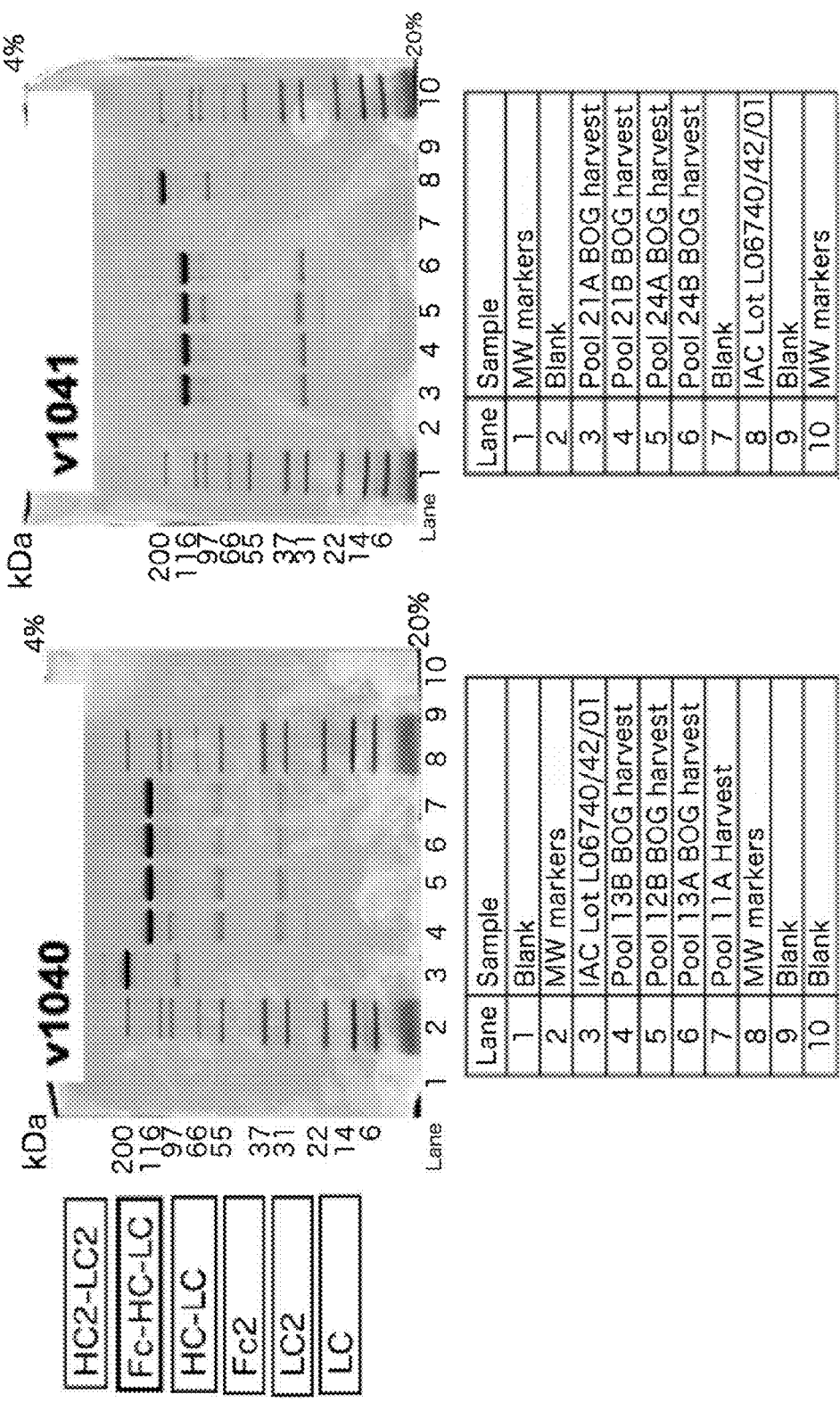

FIG. 19 is the SDS-PAGE analysis of the expression product of CHOK1SV cells stably transfected with 1040 and 1041 using the TGV system. The four pools for each variant were selected on the basis of protein A titre and Capiler results as described in Example 13.

FIGS. 20A and 20B are the HPLC-SEC analysis of the purity of each 1040 variant pool. FIG. 20B is the HPLCSEC analysis of the purity of 1041 variant pool.

Figure 21:
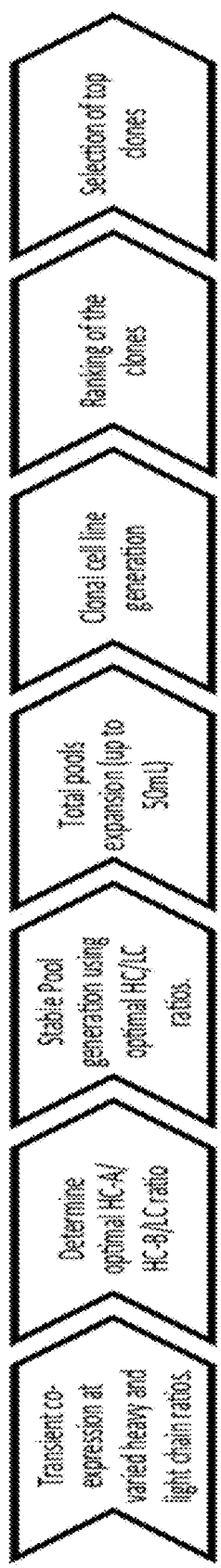

FIG. 21 is a process diagram providing an overview of the steps leading to the selection of Ncp104 and Ncp110 as top clones expressing heterodimeric product.

Figure 22:
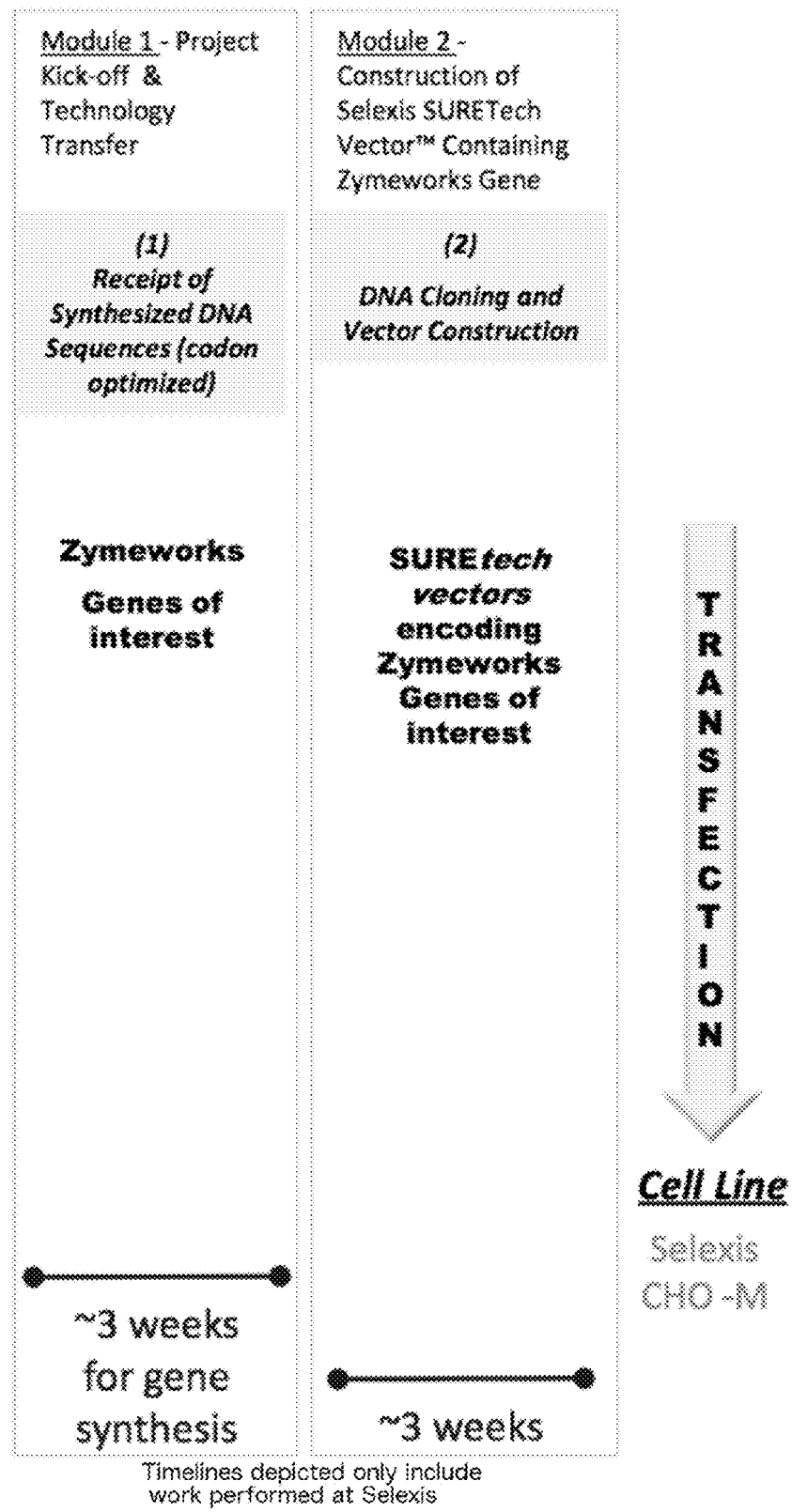
Figure 22:
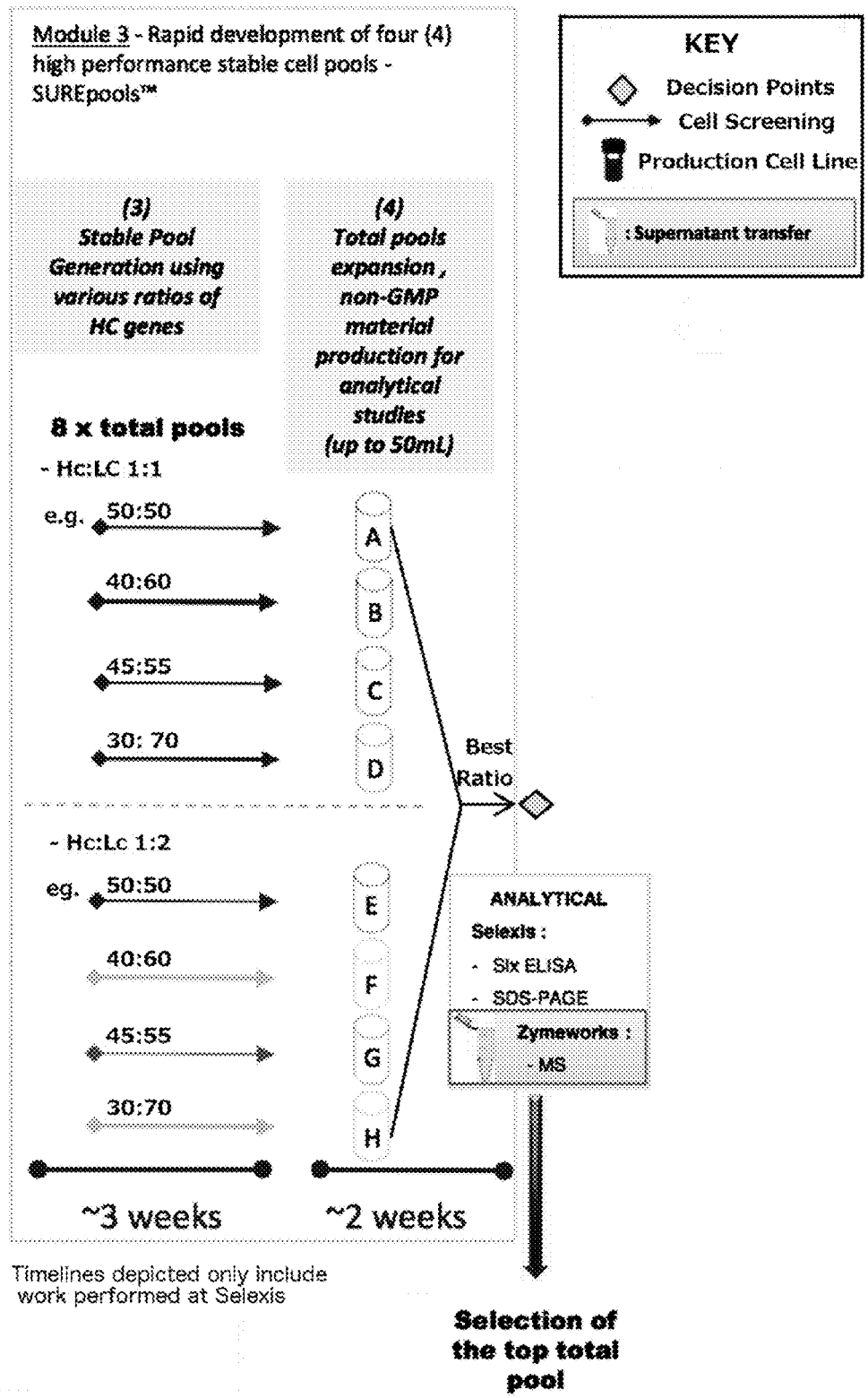
Figure 22:
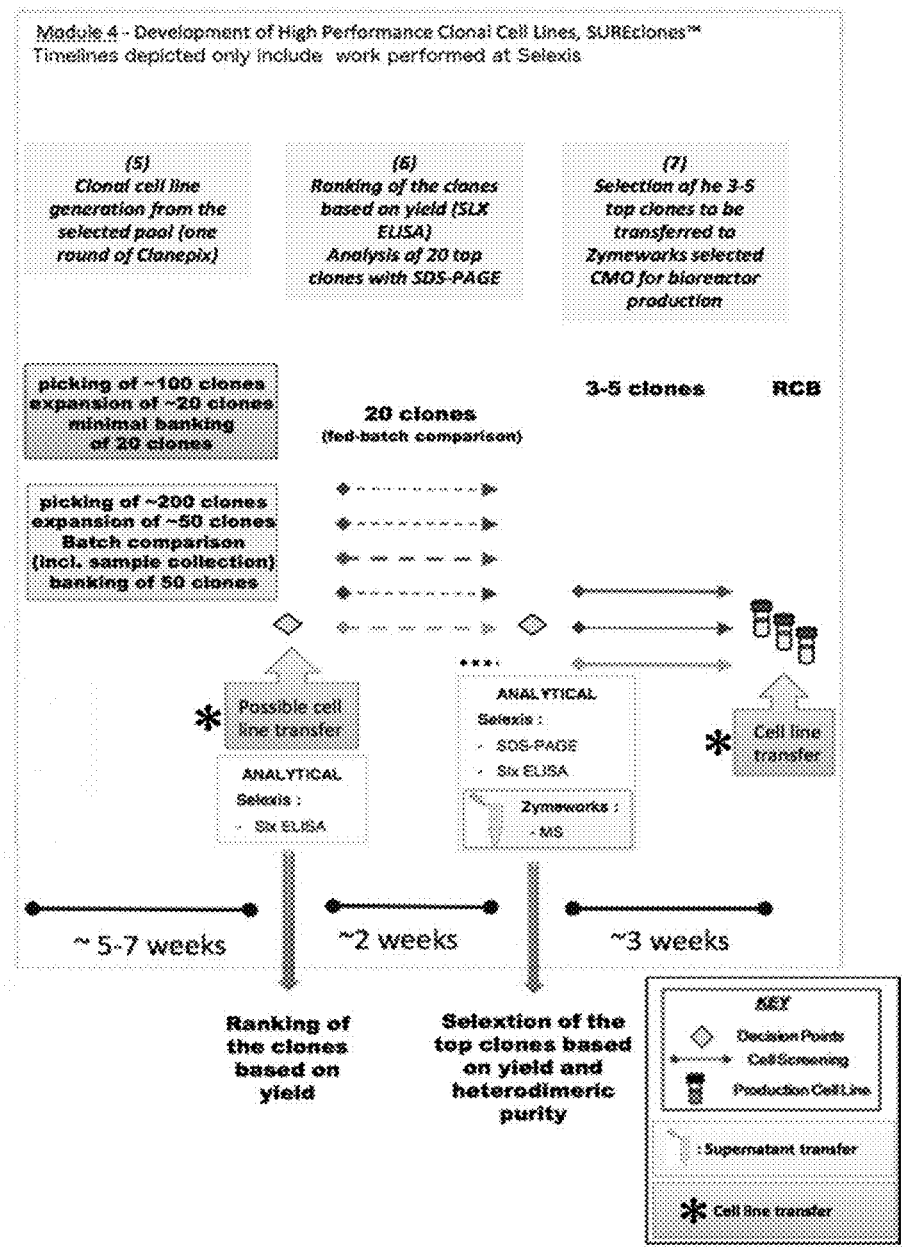

FIG. 22 is a process diagram providing an overview of the steps leading to the identification of certain clones as the top producers of heterodimeric antibody product.

4. DETAILED DESCRIPTION

Provided herein are processes and methods for producing asymmetric antibodies in a mammalian expression system. The asymmetric antibodies are transiently or stably expressed and in cells that stably express the asymmetric antibody, following a rapid 2-step process of stable pool to clone, a highly pure asymmetric antibody expressing clone can be identified at a success frequency that permits for screening of tens of clones rather than thousands. The asymmetric antibodies are produced at a high titre and with a high level of purity with no contaminating homodimer antibodies following protein A purification with a step yield of near 100%. Typical downstream purification processes employ standard hydrophobic interaction chromatography (HIC) and/or cation exchange (CEX) resins and the antibody is stable within a wide dynamic range of buffer pH (4-8) and within the requirements for manufacturing antibodies for pre-clinical and clinical applications.

The process is suitable for use with certain asymmetric antibodies comprising a heterodimeric Fc region, as described herein. The rapid and efficient generation and use of a recombinant mammalian cell line stably expressing the asymmetric antibodies at high titre and purity allows for manufacturability of asymmetric antibodies in bioreactors (up to 20,000 L), minimizes product-lot-variability to rapidly show batch selection for a market authorization eg. Antibody product reproducibility over at least 3 batches representative of the manufacturing scale of production, product formulation stability, production process verification and quality assurance activities to support IND-enabling non-GMP batches for preclinical and cGMP material for clinical activities, antibody product demonstrates comparable biophysical attributes as a wildtype antibody for drug conjugation.

Once the asymmetric antibody to be produced is selected, the process is carried out by first identifying a pre-determined ratio of the nucleic acid encoding the polypeptide chains of the asymmetric antibody that provide optimal expression of asymmetric antibodies with minimal amounts of unwanted products, such as homodimers or monomers of the heavy chain polypeptides using transient expression methods. The predetermined ratio is determined by carrying out test transfections with various ratios of nucleic acids encoding the different polypeptides of the asymmetric antibody, and analyzing the expressed products to quantify the amounts of the expressed products. In one embodiment, the test transfections are carried out in a transient transfection system. One or more predetermined ratios resulting in the optimal expression of the expressed products are then used to generate transfected cells expressing the asymmetric antibodies. In one embodiment, the predetermined ratio is used to generate a stably transfected cell. The predetermined ratio used in transient cell expression to obtain the antibody substance and generation of a stable cell pool expressing the antibody substance is identical and thus fidelity is high. Pools that exhibit the desired characteristics are then cultivated and individual clones exhibiting the desired characteristics are selected and evaluated for overall yield of the asymmetric antibodies produced. Such a clone is obtained at a high frequency such as, for example, 1/20 clones. The clone can subsequently be cultivated using standard methods to obtain a research and master cell bank.

The resulting asymmetric antibodies exhibit properties that are desirable with respect to manufacturing of a drug candidate, including process stability, product stability and quality.

Provided herein are stable pools of mammalian cells that co-express two different heavy chains to produce a pure asymmetric antibody species with high yield and purity, wherein said antibody species comprises a heterodimeric Fc region. In one embodiment the two heavy chains are coexpressed with a single light chain.

Also provided are methods of screening mammalian cell-lines wherein plasmids for the two different heavy chains (HCA and HCB, or first heavy chain polypeptide and second heavy chain polypeptide) along with the plasmid for the light chain were transfected at different ratios of the heavy and light chains. The expressed protein is characterized by standard techniques such as LCMS, and the stable pools of mammalian cells transfected with a particular heavy chain A:B DNA ratio that produce a pure asymmetric antibody are isolated.

Co-expressing two different heavy chains to obtain a pure and homogeneous heterodimeric species has been a challenge (US20090232811 para 268) even at the transient expression level. Obtaining stable cell lines with such designs presents further challenges and would require extensive screening for stable clones. The method presented herein to develop a stable mammalian cell line expressing the homogeneous asymmetric antibody is a rational and novel approach based on a molecular design strategy to address this problem and has not been achieved by anybody in the literature.

Provided herein is a method of pure and homogeneous heterodimer expression in stable mammalian cell lines, wherein the heterodimer can be further purified in a regular purification process. Provided is a process for the large scale production of asymmetric and bi-specific antibodies in a single expression system with good yield and purity and avoiding the need to carry out multistep process involving expression in two different cell lines followed by purification and annealing, followed by further purification steps.

Definitions

As used herein, "antibodies" or "heteromultimers" refers to tetramers which have specific immunoreactive activity, comprising light and heavy chains usually in the "Y" configuration, with or without covalent linkage between them.

In the present description, any concentration range, percentage range, ratio range, or integer range is to be understood to include the value of any integer within the recited range and, when appropriate, fractions thereof (such as one tenth and one hundredth of an integer), unless otherwise indicated. As used herein, "about" means±10% of the indicated range, or value, unless otherwise indicated. It should be understood that the terms "a" and "an" as used herein refer to "one or more" of the enumerated components unless otherwise indicated or dictated by its context. The use of the alternative (e.g., "or") should be understood to mean either one, both, or any combination thereof of the alternatives. As used herein, the terms "include" and "comprise" are used synonymously. In addition, it should be understood that the individual single chain polypeptides or heterodimers derived from various combinations of the structures and substituents (e.g., variant CH3 domains) described herein are disclosed by the present application to the same extent as if each single chain polypeptide or heterodimer were set forth individually.

Thus, selection of particular components to form individual single chain polypeptides or heterodimers is within the scope of the present disclosure.

The "first heavy chain polypeptide" is any polypeptide that is to be associated with a second heavy chain polypeptide, also referred to herein as "first antibody heavy chain polypeptide". The first and second polypeptide meet at an "interface". The "second heavy chain polypeptide" is any polypeptide that is to be associated with the first heavy chain polypeptide via an "interface", also referred to herein as "second antibody heavy chain polypeptide". Said first and second polypeptides each comprise at least one heavy chain variable domain. The "interface" comprises those "contact" amino acid residues in the first polypeptide that interact with one or more "contact" amino acid residues in the interface of the second polypeptide. As used herein, the interface comprises the CH3 domain of an Fc region. In some embodiments, the Fc region is derived from an lgG antibody such as, but not restricted to a human lgG1 antibody. In certain embodiments, the at least one heavy chain variable domain is connected to the CH3 domain by means of a linker.

As used herein, "isolated asymmetric antibody" or "isolated heteromultimer" means a glycosylated antibody or a heteromultimer that has been identified and separated and/or recovered from a component of its natural cell culture environment. Contaminant components of its natural environment are materials that would interfere with diagnostic or therapeutic uses for the heteromultimer, and may include enzymes, hormones, and other proteinaceous or non-proteinaceous solutes.

Selection Frequency, Protein Expression Frequency, Different Process Development Steps Provided herein is a method of producing a glycosylated asymmetric antibody in stable mammalian cells, comprising: transfecting at least one stable mammalian cell with a first DNA sequence encoding a first heavy chain polypeptide; a second DNA sequence encoding a second heavy chain polypeptide different from the first heavy chain polypeptide; and a third DNA sequence encoding a light chain polypeptide, such that the said first, second and third DNA sequences are transfected in said mammalian cell in a pre-determined ratio; and translating the first, second and third DNA sequences in the at least one mammalian cell such that said heavy and light chain polypeptides are expressed as the desired glycosylated asymmetric antibody in the at least one stable mammalian cell. In certain embodiments is a method of producing a glycoslyated asymmetric antibody in stable mammalian cells, comprising transfecting at least two different stable mammalian cells with different pre-determined ratios of the first DNA sequence, said second DNA sequence and said third DNA sequence such that each of the two cells expresses the heavy chain polypeptides and the light chain polypeptide in a different ratio. In certain embodiments provided is a method of producing glycosylated asymmetric antibody in a pool of mammalian cells, each cell transfected with the first, second and third DNA sequence.

In certain embodiments of the methods provided herein, the predetermined ratio of the first DNA sequence, second DNA sequence and third DNA sequence is about 1:1:3. In certain embodiments, the predetermined ratio of the first DNA sequence, second DNA sequence and third DNA sequence is such that the amount of translated first heavy chain polypeptide is about equal to the amount of the second heavy chain polypeptide, and the amount of the light chain polypeptide is at least about two fold greater than the amounts of either of the heavy chain polypeptides. In certain embodiments, where the first heavy chain polypeptide and the second heavy chain polypeptide are produced in the mammalian cell at different levels, for example due to differing levels of transcriptional, translational, processing, or secretory efficiencies, the predetermined ratio of the first DNA sequence:second DNA sequence:third DNA sequence is such that the amount of translated first heavy chain polypeptide is greater than the amount of the second heavy chain polypeptide, and the amount of the light chain polypeptide is at least about two fold greater than the amount of the first heavy chain polypeptide. In related embodiments, the predetermined ratio of the first DNA:the second DNA:the third DNA is such that the amount of translated first heavy chain polypeptide is less than the amount of the second heavy chain polypeptide, and the amount of the light chain polypeptide is at least about two fold greater than the amount of the second heavy chain polypeptide. In certain embodiments, such an altered ratio resulting in one chain being expressed more than the other is useful when it is acceptable or preferable to have contaminant species comprising one chain rather than the other.

In certain embodiments, the method comprises transfecting the at least one mammalian cell with a multi-cistronic vector comprising said first, second and third DNA sequence. In certain embodiments, the at least one mammalian cell is selected from the group consisting of a VERO, Hela, HEK, NSO, Chinese Hamster Ovary (CHO), W138, BHK, COS-7, Caco-2 and MOCK cell, and subclasses and variants thereof.

Provided herein is a method of producing a glycosylated asymmetric antibody in stable mammalian cells, comprising: transfecting at least one stable mammalian cell with a first DNA sequence encoding a first heavy chain polypeptide, a second DNA sequence encoding a second heavy chain polypeptide different from the first heavy chain polypeptide, and a third DNA sequence encoding a light chain polypeptide, such that the said first, second and third DNA sequences are transfected in said mammalian cell in a pre-determined ratio; translating the first, second and third DNA sequences in the at least one mammalian cell such that said heavy and light chain polypeptides are expressed as the desired glycosylated asymmetric antibody in the at least one stable mammalian cell; and identifying and purifying the desired glycosylated asymmetric antibody. In certain embodiments, the identification is by a standard protein analytical technique. In certain embodiments, the standard protein analytical technique is one or more of SDS-PAGE, liquid chromatography, mass spectrometry and combinations thereof.

Provided herein is a method of producing a glycosylated asymmetric antibody in stable mammalian cells, comprising: transfecting at least one stable mammalian cell with a first DNA sequence encoding a first heavy chain polypeptide; a second DNA sequence encoding a second heavy chain polypeptide different from the first heavy chain polypeptide; and a third DNA sequence encoding a light chain polypeptide, such that the said first, second and third DNA sequences are transfected in the mammalian cell in a pre-determined ratio; translating the first, second and third DNA sequences in the at least one mammalian cell such that the heavy and light chain polypeptides are expressed as the desired glycosylated asymmetric antibody in the at least one stable mammalian cell; and wherein the expression product of the at least one mammalian cell comprises a larger percentage of the desired glycosylated asymmetric antibody as compared to the monomeric heavy or light chain polypeptides, or other antibodies. In certain embodiments, the expression product of the at least one stable mammalian cell comprises a greater percentage of the glycosylated asymmetric antibody compared to symmetric antibodies. In certain embodiments, the expression product comprises a greater than two fold excess of the asymmetric antibodies compared to the symmetric antibodies.

Provided herein is a method of producing a glycosylated asymmetric antibody in transient pool of mammalian cells, comprising: transfecting at least one mammalian cell pool with a first DNA sequence encoding a first heavy chain polypeptide, a second DNA sequence encoding a second heavy chain polypeptide different from the first heavy chain polypeptide, and a third DNA sequence encoding a light chain polypeptide, such that the said first, second and third DNA sequences are transfected in said mammalian cell in a pre-determined ratio; translating the first, second and third DNA sequences in the at least one mammalian cell pool such that said heavy and light chain polypeptides are transiently expressed as the desired glycosylated asymmetric antibody in the at least one mammalian cell pool; and identifying and purifying the desired glycosylated asymmetric antibody. In certain embodiments, the identification is by a standard protein analytical technique. In certain embodiments, the standard protein analytical technique is one or more of SDS-PAGE, liquid chromatography, mass spectrometry and combinations thereof.

Provided herein is a method of producing a glycosylated heteromultimer in a stable mammalian cell-line, comprising: transfecting at least one stable mammalian cell with: a first DNA sequence encoding at least a first immunoglobulin heavy chain polypeptide, and a second DNA sequence encoding at least a second immunoglobulin heavy chain polypeptide different from the first heavy chain polypeptide; such that said first and second DNA sequences are transfected in the mammalian cell in a pre-determined ratio; and translating the first and the second DNA sequences in the mammalian cell such that the immunoglobulin heavy chain polypeptides are expressed as the desired glycosylated heteromultimer in the stable mammalian cell-line.

Provided herein is a method of producing a heteromultimer in stable mammalian cells, comprising: transfecting at least one stable mammalian cell with: a first DNA sequence encoding at least a first immunoglobulin heavy chain polypeptide; and a second DNA sequence encoding at least a second immunoglobulin heavy chain polypeptide different from the first heavy chain polypeptide such that the first and second DNA sequences are transfected in said mammalian cell in a pre-determined ratio; and translating the first and second DNA sequences in the mammalian cell such that the immunoglobulin heavy chain polypeptides are expressed as the desired heteromultimer in the transformed at least one mammalian cell. In certain embodiments, at least one of the first and second DNA sequences also encodes one or more of a single-chain Fv segment and a single-chain Fab segment. In certain embodiments, the method of producing a heteromultimer in stable mammalian cells comprises identifying and purifying the desired heteromultimer. In some embodiments, the identification is by one or both of liquid chromatography and mass spectrometry.

In certain embodiments, the predetermined ratio of the first DNA sequence:second DNA sequence is such that amount of translated first immunoglobulin heavy chain polypeptide is about equal to the amount of translated second immunoglobulin heavy chain polypeptide. In certain embodiments, where the first heavy chain polypeptide and the second heavy chain polypeptide are produced in the mammalian cell at different levels, for example due to differing levels of transcriptional, translational, processing, or secretory efficiencies, the predetermined ratio of said first DNA sequence:second DNA sequence is such that the amount of translated first immunoglobulin heavy chain polypeptide is less than the amount of translated second immunoglobulin heavy chain polypeptide. Thus, in a related embodiment, the predetermined ratio of said first DNA sequence:second DNA sequence is such that the amount of translated second immunoglobulin heavy chain polypeptide is less than the amount of DNA that encodes first immunoglobulin heavy chain polypeptide. In certain embodiments, such altered expression levels resulting in one chain being expressed more than the other is useful when it is acceptable or preferable to have contaminant species comprising one chain rather than the other.

In certain embodiments described herein, the mammalian cell is selected from the group consisting of a VERO, Hela, Chinese Hamster Ovary (CHO), W138, BHK, COS-7, Caco-2 and MOCK cell, and subclasses and variants thereof. In certain embodiments, the method comprises producing said heteromultimer in a pool of mammalian cells, each cell transfected with said first, and second DNA sequence.

Provided herein is a method of screening mammalian cell-lines to produce a substantially pure glycosylated asymmetric antibody, said method comprising: transfecting mammalian cells with different ratios of a first DNA sequence encoding a first heavy chain polypeptide; a second DNA sequence encoding a second heavy chain polypeptide different from the first heavy chain polypeptide; and a third DNA sequence encoding a light chain polypeptide; expressing said first, second and third DNA sequences in the mammalian cell such that the heavy and light chain polypeptides are expressed as the desired glycosylated asymmetric antibody in the transformed mammalian cell; determining the purity of desired glycosylated asymmetric antibody expressed by the different cells; identifying and isolating the mammalian cell which expresses the desired glycosylated asymmetric antibody with maximum purity, thereby identifying the optimum ratio of the first DNA sequence:second DNA sequence:third DNA sequence for transfecting the mammalian cell type. In certain embodiments the purity is determined by one or more of the typical protein analytical techniques, including but not limited to SDS-PAGE, capillary electrophoresis, liquid chromatography or mass spectrometry. In some embodiments, the purity is determined by ion exchange chromatography or by gel isolation. In some embodiments, the mammalian cell-line is selected from the group consisting of a VERO, Hela, HEK, NSO, Chinese Hamster Ovary (CHO), W138, BHK, COS-7 Caco-2, MOCK cell and subclasses and variants thereof.

Further Purification:

In some embodiments, it may be necessary to purify the glycosylated asymmetric antibodies and the heteromultimers obtained by the methods described herein from contaminating cell proteins or polypeptides to obtain preparations that are substantially homogeneous. As a first step, the culture medium or lysate is normally centrifuged to remove particulate cell debris.

Proteins and polypeptides having antibody constant domains can be conveniently purified by hydroxylapatite chromatography, gel electrophoresis, dialysis, or affinity chromatography, such as protein A affinity chromatography. The Bakerbond ABX™ resin (J. T. Baker, Phillipsburg, N.J.), fractionation on an ion-exchange column, ethanol precipitation, reverse phase HPLC, chromatography on silica, chromatography on heparin Sepharose, chromatography on an anion or cation exchange resin (such as a polyaspartic acid column), chromatofocusing, SDS-PAGE, and ammonium sulfate precipitation are various options for further purification of the protein. Protein A as an affinity ligand can be used to purify the heteromultimers and glycosylated asymmetric antibody constructs obtained by methods described herein. The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. The conditions for binding a heteromultimers and glycosylated asymmetric antibody to the protein A affinity column are dictated entirely by the characteristics of the Fe domain; that is, its species and isotype. Generally, when the proper ligand is chosen, efficient binding occurs directly from unconditioned culture fluid. This affinity chromatography step can result in a heteromultimer or glycosylated asymmetric antibody preparation that is >95% pure.

Terms understood by those in the art of antibody technology are each given the meaning acquired in the art, unless expressly defined differently herein. Antibodies are known to have variable regions, a hinge region, and constant domains. Immunoglobulin structure and function are reviewed, for example, in Harlow et al, Eds., Antibodies: A Laboratory Manual, Chapter 14 (Cold Spring Harbor Laboratory, Cold Spring Harbor, 1988).

The process or method of the present invention comprises the steps of transfecting at least one mammalian cell with an asymmetric antibody construct encoding the asymmetric antibody described herein, and culturing the transfected cells to produce an expression product comprising greater than 75% asymmetric antibody product, less than 10% monomers, and undetectable amounts of homodimers of said first or second heavy chain polypeptide. The asymmetric antibody construct may encode the asymmetric antibody product where each nucleic acid encoding one polypeptide of the asymmetric antibody product is present in separate expression vectors, or where all of the nucleic acids encoding the polypeptides of the asymmetric antibody product are in a single multi-cistronic expression vector. In one embodiment, the nucleic acid sequences encoding the polypeptides of the asymmetric antibody product in a multi-cistronic expression vector are expressed under the control of separate promoters. The expression product can be further purified using standard downstream processing typical for purification of a therapeutic antibody.

An overview of an exemplary process or method of the invention is shown in FIG. 21. This figure relates to an embodiment where the asymmetric antibody product to be produced comprises two heavy chain polypeptides and one light chain polypeptide, and where the step of determining the predetermined or optimal ratios of these chains is carried out in a transient transfection system followed by generation of stable pools of mammalian cells using predetermined ratios of the heavy and light polypeptide chains. It is contemplated, however, that variations on these parameters are possible according to the invention, as described herein. Another exemplary process or method for developing a stable mammalian cell expressing the asymmetric antibody of interest is shown in FIG. 22.

In general, the method provides an expression product comprising a high titer of asymmetric antibody product. In one embodiment, the asymmetric antibody product is present in concentration of at least 20 mg/L. In another embodiment, the asymmetric antibody product is present in a concentration of at least 50 mg/L. In another embodiment, the asymmetric antibody product is present in a concentration of at least 100 mg/L. In another embodiment, the asymmetric antibody product is present in a concentration of at least 200 mg/L. In another embodiment, the asymmetric antibody product is present in a concentration of at least 500 mg/L. In another embodiment, the asymmetric antibody product is present in a concentration of at least 900 mg/L. In one embodiment, expression of the asymmetric antibody product is greater than 900 mg/L prior to feed and upstream process optimization. This is comparable to what can be achieved for a conventional mAb at this stage of process development.

The process or method is an efficient one for producing stable mammalian cells producing the asymmetric antibody of interest. In one embodiment, the process or method allows for a frequency of mammalian cell expressing the asymmetric antibody of interest of at least one in 500. In one embodiment, the process or method allows for a frequency of mammalian cell expressing the asymmetric antibody of interest of at least one in 200. In one embodiment, the process or method allows for a frequency of mammalian cell expressing the asymmetric antibody of interest of at least one in 100. In one embodiment, the process or method allows for a frequency of mammalian cell expressing the asymmetric antibody of interest of at least one in 50. In one embodiment, the process or method allows for a frequency of mammalian cell expressing the asymmetric antibody of interest of at least one in 25. In one embodiment, the process or method allows for a frequency of mammalian cell expressing the asymmetric antibody of interest of at least one in 20.

The process or method is amenable to large-scale production of asymmetric antibodies with high titer and purity in mammalian cells. In one embodiment, the process is carried out in CHO cells. In one embodiment, the transfected mammalian cells are cultured in suspension.

In one embodiment, the process comprises the steps of transfecting a number of mammalian cell pools with an asymmetric antibody construct encoding the asymmetric antibody described herein, and culturing the transfected cells to produce an expression product comprising greater than 75% asymmetric antibody product, less than 10% monomers, and undetectable amounts of homodimers; generating a number of stable cell pools expressing the expression product, expanding the stable cell pools, and analyzing the expression product of the stable cell pools to select a number of cell pools that express the asymmetric antibody product, and selecting a monoclonal cell line from the cell pools based on the yield and purity of the asymmetric antibody in the monoclonal cell line.

4.1 Asymmetric Antibodies

Typically, antibodies such as the lgG (immunoglobulin G) are heteromultimers comprising of two identical heavy chains and two identical light chains. The typical lgG antibody is also referred to as symmetric antibody since the two copies of the heavy chains comprise the same amino acid sequence. Each heavy chain is paired to a light chain, and the two heavy chains themselves pair up in the symmetric structure.

The heavy chain in the context of a typical human lgG comprises VH, CH1, hinge, CH2 and CH3 domains from the N to C-terminus of the polypeptide. The typical human lgG antibody comprises two copies of the heavy chain pairing to form homodimer via interactions across the two CH3 domains, interactions across the carbohydrates in the glycosylation on the CH2 domains and disulfide bonds across the hinge. The paired CH2 and CH3 domain in a typical antibody is referred to as the Fe or Fe region and is homodimeric in nature. In some embodiments, engineered heavy chains might lack one or more of VH, CH 1, hinge or CH2 domains and could also have other protein domains.

An asymmetric antibody refers to a structure with a "Y" like configuration comprising at least two different heavy chains. The two different heavy chains in an asymmetric antibody form a heterodimeric Fc. The asymmetric antibody could comprise of two light chains of the same amino acid sequence (configuration also referred to as common light chain) or could comprise of two different light chains with different amino acid sequence. Alternately, the asymmetric antibody may comprise of only one light chain or may be devoid of any light chain.

Amino acid modifications can be introduced in the CH3 domain interface such that two different heavy chains (A and B) selectively and preferentially pair to form heterodimers (AB). Depending on the nature of the amino acid modification, the protein product could be homogeneous in heterodimer (AB) or comprise of a heterogeneous mixtures of the heterodimer (AB) with homodimer (AA or BB) or monomer (A or B). In some context, the monomeric species is also referred to as half-antibodies. A homogeneous protein product comprising largely of the heterodimer (AB) is also referred to as a pure heterodimeric product. The presence of the homodimers and/or monomers along with the heterodimer makes the product heterogeneous. The homodimer and monomer in the protein product is referred to here as contaminants. It is further contemplated that expression products may not only contain homodimer and monomer contaminants, but additional contaminants such as lysine or glycine truncated variants.

Heterodimer Fc here refers to the two-paired heavy chains forming an Fc domain in an asymmetric antibody or alternately as Fc domain fusion proteins. One could obtain heterodimeric Fc fusion proteins by genetically fusing other proteins or peptides of interest to one or more of the N or C terminus of the two chains in the heterodimeric Fc. The proteins or peptides of interest being fused to the Fc could be, but are not limited to, single domain antibodies such as the human VH domain, camelids, scFv's, other single chain or single domain antigen binding protein modules such as fibronectin derived protein domains, ankyrin repeat protein derived domains etc, cytokines, receptors or ligands.

Amino acid modifications utilized to generate an asymmetric antibody include, but are not limited to, amino acid insertions, deletions, substitutions, and rearrangements. As used herein, asymmetric amino acid modifications are any modification wherein an amino acid at a specific position on one polypeptide is different from the amino acid on the second polypeptide at the same position. This can be a result of modification of only one of the two amino acids or modification of both amino acids to two different amino acids from the first and second polypeptide.

The process described herein relates to the production of asymmetric antibodies (asymmetric antibody products) that are encoded by asymmetric antibody constructs. The asymmetric antibodies to be produced are derived from lgG molecules.

Naturally occurring lgG antibodies or monoclonal antibodies (mAbs) are symmetric molecules composed of two equivalent heavy and two light polypeptide chains, each comprising multiple immunoglobulin (lg) structural domains. The lgG class of mAbs exists in one of four isoforms, lgG1, lgG2, lgG3, or lgG4. In one embodiment, the asymmetric antibodies are derived from lgG1, lgG2, lgG3, or lgG4 isotypes of lgG. In one embodiment, the asymmetric antibodies are derived from lgG1, lgG2, or lgG4 isotypes of lgG. In one embodiment, the asymmetric antibodies are derived from the lgG1 isotype of lgG. In one embodiment, the asymmetric antibodies are derived from the lgG2 isotype of lgG. In one embodiment, the asymmetric antibodies are derived from the lgG4 isotype of lgG. In one embodiment, the asymmetric antibody may be derived from an lgA antibody.

The heavy chain is composed of four domains (VH, CH1, CH2 and CH3) and the light chain of two (VL and CL) immunoglobulin (lg) domains, respectively. The VH and CH1 domains from each of the heavy chains combine with the VL and CL domains of light chain to form the two Fab ("fragment antigen binding") arms of the mAb. Thus, naturally occurring antibodies have two antigen-binding domains each binding to the same epitope on the same antigen.

The CH3 and CH2 domains of the two heavy chains interact via protein-protein contacts across the CH3 domains and glycosylation in the CH2 domains to form the homodimeric Fc ("fragment crystallizable") region. The linker region between CH1 and CH2 domains of the antibody constitutes the hinge region of the antibody molecule. Apart from connecting the Fab and Fc regions of the mAb, the hinge also maintains disulphide links across the two heavy chains and holds them together. The number of amino acids and disulphide links in the hinge region is notably different among the four isotypes of lgG. The glycosylation pattern in lgG molecules can be significantly diverse, about 30 different carbohydrate moieties have been observed in lgG molecules [Arnold J. N.; Wormald M. R.; Sim R. B.; Rudd P. M. and Dwek R. A. (2007) Annual Reviews of Immunology 25, 21-50].

Bi-specific antibodies, or asymmetric antibodies have been engineered such that each of the two antigen-binding domains binds to different epitopes. Several approaches have been taken to engineer bi-specific antibodies, including the generation of heterodimeric heavy chain polypeptides using the knob-into-holes (KiH) approach (see for example, International Patent Publication No. WO 96/027011, U.S. Pat. Nos. 5,821,333, and 7,695,936) or alternatively, the approach described in International Patent Publication No. WO 2012/058768. Additional methods for modifying Fc polypeptides to promote heterodimeric Fc formation are described in Gunasekaran et al. (Gunasekaran K. et al. (2010) J Biol Chem. 285, 19637-46, electrostatic design to achieve selective heterodimerization), in Davis et at. (Davis, J H. et al. (2010) Prot Eng Des Sel; 23(4): 195-202, strand exchange engineered domain (SEED) technology), and in Moore et al (2011) Mabs 3:6, 546-557.

Asymmetric antibodies that can be produced using the process according to the invention comprise two different immunoglobulin heavy chains, a first heavy chain polypeptide and a second heavy chain polypeptide, and exhibit the following features: i) a variant CH3 domain with amino acid mutations that promote the formation of a heterodimeric Fc region; ii) heavy chains that preferentially exist as stable monomers (half-antibodies) over homodimers when not present in heterodimeric form, and iii) have at least one antigen-binding domain.

In one embodiment, the asymmetric antibody antibodies comprise a variant CH3 domain that has a Tm greater than about 75° C. In another embodiment, the asymmetric antibody antibodies comprise a variant CH3 domain that has a Tm greater than about 80° C.

In one embodiment, the asymmetric antibody comprises a CH2 domain that retains wild-type stability.

First and Second Heavy Chain Polypeptides

Asymmetric antibodies comprise a first heavy chain polypeptide and a second heavy chain polypeptide, as indicated above. The term "first heavy chain polypeptide" and "second heavy chain polypeptide" can be used interchangeably provided that each asymmetric antibody comprises one first heavy chain polypeptide and one second heavy chain polypeptide. First heavy chain polypeptide and second heavy polypeptide are also referred to elsewhere herein as "Chain A" or "HC1", and "Chain B" or "HC2." The first and second heavy chain polypeptides comprise mutations in the CH3 domain that promote the formation of a heterodimeric Fc region. The heavy chains can be full-length heavy chains, comprising a Fab region and an Fc region comprising a variant CH3 domain, or they can be fragments or variants of full-length heavy chains comprising at least a CH3 domain. By full-length heavy chain is meant a heavy chain comprised of the VH, CH1, hinge, CH2 and CH3 domain from the N to C terminus. The VH and CH 1 domains pair with the VL and CL domains of the light chain to form the Fab.

Thus in one embodiment, the asymmetric antibody comprises two full-length heavy chains comprising a variant CH3 domain. In another embodiment, the asymmetric antibody comprises one full-length heavy chain and one fragment of a heavy chain wherein the asymmetric antibody comprises a variant CH3 domain, a CH2 domain and a hinge region. In another embodiment, the asymmetric antibody comprises a first heavy chain that is a fragment of a heavy chain that is fused to an antigen-binding domain sequence, and a second heavy chain that is a fragment of a heavy chain, wherein the asymmetric antibody comprises a variant CH3 domain. In a related embodiment, the antigen-binding domain comprises camelid VHH domain, a human Vh domain, an scFv, a single chain Fab, or a peptide or protein other than those present in a typical antibody such as the IgG.

In another embodiment, the asymmetric antibody comprises a first full-length heavy chain polypeptide with a first Fab region and a second full-length heavy chain polypeptide with a second Fab region, wherein the asymmetric antibody comprises a variant CH3 domain.

In another embodiment, the first heavy chain polypeptide and the second heavy chain polypeptide of the asymmetric antibody are limited to only the CH3 domains from the typical antibody heavy chain. In other embodiments, the heavy chain of the asymmetric antibody comprises a domain other than the VH, CH1 and CH2 domains.

It is further contemplated that in some embodiments, that at least one of the first heavy chain and the second heavy chain is a hybrid heavy chain polypeptide comprising at least a variant CH3 domain, a CH2 domain and a hinge region, as well as at least one single-chain Fv (scFv) sequence, a single chain Fab sequence, or a single domain antibody sequence. In one embodiment, both the first heavy chain polypeptide and the second heavy chain polypeptide are hybrid heavy chain polypeptides.

Variant CH3 Domain Pairs

As indicated above, the asymmetric antibody comprises a variant CH3 domain pair that has been modified to promote the formation of a heterodimeric Fc region and wherein the first and second heavy chain polypeptides comprising the variant CH3 domain pair, preferentially exists as monomers rather than homodimers when not in the form of a heterodimer pair. Each variant CH3 domain pair is comprised of two heavy chain CH3 domain sequences, one from each heavy chain polypeptide, wherein each heavy chain CH3 domain sequence comprises amino acid modifications that promote the formation of a heterodimeric Fc region. Suitable variant CH3 domains are known in the art and include, for example, those described in International Patent Publication Nos. WO 2012/058768, and WO 2013/063702 as long as they exhibit the features of the asymmetric antibody as described herein. In one embodiment, the asymmetric antibody comprises a variant CH3 domain pair where the CH3 domain sequence of the first heavy chain polypeptide comprises the amino acid modifications T366L, N390R, K392R, and T394W and the CH3 domain sequence of the second heavy chain polypeptide comprises the amino acid modifications L351Y, S400E, F405A, and Y407V. In one embodiment, the asymmetric antibody comprises a variant CH3 domain pair where the CH3 domain sequence of the first heavy chain polypeptide comprises the amino acid modifications T350V, L351Y, F405A, and Y407V and the CH3 domain sequence of the second heavy chain polypeptide comprises the amino acid modifications T350V, T366L, K392L, and T394W. In one embodiment, the asymmetric antibody comprises a variant CH3 domain pair where the variant CH3 sequence of the first heavy chain polypeptide comprises the amino acid modifications L351Y, F405A, and Y407V, and the variant CH3 sequence of the second heavy chain polypeptide comprises the amino acid modifications T366L, K392M, and T394W. In another embodiment, the asymmetric antibody comprises a variant CH3 domain pair where the variant CH3 sequence of the first heavy chain polypeptide comprises the amino acid modifications L351Y, F405A, and Y407V, and the variant CH3 sequence of the second heavy chain polypeptide comprises the amino acid modifications T366L, K392L, and T394W. In another embodiment, the asymmetric antibody comprises a variant CH3 domain pair where the variant CH3 sequence of the first heavy chain polypeptide comprises the amino acid modifications T350V, L351Y, F405A, and Y407V, and the variant CH3 sequence of the second heavy chain polypeptide comprises the amino acid modifications T350V, T366L, K392M, and T394W. In another embodiment, the asymmetric antibody comprises a variant CH3 domain pair where the variant CH3 sequence of the first heavy chain polypeptide comprises the amino acid modifications T350V, L351Y, F405A, and Y407V, and the variant CH3 sequence of the second heavy chain polypeptide comprises the amino acid modifications T350V, T366L, K392L, and T394W.

In an additional embodiment, the asymmetric antibody comprises a variant CH3 domain pair where the CH3 domain sequence of the first heavy chain polypeptide comprises the amino acid modifications T366L, N390R, K392R, and T394W and the CH3 domain sequence of the second heavy chain polypeptide comprises the amino acid modifications L351Y, S400E, F405A, and Y407V, and either the first heavy chain polypeptide or the second heavy chain polypeptide additionally comprises the amino acid modification T350V. In one embodiment, the asymmetric antibody comprises a variant CH3 domain pair where the variant CH3 sequence of the first heavy chain polypeptide comprises the amino acid modifications L351Y, F405A, and Y407V, and the variant CH3 sequence of the second heavy chain polypeptide comprises the amino acid modifications T366L, K392M, and T394W, and either the first heavy chain polypeptide or the second heavy chain polypeptide additionally comprises the amino acid modification T350V. In another embodiment, the asymmetric antibody comprises a variant CH3 domain pair where the variant CH3 sequence of the first heavy chain polypeptide comprises the amino acid modifications L351Y, F405A, and Y407V, and the variant CH3 sequence of the second heavy chain polypeptide comprises the amino acid modifications T366L, K392L, and T394W, and either the first heavy chain polypeptide or the second heavy chain polypeptide additionally comprises the amino acid modification T350V.

Heavy Chains Preferentially Existing as Stable Monomers Over Homodimers

As indicated above, the asymmetric antibody that can be purified according to the method described herein comprises heavy chains that preferentially exist as stable monomers or half-antibodies, when not present in the heterodimeric form. The heavy chain polypeptides employed in the formation of an asymmetric antibody comprise two variant CH3 domains which selectively pair to form a CH3 domain pair in an heterodimeric Fc. Typically, equimolar amounts of the two heavy chain polypeptides are required in the formation of the heterodimeric Fc.

In some variant CH3 designs, one or both of the heavy chains might exist in equilibrium between heterodimeric and homodimeric forms. Given the similarity in size and other physicochemical properties of the heterodimeric and homodimeric forms it is difficult to separate and purify the desired heterodimeric species from the homodimeric species. In the presence of an excess of one of the two heavy chains, the excess heavy chain could pair to form a homodimer or exist as monomers (also referred to as half antibodies). Certain variant CH3 designs preferentially exist as stable monomers rather than forming homodimers while in other designs the homodimer might be the preferred stable state. Separation of heterodimers from monomers is more readily achieved using methods known in the art, such as, for example, ion exchange chromatography.

Thus in one embodiment, the first and second heavy chain polypeptides of the asymmetric antibody preferentially exist as monomers rather than homodimers when not in the form of a heterodimer pair. In one embodiment, the first heavy chain polypeptide of the asymmetric antibody exists at greater than 50% monomer at equilibrium with less than 50% of homodimers. In one embodiment, the first heavy chain polypeptide of the asymmetric antibody exists at greater than 70% monomer at equilibrium with less than 30% of homodimers. In one embodiment, the first heavy chain polypeptide of the asymmetric antibody exists at greater than 90% monomer at equilibrium with less than 10% of homodimers. In one embodiment, the first heavy chain polypeptide of the asymmetric antibody exists at greater than 98% monomer at equilibrium with less than 2% of homodimers. In one embodiment, the second heavy chain polypeptide of the asymmetric antibody exists at greater than 50% monomer at equilibrium with less than 50% of homodimers. In one embodiment, the second heavy chain polypeptide of the asymmetric antibody exists at greater than 70% monomer at equilibrium with less than 30% of homodimers. In one embodiment, the second heavy chain polypeptide of the asymmetric antibody exists at greater than 90% monomer at equilibrium with less than 10% of homodimers. In one embodiment, the second heavy chain polypeptide of the asymmetric antibody exists at greater than 98% monomer at equilibrium with less than 2% of homodimers.

Assessment of the amount of monomer and homodimer formed in the expression product can be assessed as follows. Purification of the expression product using a protein A affinity chromatography technique from a transient or stable cell producing the asymmetric antibody allows separation of protein molecules comprising the Fc region of the antibody from rest of the protein products. The Fc region containing protein component includes the expected asymmetric (heterodimeric) antibody product, one or two of the homodimeric species and one or both of the monomeric species. This can be characterized using a number of standard protein characterization techniques such as SDS-PAGE, capillary electrophoresis, gel chromatography, liquid chromatography and mass spectroscopy. As noted earlier, given the difference in complexity of separating the preferred heterodimeric product from the contaminant homodimer or the contaminant monomer, a CH3 variant design that preferentially exists as the monomer is easier to develop.

Stability of the Asymmetric Antibody

The thermal stability of the asymmetric antibody can be determined according to methods known in the art. The melting temperature of the IgG Fc region construct is indicative of its thermal stability. The melting point of the IgG Fc region construct may be measured using techniques such as differential scanning calorimetry (DSC) (Chen et al (2003) Pharm Res 20:1952-60; Ghirlando et al (1999) Immunol Lett 68:47-52). Alternatively, the thermal stability of the IgG Fc region construct may be measured using circular dichroism (Murray et al. (2002) J. Chromatogr Sci 40:343-9).

The methodology for determining the Tm of the CH2 domain is well described in the art (see for example Ionescu et al (2008) J Pharm Sci 97(4):1414-26). In short, melting of the Fc region of IgG1 produces two transitions: one for the melting of the CH2 domain and one for that of the CH3 domain. These transitions are independent of the Fab present, but can be masked by the Fab transition. Typically, melting of IgG1 Fc gives a transition with a Tm of about 71° C. for the CH2 domain and another transition with a Tm of about 82° C. for the CH3 domain. The Tm of the CH2 domain is affected by its glycosylation state, the nature of the hinge region, and the intrinsic stability of the CH3 domain. Aglycosylation and deglycosylation are known to decrease the Tm of the CH2 domain by 10° C. Removal of hinge disulfides are also known to decrease the Tm of the CH2 domain by more about 10° C. Changes to the CH3 domain that decrease its stability below that of the CH2 domain are likely to produce changes in the Tm of the CH2 domain, but the effect is harder to predict. In one embodiment, the CH2 domain of the asymmetric antibody has a Tm of greater than 70° C. Many of the engineered CH3 domains designed to form heterodimeric Fc tend to show reduced stability relative to wild type IgG Fc as observed in DSC experiments (U.S. Pat. No. 5,731,168; U.S. Pat. No. 5,821,333; U.S. Pat. No. 5,807,706; U.S. Pat. No. 7,183,076; U.S. Pat. No. 7,642,228; U.S. Pat. No. 7,695,936; US20100286374; US20070287170). On the other hand, some of the engineered CH3 domain mutations forming heterodimeric Fc are known to have stability of greater than 78° C. (see for example, US Patent Publication No. 2012/0149876).

Antigen-Binding Domains of the Asymmetric Antibody

As indicated above, the asymmetric antibody to be produced according to the process of the invention comprises at least one antigen-binding domain. Thus in one embodiment, the asymmetric antibody to be expressed is a mono-specific, monovalent antibody comprising one antigen-binding domain. In another embodiment, the asymmetric antibody to be expressed is a bivalent antibody comprising at least two antigen-binding domains. In embodiments where the asymmetric antibody to be expressed is a mono-specific bivalent antibody, the asymmetric antibody comprises at least two antigen-binding domains, both antigen-binding domains recognizing the same epitope on a target antigen. In another embodiment where the asymmetric antibody to be expressed is a bi-specific bivalent antibody, the asymmetric antibody comprises at least two antigen-binding domains, each antigen-binding domain binding to a different epitope on the same target antigen. In another embodiment where the asymmetric antibody to be expressed is a bi-specific bivalent antibody, the asymmetric antibody comprises at least two antigen-binding domains, each antigen-binding domain binding to an epitope on a different target antigen. In one embodiment, each antigen-binding domain is composed of two protein chains such as the Fab. In some embodiments, each antigen-binding domain comprises a single protein chain but is composed of two or more protein domains such as a single chain Fv (scFv) and single chain Fab (scFab).

The format of the antigen-binding domain of the asymmetric antibodies is selected from Fab domains, scFvs and combinations thereof. For example, in one embodiment, at least one antigen-binding domain of the asymmetric antibody is a Fab domain comprising a VH sequence and CH1 sequence of a heavy chain, paired with a VL sequence and CL sequence of a light chain. In another embodiment, at least one antigen-binding domain of the asymmetric antibody is a single-chain variable domain (scFv). In one embodiment where the asymmetric antibody comprises two antigen-binding domains, both antigen-binding domains of the asymmetric antibody are scFvs. In other embodiments where the asymmetric antibody comprises two antigen-binding domains, both antigen-binding domains of the asymmetric antibody are Fab domains. In still other embodiments where the asymmetric antibody comprises two antigenbinding domains, one antigen-binding domain is a Fab domain and the other antigen-binding domain is an scFv.

In one embodiment, at least one antigen-binding domain of the asymmetric antibody is a single domain antigen-binding domain. Examples of suitable single domain antigen-binding domains include those that are devoid of antibody light chains such as single domain antibodies (sdAb), autonomous or independently stable human variable heavy domains ($V_H$), camelid nanobodies ($V_hH$), or shark $V_{NAR}$. These single domain antigen-binding domains have been shown to exhibit properties such as the ability to bind to alternative or cryptic epitopes that may not be accessible by traditional Fab domains due to their size and structural conformation. In one embodiment, where the asymmetric antibody comprises two antigen-binding domains, one antigen-binding domain is a Fab domain and the other antigen-binding domain is a single domain antigen-binding domain. In another embodiment where the asymmetric antibody comprises two antigen-binding domains, one antigen-binding domain is an scFv and the other antigen-binding domain is a single domain antigen-binding domain. In another embodiment where the asymmetric antibody comprises two antigen-binding domains, one antigen-binding domain is in a single chain format and the other antigen-binding domain is in a single domain antigen-binding domain.

In another embodiment, the antigen binding domain is derived form a non-antibody source such as those from the fibronectin domains such as Adnectins, ankyrin repeat protein such as DARPins, other antigen binding peptides or ligands. In another embodiment, the antigen binding domain is a receptor protein ectodomain that is fused to the N or C-terminus of the Fc.

In another embodiment, the asymmetric antibody comprises one full-length heavy chain including a Fab region and one fragment of a heavy chain wherein the asymmetric antibody comprises a variant CH3 domain, a CH2 domain and a hinge region. In another embodiment, the asymmetric antibody comprises a first heavy chain that is a fragment of a heavy chain that is fused to an scFv, and a second heavy chain that is a fragment of a heavy chain, wherein the asymmetric antibody comprises a variant CH3 domain. In one embodiment, the scFv is fused to the N-terminus of the CH2 domain. In another embodiment, the asymmetric antibody comprises a first full-length heavy chain with a first Fab region and a second full-length heavy chain with a second Fab region, wherein the asymmetric antibody comprises a variant CH3 domain. In one embodiment, the first and second Fab region binds to the same antigen epitope. In another embodiment, the first and second Fab regions bind to different epitopes on the same or different antigens.

Further Modifications

It is further contemplated that the asymmetric antibodies that can be expressed according to the method described herein may comprise additional modifications that that provide features or characteristics that are beneficial in a therapeutic antibody. Such features or characteristics include modifications that i) either increase or decrease effector functions such as ADCC, ADCP, CDC; ii) altered pharmacokinetic properties of the antibody. Suitable modifications are described in the art and methods of designing and preparing such modified asymmetric antibodies are also described in the art.

In some embodiments, the CH2 domain comprises mutations. In some embodiments, the CH2 domain comprises mutations that alter its interactions with one or more of the Fc gamma receptors. In some embodiment, the heavy chain is glycosylated. In some embodiment, the heavy chain is aglycosylated and comprises a mutation at the N297 amino acid position of the CH2 domain. In some embodiments, the heavy chain sequence comprises mutations that alter the interaction of the asymmetric antibody with the FcRn receptor.

The asymmetric antibody products, may be chimeric or humanized antibodies. Methods for designing such antibody products are known in the art.

4.2 Process and Method

The process or method of the present invention comprises the steps of transfecting at least one mammalian cell with an asymmetric antibody construct encoding the asymmetric antibody described herein, and culturing the transfected cells to produce an expression product comprising greater than 75% asymmetric antibody product, less than 10% monomers, and undetectable amounts of homodimers of said first or second heavy chain polypeptide. The following describes various embodiments of the process or method with respect to the process or method, or the specific cells, expression vectors, expression products and analysis.

4.2.1 Selection of Mammalian Cell

The choice of cell for generation of a stable cell expressing the asymmetric antibody is based on the following criteria i) the desired characteristics for the asymmetric antibody product with respect to glycosylation and other post-translational modifications, ii) level of expression of heterologous proteins, ii) suitability for scale-up, iv) ability to grow in chemically defined and animal component-free media v) cell growth characteristics, vi) intracellular vs. extracellular expression, vi) biological activity of the protein of interest, and Vii) the ability to control these various properties, as well as regulatory issues and economic considerations. Additional information regarding the criteria for choosing the a cell line can be found in Strohl, W R and Strohl L M, "Cell line development" In Therapeutic Antibody Engineering, Cambridge: Woodhead Publishing (2012), pp 420-437). Suitable cell lines for the production of therapeutic antibodies are known in the art and include, for example, VERO cells, HeLa cells, HEK293 cells, NSO cells, Chinese Hamster Ovary (CHO) cells, W138 cells, BHK cells, COS-7 cells, Caco-2 cells and MOCK cells, and subclasses and variants thereof. In one embodiment the mammalian cell is a HEK293 cell. In one embodiment this cell line is grown under transient transfection conditions. In another embodiment the mammalian cell is a CHO cell. In one embodiment a stable cell line is generated from these CHO cells.

In one embodiment, the mammalian cell line is selected from the human cell lines Hela [ATCC CCL2] and 293 [ATCC CRL 1573] as well as 3T3 [ATCC CCL 163] and L cells, e.g. [ATCC CCL 149], (CHO) cells [ATCC CCL 61], BHK [ATCC CCL 10] cells as well as the CV 1 [ATCC CCL 70] and the COS cell lines [ATCC CRL 1650, CRL 1651].

In one embodiment, the mammalian cell selected is one that has been glycoengineered to reduce the fucosylation of expressed proteins by at least 5%. In one embodiment, the mammalian cell selected is one that has been glycoengineered to reduce the fucosylation of expressed proteins by at least 10%. In one embodiment, the mammalian cell selected is one that has been glycoengineered to reduce the fucosylation of expressed proteins by at least 15%.

In one embodiment, where a glycosylated asymmetric antibody product is desired, the mammalian cell line is selected from CHO and HEK293 cells. In some embodiments the expressed asymmetric antibody product has heterogenous glycosylation. In some embodiment the cell line is engineered to produce homogeneous glycosylation profile.

In some embodiment the asymmetric antibody is produced in a cell line that produces a homogenous C-terminal truncation product. In one embodiment the cell line is engineered to completely truncate the C-terminal Lys of the heavy chain.

In one embodiment, the asymmetric antibody is produced in a CHO cell or in a HEK293 cell. In one embodiment, the asymmetric antibody is produced using a commercially available mammalian cell expression system. Suitable such systems are known in the art and include, for example, SURE CHO-M Cell Line™ (Selexis Inc., San Francisco, USA), and GS Gene Expression System™ (Lonza, Walkersville, Md., USA) which is also a CHO cell-based system.

4.2.2 Nucleic Acid Constructs Encoding the Asymmetric Antibody

The constructs encoding the asymmetric antibody to be produced can be prepared according to methods known in the art. As is known in the art, nucleic acids encoding polypeptides include DNA sequences or RNA sequences, and it is contemplated that the nucleic acids encoding the polypeptides of the asymmetric antibody product can be either DNA or RNA. Thus, although the term "DNA sequence" is used throughout to describe embodiments of the invention, it should be understood that this term is meant to include RNA sequences as well, unless otherwise indicated.

Determining how to design nucleic acid constructs that encode the desired asymmetric antibody is well within the knowledge of a worker skilled in the art. As used herein, the term asymmetric antibody construct refers to one or more nucleic acid sequences that are required to encode the asymmetric antibody. For example, an asymmetric antibody that is a bi-specific, bivalent antibody comprising a common light chain and two antigen-binding domains that are Fab domains, can be encoded by an asymmetric antibody construct with a total of three DNA sequences: one DNA sequence encoding a first heavy chain polypeptide, and one DNA sequence encoding a second heavy chain polypeptide, and a third DNA sequence encoding the common light chain. As another example, in the case where the asymmetric antibody is a monovalent, mono-specific antibody, and the antigen-binding domain is a Fab domain, the asymmetric antibody can also be encoded by an asymmetric antibody construct with a total of three DNA sequences: one DNA sequence encoding a first heavy chain polypeptide that is a full length heavy chain polypeptide, a second DNA sequence encoding a second heavy chain polypeptide that comprises a hinge, CH2 and CH3 sequences, and a third DNA sequence encoding a light chain. As yet another example, in the case where the asymmetric antibody is a monovalent, mono-specific antibody, and the antigen-binding domain is an scFv, the asymmetric antibody can be encoded by an asymmetric antibody construct with a total of two DNA sequences: one DNA sequence encoding a first heavy chain polypeptide that comprises a hinge, CH2 and CH3 sequence fused to the scFv, and a second DNA sequence encoding a second heavy chain polypeptide that comprises a hinge, CH2 and CH3 sequence. The determination of the number and design of DNA constructs necessary to encode other exemplary asymmetric antibody formats is within the knowledge of a worker skilled in the art.

In one embodiment, the asymmetric antibody construct comprises one DNA sequence encoding a first heavy chain polypeptide, one DNA sequence encoding a second heavy chain polypeptide, and a third DNA sequence encoding a light chain polypeptide. In another embodiment, the asymmetric antibody construct comprises one DNA sequence encoding a first heavy chain polypeptide, one DNA sequence encoding a second heavy chain polypeptide, a third DNA sequence encoding a light chain polypeptide, and a fourth DNA sequence encoding a second light chain polypeptide. In another embodiment, the asymmetric antibody construct comprises one DNA sequence encoding a first heavy chain polypeptide, one DNA sequence encoding a second heavy chain polypeptide and one or both of the DNA sequences also encodes for an alternate antigen binding domain. The alternate antigen binding domain could be one from the set of scFv, scFab, autonomous and stable human VH domain, camelid and fibronectin derived domain.

4.2.3 Expression Vectors Comprising Asymmetric Antibody Constructs

Once the DNA sequences of the asymmetric antibody construct have been identified, they are cloned into a suitable expression vector for reproduction and expression in the selected mammalian cell.

The expression vector(s) containing the nucleic acid sequences of the asymmetric antibody construct to be expressed according to the process described herein may theoretically be prepared by conventional methods known in the art. In one embodiment, the expression vector is a multi-cistronic expression vector that expresses all of the nucleic acid sequences of the asymmetric antibody construct. In another embodiment, each nucleic acid sequence of the asymmetric antibody construct is expressed from a separate vector.

Expression vectors typically include the functional components of a vector, e.g. suitable promoters, enhancers, termination and polyadenylation signals, antibiotic resistance genes, selectable markers, replication starting points and splicing signals. Conventional cloning vectors may be used to produce them, e.g. plasmids, bacteriophages, phagemids, cosmids or viral vectors such as baculovirus, retroviruses, adenoviruses, adena-associated viruses and herpes simplex virus, as well as synthetic or artificial chromosomes or mini-chromosomes. The eukaryotic expression vectors typically also contain prokaryotic sequences such as, for example, replication origin and antibiotic resistance genes which allow replication and selection of the vector in bacteria. A number of eukaryotic expression vectors which contain multiple cloning sites for the introduction of a polynucleotide sequence are known and some may be obtained commercially from various companies such as Stratagene, La Jolla, Calif., USA; Invitrogen, Carlsbad, Calif., USA; Promega, Madison, Wis., USA or BD Biosciences Clontech, Palo Alto, Calif., USA.

The expression of the nucleic acid sequences of the asymmetric antibody construct within an expression vector may take place starting from one or more transcription units. The term transcription unit is defined as a region which contains at least one of the nucleic acid sequences of the asymmetric antibody construct to be expressed. In one embodiment, the nucleic acid sequences of the asymmetric antibody construct within a transcription unit are functionally linked to one another in such a way that nucleic acid sequences within such a unit are under the transcriptional control of the same promoter or promoter/enhancer. As a result of this transcriptional linking of nucleic acid sequences, more than one protein or product can be transcribed from a transcription unit and thus expressed. Each transcription unit contains the regulatory elements which are necessary for the transcription and translation of the nucleic acid sequences contained therein. Each transcription unit may contain the same or different regulatory elements. IRES (internal ribosome entry site) elements or introns may be used for the functional linking of the nucleic acid sequences within a transcription unit.

The expression vector may contain a single transcription unit for expressing the nucleic acid sequences of the asymmetric antibody construct of interest and selectable marker genes, for example. Alternatively, the nucleic acids of the asymmetric antibody construct may also be separated in two or more transcription units. Various combinations of the nucleic acid sequences of the asymmetric antibody construct within a transcription unit are possible. In another embodiment of the present invention more than one expression vector consisting of one, two or more transcription units may be inserted in a host cell by cotransfection or in successive transfections in any desired order. Any combination of regulatory elements and nucleic acid sequences on each vector can be selected provided that adequate expression of the transcription units is ensured. If necessary, other regulatory elements and genes, e.g. additional genes of interest or selectable markers, may be positioned on the expression vectors.

A typical expression vector for mammalian cells contains an efficient promoter element in order to produce a good transcription rate, the DNA sequence to be expressed and signals for an efficient termination and polyadenylation of the transcript. Additional elements which can be used are "enhancers" which promote intensified transcription and sequences which can bring about a longer half life of the mRNA. For the expression of nucleic acid sequences in which the endogenous sequence fragment coding for a signal peptide is missing, there can be used vectors which contain such suitable sequences which code for signal peptides of other known proteins.

The choice of expression vector is based on the selected mammalian cell line and/or on whether the cells are to be transiently transfected or stably transfected as well as other factors known in the art. For example, HEK293-T cells constitutively express the T antigen of simian virus 40 (SV40) and thus expression vectors that have an SV40 origin of replication can be used with these cells in order to generate high levels of expression product. Additional information with respect to criteria for selection of expression vector can be found in Tom, R., Bisson, L. and Durocher, Y. Transient expression in HEK293-EBNA1 cells. In M. Dyson and Y. Durocher, Editors. Methods Express Series—Expression Systems. Scion Publishing Ltd, Bloxham, Oxfordshire, UK, July 2007; Pham P L, Kamen A, Durocher Y. Large-scale transfection of mammalian cells for the fast production of recombinant protein. Mol Biotechnol. 2006 October; 34(2):225-37; and Valerie Le Foum Pierre-Aiain Girod, Montse Buceta, Alexandre Regamey, Nicolas Mermod CHO cell engineering to prevent polypeptide aggregation and improve therapeutic protein secretion. Metabolic Eng 2013).

Vectors used for transient expression of a particular DNA sequence in mammalian cells typically contain the replication source of the SV40 virus. In cells expressing the T-antigen of the virus (e.g. COS cells), these vectors are reproduced abundantly. In principle any transfectable mammalian cell line can be used for this purpose. Signals which can bring about a strong transcription are e.g. the early and late promoters of SV40, the promoter and enhancer of the "major immediate-early" gene of HCMV (human cytomegalovirus), the LTR's ("long terminal repeats") of retroviruses such as, for example, RSV, HIV and MMTV. Signals of cellular genes such as e.g. the promoters of the actin and collagenase genes can also be used.

Alternatively, however, stable cell lines which have the specific DNA sequence integrated into the genome (chromosome) can also be obtained. For this, the DNA sequence is cotransfected together with a selectable marker, e.g. neomycin, hygromycin, dihydrofolate reductase (DHFR) or hypoxanthin guanine phosphoribosyl transferase (HGPT). The DNA sequence stably incorporated in the chromosome can also be reproduced abundantly. A suitable selection marker for this is, for example, dihydrofolate reductase (DHFR). Mammalian cells (e.g. CHO cells), which contain no intact dhfr gene, are thereby incubated with increasing amounts of methotrexate after transfection has been effected. In this manner cell lines which contain more than a thousand copies of the desired DNA sequence can be obtained. Other systems currently in use are among others the glutamine synthetase (GS) system (Bebbington et al., 1992) and the histidinol driven selection system (Hartmann and Mulligan, 1988). These amplifiable markers are also selectable markers and can thus be used to select those cells that obtained the vector. DHFR and glutamine synthetase provide good results. In both cases selection usually occurs in the absence of the appropriate metabolite (hypoxanthine and thymidine in case of DHFR, glutamine in the case of GS), preventing growth of non-transformed cells. With amplifiable systems such as the DHFR system, expression of a recombinant protein can be increased by exposing the cells to certain agents promoting gene amplification such as antifolates (e.g. methotrexate (MTX)) in case of the DHFR system. A suitable inhibitor for GS promoting gene amplification is methionine sulphoximine (MSX). Exposure to MSX also results in gene amplification.

In one embodiment, each DNA sequence of the asymmetric antibody construct is cloned into a separate plasmid or expression vector. In another embodiment, all of the DNA sequences of the asymmetric antibody construct are cloned into a multi-cistronic vector. In one embodiment, mammalian cell is tranfected with a multi-cistronic vector comprising first, second and third DNA sequences of the asymmetric antibody construct.

4.2.4 Transient and Stable Transfections

The transfection of the eukaryotic host cells with the expression vectors is carried out by conventional methods. Suitable methods of transfection include for example liposome-mediated transfection, calcium phosphate coprecipitation, electroporation, polycation- (e.g. DEAE dextran)-mediated transfection, protoplast fusion, microinjection and viral infections. According to the method described herein, in one embodiment, stable transfection is carried out in which the constructs are either integrated into the genome of the host cell or an artificial chromosome/minichromosome, or are episomally contained in stable manner in the host cell. The transfection method which gives the optimum transfection frequency and expression of the heterologous gene in the host cell in question is preferred. By definition, every sequence or every gene inserted in a host cell is referred to as a "heterologous sequence" or "heterologous gene" in relation to the host cell. This applies even if the sequence to be introduced or the gene to be introduced is identical to an endogenous sequence or an endogenous gene of the host cell. For example, a hamster actin gene introduced into a hamster host cell is by definition a heterologous gene.

The transfection of suitable host cells can theoretically be carried out by two different methods. In one embodiment, nucleic acids of the asymmetric antibody construct may be accommodated in independent or multicistronic transcription units on a single plasmid with which the host cell is then transfected. This is intended to secure the stoichiometric representation of the genes after integration into the genome of the host cell. However, in the case of independent transcription units it must hereby be ensured that the mRNAs which encode the different polypeptides of the asymmetric antibody product display the same stability and transcriptional and translational efficiency. In another embodiment, expression of the nucleic acid sequences of the asymmetric antibody construct takes place within a multicistronic transcription unit by means of a single promoter and only one transcript is formed.

By using IRES elements, a highly efficient internal translation initiation of the genes is obtained in the second and subsequent cistrons. However, the expression rates for these cistrons are lower than that of the first cistron, the translation initiation of which, by means of a so-called "cap"-dependent pre-initiation complex, is substantially more efficient than IRES-dependent translation initiation. In order to achieve a truly equimolar expression of the cistrons, additional inter-cistronic elements may be introduced, for example, which ensure uniform expression rates in conjunction with the IRES elements. Alternatively, expression of cistrons may be driven by separate promoters which can vary in strength and hence differential expression of cistrons as defined by the predefined ratio can be achieved.

In one embodiment, the asymmetric antibody product is expressed by cotransfection, in which the nucleic acids of the asymmetric antibody construct are separately integrated in different expression vectors. This allows for selection of certain proportions of genes and gene products to one another can be selected, thereby balancing out any differences in the mRNA stability and in the efficiency of transcription and translation. In addition, the expression vectors are more stable because of their small size and are easier to handle both during cloning and during transfection.

In one embodiment of the invention, therefore, the host cells are additionally transfected, or cotransfected, with one or more vectors having genes which code for one or more other proteins of interest. The other vector or vectors used for the cotransfection code, for example, for the other protein or proteins of interest under the control of the same promoter, preferably under the control of the same promoter/enhancer combination, and for at least one selectable marker, e.g. dihydrofolate reductase.

In another particular embodiment of the invention the host cells are co-transfected with at least two eukaryotic expression vectors, at least one of the two vectors containing at least one gene which codes for at least the protein of interest, while the other vector contains one or more nucleic acids according to the invention in any combination, position and orientation, and optionally also codes for at least one gene of interest, and these nucleic acids according to the invention impart their transcription- or expression-enhancing activity to the genes of interest which are located on the other co-transfected vector, by co-integration with the other vector.

According to the invention the host cells are established, adapted and cultivated under serum-free conditions, optionally in media which are free from animal proteins/peptides. Examples of commercially obtainable media include Ham's F12 (Sigma, Deisenhofen, Del.), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, Calif., USA), CHO-S-SFMII (Invitrogen), serum-free CHO-Medium (Sigma) and protein-free CHO-Medium (Sigma). Each of these media may optionally be supplemented with various compounds, e.g. hormones and/or other growth factors (e.g. insulin, transferrin, epidermal growth factor, insulin-like growth factor), salts (e.g. sodium chloride, calcium, magnesium, phosphate), buffers (e.g. HEPES), nucleosides (e.g. adenosine, thymidine), glutamine, glucose or other equivalent nutrients, antibiotics and/or trace elements. Although serum-free media are preferred according to the invention, the host cells may also be cultivated using media which have been mixed with a suitable amount of serum. In order to select genetically modified cells which express one or more selectable marker genes, one or more selecting agents are added to the medium.

The term "selecting agent" refers to a substance which affects the growth or survival of host cells with a deficiency for the selectable marker gene in question. Within the scope of the present invention, geneticin (G418) is used as the medium additive for the selection of heterologous host cells which carry a wild-type or preferably a modified neomycin phosphotransferase gene. If the host cells are to be transfected with a number of expression vectors, e.g. if several genes of interest are to be separately introduced into the host cell, they generally have different selectable marker genes. Suitable selection systems are known in the art and include, for example, the commercially available SGE Tech I transfection system (Selexis Inc., San Francisco, USA), and GS Gene Expression System™ (Lonza, Walkersville, Md., USA).

A "selectable marker gene" is a gene which allows the specific selection of cells which contain this gene by the addition of a corresponding selecting agent to the cultivation medium. As an illustration, an antibiotic resistance gene may be used as a positive selectable marker. Only cells which have been transformed with this gene are able to grow in the presence of the corresponding antibiotic and thus be selected. Untransformed cells, on the other hand, are unable to grow or survive under these selection conditions. There are positive, negative and bifunctional selectable markers. Positive selectable markers permit the selection and hence enrichment of transformed cells by conferring resistance to the selecting agent or by compensating for a metabolic or catabolic defect in the host cell. By contrast, cells which have received the gene for the selectable marker can be selectively eliminated by negative selectable markers. An example of this is the thymidine kinase gene of the Herpes Simplex virus, the expression of which in cells with the simultaneous addition of acyclovir or gancyclovir leads to the elimination thereof. The selectable markers used in this invention, including the amplifiable selectable markers, include genetically modified mutants and variants, fragments, functional equivalents, derivatives, homologues and fusions with other proteins or peptides, provided that the selectable marker retains its selective qualities. Such derivatives display considerable homology in the amino acid sequence in the regions or domains which are deemed to be selective. The literature describes a large number of selectable marker genes including bifunctional (positive/negative) markers. Examples of selectable markers which are usually used in eukaryotic cells include the genes for aminoglycoside phosphotransferase (APH), hygromycine phosphostransferase (HYG), dihydrofolate reductase (DHFR), thymidine kinase (TK), glutamine synthetase, asparagin synthetase and genes which confer resistance to neomycin (G418), puromycin, histidinol D, bleomycin, phleomycin and zeocin.

Amplifiable Selectable Marker Gene:

In addition, the host cells according to the invention may optionally also be subjected to one or more gene amplification steps in which they are cultivated in the presence of a selecting agent which leads to amplification of an amplifiable selectable marker gene.

The prerequisite is that the host cells are additionally transfected with a gene which codes for an amplifiable selectable marker. It is conceivable for the gene which codes for an amplifiable selectable marker to be present on one of the expression vectors or to be introduced into the host cell by means of another vector.

The amplifiable selectable marker gene usually codes for an enzyme which is needed for the growth of eukaryotic cells under certain cultivation conditions. For example, the amplifiable selectable marker gene may code for dihydrofolate reductase (DHFR). In this case the gene is amplified if a host cell transfected therewith is cultivated in the presence of the selecting agent methotrexate (MTX).

The DHFR marker is particularly suitable for the selection and subsequent amplification when using DHFR-negative basic cells such as CHO-DG44 or CHO-DUKX, as these cells do not express endogenous DHFR and therefore do not grow in purine-free medium. Consequently, the DHFR gene may be used here as a dominant selectable marker and the transformed cells are selected in hypoxanthine/thymidine-free medium.

Other amplifiable selectable marker genes which may be used according to the invention are for example glutamine-synthetase, metallothionein, adenosine-deaminase, AMP-deaminase, UMP-synthase, xanthine-guanine-phosphoribosyltransferase and thymidylate-synthetase.

In one embodiment, the determination of predetermined ratios of the DNA sequences of the asymmetric antibody constructs is determined in a transient transfection system. In another embodiment, the determination of predetermined ratios of the DNA sequences of the asymmetric antibody constructs is determined in a transient transfection system.

A transient transfection system is characterised by non-appliance of any selection pressure for a vector borne selection marker. A pool or batch of cells originating from a transient transfection is a pooled cell population that comprises cells which have taken up and do express and cells that have not taken up the foreign DNA. In transient expression experiments which commonly last 20-50 hours post transfection, the transfected vectors are maintained as episomal elements and are not yet integrated into the genome. That is the transfected DNA, does not usually integrate into the hostcell genome. The host cells tend to lose the transfected DNA and overgrow transfected cells in the population upon culture of the transiently transfected cell pool. Therefore expression is strongest in the period immediately following transfection and decreases with time.

In stable transfection systems, the expression vector containing a selectable marker, as described above, is incorporated into genomic DNA, usually by random, non-homologous recombination events. The copy number of the vector DNA and concomitantly the amount of the gene product can be increased by selecting for cell lines in which the vector sequences have been amplified after integration into the DNA of the mammalian cell. Therefore, it is possible that such stable integration gives rise, upon exposure to further selection pressure for gene amplification, to double minute chromosomes in the mammalian cells. Furthermore, in case of a vector sequence, a stable transfection may result in loss of vector sequence parts not directly related to expression of the recombinant gene product or asymmetric antibody product, such as e.g. bacterial copy number control regions rendered superfluous upon genomic integration. Therefore, a transfected mammalian cell has integrated at least part or different parts of the expression vector into the genome.

After introduction of the expression vector containing the DNA sequences of the asymmetric antibody construct into the mammalian cell, the obtained transfectants are cultured under conditions that select for mammalian cells expressing the selectable marker. For example, when the selectable marker gene is an antibiotic resistance gene, transfectants are cultured in a medium containing the corresponding antibiotic active in mammalian cells and the transfectants which are viable under such conditions are selected, thus enabling the obtainment of transfectants which express the marker gene and thus incorporate the expression vector.

Asymmetric Antibody Product Expression and Selection of High-Producing Host Cells:

The term "expression" relates to the transcription and/or translation of an asymmetric antibody construct in a host cell. The expression rate can be generally determined, either on the basis of the quantity of corresponding mRNA which is present in the host cell or on the basis of the quantity of asymmetric antibody product produced. The quantity of mRNA produced by transcription of a selected nucleotide sequence can be determined for example by northern blot hybridisation, ribonuclease-RNA-protection, in situ hybridisation of cellular RNA or by PCR methods (e.g. quantitative PCR). Proteins which are encoded by a selected nucleotide sequence can also be determined by various methods such as, for example, ELISA, protein A HPLC, western blot, radioimmunoassay, immunoprecipitation, detection of the biological activity of the protein, immune staining of the protein followed by FACS analysis or fluorescence microscopy, direct detection of a fluorescent protein by FACS analysis or fluorescence microscopy.

By "titre or productivity" is meant the level of expression, synthesis or secretion of a asymmetric antibody construct introduced into a host cell, for example of a gene coding for a therapeutic protein. In one embodiment the titre of the asymmetric antibody expressed following Protein A purification is greater than about 100 mg/L. In another embodiment, the titre of the asymmetric antibody expressed following Protein A purification is greater than about 200 mg/L. In another embodiment, the titre of the asymmetric antibody expressed following Protein A purification is greater than about 300 mg/L. In another embodiment, the titre of the asymmetric antibody expressed following Protein A purification is greater than about 500 mg/L. In one embodiment, the titre of the asymmetric antibody product expressed following Protein A purification is comparable to that of a naturally-occurring, or wild-type antibody expressed using recombinant methods in a mammalian cell.

The corresponding processes may be combined with a FAGS-assisted selection of recombinant host cells which contain, as additional selectable marker, one or more fluorescent proteins (e.g. GFP) or a cell surface marker. Other methods of obtaining increased expression, and a combination of different methods may also be used, are based for example on the use of cisactive elements for manipulating the chromatin structure (e.g. LCR, UCOE, EASE, isolators, S/MARs, STAR elements), on the use of (artificial) transcription factors, treatment of the cells with natural or synthetic agents for up-regulating endogenous or heterologous gene expression, improving the stability (half-life) of mRNA or the protein, improving the initiation of mRNA translation, increasing the gene dose by the use of episomal plasm ids (based on the use of viral sequences as replication origins, e.g. SV40, polyoma, adenovirus, EBV or BPV), the use of amplification-promoting sequences or in vitro amplification systems based on DNA concatemers.

In one embodiment, the method further includes a step of replicating transfected host cells (or production cells) that produce the asymmetric antibody product of interest. For this, the selected high producing cells are preferably cultivated in a serum-free culture medium and preferably in suspension culture under conditions which allow expression of the asymmetric antibody product. In one embodiment, the asymmetric antibody product is obtained from the cell culture medium as a secreted gene product. In another embodiment if, for example, the protein is expressed without a secretion signal, however, the asymmetric antibody product may also be isolated from cell lysates. In order to obtain a pure homogeneous asymmetric antibody product which is substantially free from other recombinant proteins and host cell proteins, conventional purification procedures can be carried out. First of all, cells and cell debris are removed from the culture medium or lysate. The desired asymmetric antibody product can then be freed from contaminating soluble proteins, polypeptides and nucleic acids, e.g. by fractionation on immunoaffinity and ion exchange columns, ethanol precipitation, reversed phase HPLC or chromatography on Sephadex, silica or cation exchange resins such as DEAE. Methods which result in the purification of a heterologous protein expressed by recombinant host cells are readily available to one of skill in the art and are described in the literature.

In one embodiment, the asymmetric antibody product is expressed in a pool of stable transfectants. In another embodiment, the asymmetric antibody product is expressed in a single monoclonal stable transfectant.

4.2.5/Dentifying Predetermined Ratios

In order to optimize the expression product of the process such that a suitable level of asymmetric antibody product is produced, with minimal homodimer, monomer and other contamination, an initial screening procedure can be carried out to test the effect of various ratios of the DNA sequences of the asymmetric antibody construct on the composition of the expression product produced by the process according to the invention. The predetermined ratio of the DNA sequences of the asymmetric antibody construct used to prepare the asymmetric antibody product-producing stable mammalian cell lines is determined by first preparing various test ratios of the DNA sequences of the asymmetric antibody construct according to weight or according to copy number. It is understood that the range of test ratios generated will vary depending on the format of the asymmetric antibody to be produced with respect to the number of DNA or nucleic acid sequences required to encode the asymmetric antibody product, or with respect to the specific sequences of the antigen-binding domains and the DNA or nucleic acid sequences required to encode them. The range of test ratios to be generated can readily be determined by a worker skilled in the art once a specific asymmetric antibody construct has been selected. Thus, the range of test ratios described below are not meant to be limiting.

In one embodiment the predetermined ratio of the DNA sequences of the asymmetric antibody constructs are assessed by combining different test ratios of the plasmids containing the DNA sequences on the basis of weight of each plasmid. Thus, for an asymmetric antibody construct comprising two heavy chains and one light chain, in one embodiment, the ratio of the first heavy chain (HC1) to second heavy chain (HC2) to light chain is 1:1:2.5 by weight. In another embodiment for such an asymmetric antibody, the ratio of the first heavy chain (HC1) to second heavy chain (HC2) to light chain is 1:1:3 by weight. In another embodiment for such an asymmetric antibody, the ratio of the first heavy chain (HC1) to second heavy chain (HC2) to light chain is 1:1:2 by weight.

In another embodiment, the predetermined ratio of the DNA sequences of the asymmetric antibody constructs are assessed by combining different test ratios of the copy number of each plasmid encoding the DNA sequences. Thus, for an asymmetric antibody construct comprising two heavy chains and one light chain, in one embodiment, the ratio of the first heavy chain (HC1) to second heavy chain (HC2) to light chain is 1:1:2.5 by copy number. In another embodiment for such an asymmetric antibody, the ratio of the first heavy chain (HC1) to second heavy chain (HC2) to light chain is 1:1:3 by copy number. In another embodiment for such an asymmetric antibody, the ratio of the first heavy chain (HC1) to second heavy chain (HC2) to light chain is 1:1:2 by copy number.

As is known in the art, in the case of multi-cistronic vectors comprising the nucleic acid sequences encoding the asymmetric antibody product, predetermined ratios are determined differently. The expression levels of the different nucleic acid sequences in the multi-cistronic vector can be varied according to methods known in the art (see for example Hennecke et al, (2001) Nucl. Acids Res. 29:3327-3334, and US Patent Publication No. 2006/0263882) in order to identify the parameters necessary to provide an expression product comprising at least 75% of the asymmetric antibody product and less than 10% of the homodimers. The design of such multi-cistronic vectors is within the knowledge of one of skill in the art.

Once the DNA sequence test ratios or the different designs of the multi-cistronic vector have been prepared, they are transfected into the selected cell line using either a transient transfection system, or a stable transfection system. In one embodiment, the predetermined ratio of DNA sequences is assessed in a transient transfection system. In this embodiment, various test ratios of the DNA sequences required to express the asymmetric antibody are transiently transfected into the selected cell line and the cell line cultured under conditions suitable to produce an expression product. In another embodiment, the predetermined ratio of DNA sequences is assessed in a stable transfection system, such that various test ratios of the DNA sequences required to express the asymmetric antibody are stably transfected into the selected cell line and cultured under selection conditions to select for those transfectants that have stably integrated the expression vector. The stable transfectants are then cultured under conditions suitable to produce an expression product. It is noted that the fidelity of ratios used in transient expression of the expression product is high in stably expressing cell lines.

Whether produced via transiently transfected cells or stably transfected cells, the expression product is then assessed to determine the amount of the asymmetric antibody construct produced, the amount of homodimer produced, and the amount of monomer produced.

Test ratios that produce an expression product comprising greater than 78% of the asymmetric antibody product are selected for generation of the transient or stable cell lines used for production. In one embodiment, a test ratio comprising greater than 80% of the asymmetric antibody product is selected for generation of the transient or stable cell lines used for production. In one embodiment, a test ratio comprising greater than 85% of the asymmetric antibody product is selected for generation of the transient or stable cell lines used for production. In one embodiment, a test ratio comprising greater than 90% of the asymmetric antibody product is selected for generation of the transient or stable cell lines used for production. In one embodiment, a test ratio comprising greater than 95% of the asymmetric antibody product is selected for generation of the transient or stable cell lines used for production. In one embodiment, a test ratio comprising greater than 98% of the asymmetric antibody product is selected for generation of the transient or stable cell lines used for production. In one embodiment, a test ratio comprising greater than 99% of the asymmetric antibody product is selected for generation of the transient or stable cell lines used for production. Methods for assessing the composition of the expression product are described elsewhere herein.

In one embodiment, the selected cell line is the same cell line used for subsequent preparation of the stable cell line. In one embodiment, the predetermined ratio is determined in one mammalian cell line and stable cell lines are prepared using a different mammalian cell.

The assessment of the expression products can be carried out in pools of transfected cells, or in individual transfected cells. Thus in one embodiment, the process according to the invention comprises tranfecting at least two different cells with different pre-determined ratios of said first DNA sequence, said second DNA sequence and said third DNA sequence such that each of the two cells expresses the heavy chain polypeptides and the light chain polypeptide in a different ratio.

In one embodiment where the asymmetric antibody construct comprises a first DNA sequence encoding a first heavy chain polypeptide, a second DNA sequence encoding a second heavy chain polypeptide, and a third DNA sequence encoding a light chain polypeptide, the predetermined ratio of the first DNA sequence:second DNA sequence:third DNA sequence is such that the amount of translated first heavy chain polypeptide is about equal to the amount of the second heavy chain polypeptide, and the amount of the light chain polypeptide is at least about two fold greater than the amounts of either of the heavy chain polypeptides.

In one embodiment where the asymmetric antibody construct comprises a first DNA sequence encoding a first heavy chain polypeptide, a second DNA sequence encoding a second heavy chain polypeptide, and a third DNA sequence encoding a light chain polypeptide, the predetermined ratio of the first DNA sequence:second DNA sequence:third DNA sequence is such that the amount of translated first heavy chain polypeptide is greater than the amount of the second heavy chain polypeptide, and the amount of the light chain polypeptide is at least about two fold greater than the amount of the first heavy chain polypeptide.

In one embodiment where the asymmetric antibody construct comprises a first DNA sequence encoding a first heavy chain polypeptide, a second DNA sequence encoding a second heavy chain polypeptide, and a third DNA sequence encoding a light chain polypeptide, the predetermined ratio of the first DNA:the second DNA:the third DNA is such that the amount of translated first heavy chain polypeptide is less than the amount of the second heavy chain polypeptide, and the amount of the light chain polypeptide is at least about two fold greater than the amount of the second heavy chain polypeptide.

Once the predetermined ratio of DNA sequences of the asymmetric antibody construct that provides the desired expression product has been identified, the predetermined ratio is then used to transfect the selected mammalian cell line in order to generate a stable cell line expressing the asymmetric antibody product.

4.2.6 Assessing Expression Products

The expression product generated by the method or process according to the invention potentially comprises varying amounts of the asymmetric antibody product (heterodimeric heavy chains), products comprising homodimers of each of the heavy chains, monomers or half antibodies (one heavy chain paired with one light chain), and additional contaminating species such as glycine or lysine truncated variants of these polypeptides. The composition of the expression product varies depending on the test ratios of DNA sequences used to transfect the mammalian cells.

In one embodiment, the expression product comprises greater than 78% of the asymmetric antibody product. In one embodiment, the expression product comprises greater than 80% of the asymmetric antibody product. In one embodiment, the expression product comprises greater than 85% of the asymmetric antibody product. In one embodiment, the expression product comprises greater than 90% of the asymmetric antibody product. In one embodiment, the expression product comprises greater than 95% of the asymmetric antibody product. In one embodiment, the expression product comprises greater than 98% of the asymmetric antibody product. In one embodiment, the expression product comprises greater than 99% of the asymmetric antibody product.

It is further contemplated that once the asymmetric antibody product is produced in a stable mammalian cell line, according to the process of the invention the asymmetric antibody can also be analyzed to confirm its composition. The methods described below are also suitable for this purpose.

The expression product can be analyzed directly from the culture medium, or can be subjected to at least one purification or concentration step prior to analysis. In one embodiment the expression product is assessed after a Protein A purification step.

In one embodiment, the expression product comprises 75-100% of the asymmetric antibody product as indicated above. In one embodiment, the expression product comprises between 0-10% monomers. In one embodiment, the expression product comprises between 0-10% homodimers.

Analyzing the composition of the expression product can be carried out according to methods known in the art. For example, LC/MS, SDS-PAGE, CE-SDS, Caliper Labchip, lon exchange chromatography, reverse phase chromatography, clEF can be used to identify and quantify the composition of the expression product.

Determining the amount of expression product can be carried out using protein quantitation methods known in the art, such as for example, ELISA or mass spectrometry.

4.2.7 Expression Protocols (Testing of Stable Transfectants)

It is further contemplated that the characteristics of the expressed product may be further refined by adjusting the parameters of the process with respect to the seeding density of the stable cells in culture, or by "cell boosting."

The performance of CHO pools stably expressing the asymmetric antibody antibody product substance can be assessed in square bottles (seeding 3×10 c/ml, 50 ml culture volume) within fed-batch cultivation with Cell Boost and feeding at day 0, 2, 3, 6, 7, 8. Performance criteria include cell concentration [greater than 1 E+06 cells/mL], doubling time [>17 h], and lgG titre [>14 µg/mL] that can be assessed on days 3 and 7. It is further demonstrated that selection of the top stably expressing pool include assessment of the cumulative Titre curves, SDS page analysis of the cumulative antibody product secreted in media, and the antibody product purity as assessed by MS.

In one embodiment, selection of stable clones from the top pool involves plating cells in semisolid medium and growing clones selected by ClonePix and transferred to 96 well plates. Growing clones and their titre are determined by ELISA and the 20 best expressing candidates are then expanded by suspension cultivation. The 10 best candidates from these are then expanded in shake flasks. A further 10 candidates may be chosen by repeating the clone selection procedure from the pool using the aforementioned cell culture growth criteria.

It is further demonstrated that varying Feed frequency along with Cell Boost 5 and its effect on Cell growth can improve product quality of a selected clone stably expressing the antibody product. Other parameters include agitation, temperature, seeding density, and working volume and selection of the suitable parameters for manufacturability is done via a matrix design.

4.2.8 Analysis of Expression Products Produced by Transfected Mammalian Cells In one embodiment, the expression product is first analyzed for its purity characteristics i.e. the percentage of heterodimeric Fc relative to the contaminant homodimers and the monomers (half antibodies). Analytical techniques such as LC-MS, SDS, UV analysis (A380), size exclusion chromatography (SEC), SEC HPLC, capillary electrophoresis SDS (CE-SDS), Prot A HPLC, iciEF, reverse phase chromatography, UPLC that are well known in the art can be employed to characterize the types of antibody molecules present in the expression product post protein A affinity purification. In one embodiment, the standard methods listed here can be employed to establish the titre (product protein expression) levels. Standard deglycosylation technique such as using PNGaseF enzyme based digestion is used prior to intact MS analysis. The amino acid sequence of the asymmetric antibody product is analyzed by peptide mapping mass spectroscopic (MS) analysis and glycosylation pattern on the CH2 domain of the antibody can be characterized by MS techniques and using other kits known in the art such as Glycoprep for analysis of the N-glycosylation.

In one embodiment, once the preferred heterodimeric Fc based expression product is confirmed, the next array of biophysical characterization is aimed at characterizing its stability features. In one embodiment differential scanning calorimetry (DSC) is employed to characterize its thermal stability. Further stability analysis include Heat stress, acid base stress, agitation, oxdative stress, freeze-thaw characterization experiments coupled with other analytical approaches such as UV analysis and chromatographic UPLC and HPLC techniques can be employed. In one embodiment the formation of aggregated and other high molecular weight species as well as breakdown products of lower molecular weight are characterized in these forced degradation and stress experiments is studied. The Asymmetric antibody product of interest performs as well parent or native antibody in these experiments. The expressed asymmetric antibody product exhibits features that are useful in a therapeutic antibody such as, for example, glycosylation, proper assembly of the heavy and light chains of the antibody, correct disulfide bond formation.

In one embodiment, the expression product of the at least one stable mammalian cell comprises a larger percentage of the desired glycosylated asymmetric antibody as compared to the monomeric heavy or light chain polypeptides, or other antibodies.

In one embodiment, the expression product of the at least one stable mammalian cell comprises a greater percentage of the glycosylated asymmetric antibody compared to symmetric antibodies. In one embodiment, the expression product comprises a greater than two fold excess of the asymmetric antibodies compared to the symmetric antibodies.

In one embodiment, additional attributes of the asymmetric antibody in the expression product include stability under pH or temperature or physical stress.

4.3 Further Purification

The expression product produced by the transfected mammalian host cells can be further processed to obtain a purified asymmetric antibody product. Suitable purification methods include hydroxylapatite chromatography, gel electrophoresis, dialysis, and affinity chromatography. The suitability of protein A as an affinity ligand depends on the species and isotype of any immunoglobulin Fc domain that is present in the antibody. Protein A can be used to purify antibodies that are based on human lgG1 lgG2, or lgG4 heavy chains (Lindmark et al, J. Immunol. Meth. 62:1-13 (1983)). Protein G is recommended for all mouse isotypes and for human y3 (Gusset al, EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a C R 3 domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the expression product may be subjected to low pH hydrophobic interaction chromatography using an elution buffer at a pH between about 2.5-4.5, preferably performed at low salt concentrations (e.g., from about 0-0.25M salt).

4.4 Kits

The present invention additionally provides for kits comprising one or more stable cell lines of the invention. Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, use or sale. The kit may optionally contain instructions or directions outlining the method of use of the stable cell lines.

The components of the kit may also be provided in dried or lyophilised form and the kit can additionally contain a suitable solvent for reconstitution of the lyophilised components.

It is understood that the examples and embodiments described herein are for illustrative purposes only and that various modifications or changes in light thereof will be suggested to persons skilled in the art and are to be included within the spirit and purview of this application and scope of the appended claims.

5. EXAMPLES

The examples below are given so as to illustrate the practice of this invention. They are not intended to limit or define the entire scope of this invention.

EXAMPLES

The examples below are given so as to illustrate the practice of this invention. They are not intended to limit or define the entire scope of this invention.

Example 1: Method of Screening and Generating Stable Pools of Mammalian Cells with Different Ratios of DNA Encoding First Heavy Chain Polypeptide, Second Heavy Chain Polypeptide and Light Chain Polypeptide for the Production of Glycosylated Asymmetric Antibodies For an asymmetric antibody construct comprising two different heavy chain polypeptides and one light chain polypeptide, 9 stable CHO pools were generated by transfecting 3 different plasmids at different ratios of DNA encoding first heavy chain polypeptide, DNA encoding second heavy chain polypeptide and DNA encoding light chain polypeptide as shown in FIG. 1. Protein yield at this stage of cell line generation was comparable to other antibodies (about 0.25 mg/ml) post protein A purification. The expressed protein from the different pools was then screened by LC/MS. As seen in FIG. 2, for the asymmetric antibody construct expressed in the current study, at the optimum ratio of DNA encoding first heavy chain polypeptide:DNA encoding second heavy chain polypeptide:DNA encoding light chain polypeptide, minimal half antibody observed (FIG. 1, Pool N).

In the case of this particular glycosylated asymmetric antibody, this ratio corresponds to a slight excess of DNA encoding the light chain polypeptide and equal amounts of DNA encoding the first heavy chain polypeptide and second heavy chain polypeptide.

A more detailed description of the procedural steps for asymmetric antibody construction, expression and pool analysis is provided in Examples 3 to 8 below.

Example 2: LC/MS Characterization of Expression Products from Stable Pools of Mammalian Cells for the Production of Glycosylated Asymmetric Antibodies As shown in FIG. 3, LC/MS characterization of the protein A purified expression products obtained from the 9 stable CHO pools screened in Example 1 shows that the preferred pool (N) does not form any homodimer. All the whole antibody species is the desired glycosylated asymmetric antibody. The only contaminants are monomeric species. FIG. 4 shows LC/MS analysis of other heterodimers comprising two different heavy chain polypeptides and one common light chain, obtained by the method described herein. At equal plasmid levels of DNA encoding heavy chain A and DNA encoding heavy chain B no contaminant homodimers of either chain A or B are observed for any of the heteromultimers prepared by the method described herein.

A more detailed description of the procedural steps taken for LC/MS quantification of each stable pool is provided in subsequent Examples.

Example 3: Description of the Heavy-Chain A, Heavy-Chain B and the Light Chain Constructs and Preparation of Clones An exemplary asymmetric antibody construct (ZW1) comprising two heavy chains, heavy chain A (HC-A) and heavy chain B (HC-B), and one common light chain was constructed. The wild-type amino acid and nucleotide sequences for the LC and HC for trastuzumab are provided in FIGS. 14 and 15 respectively. For the ZW1 constructs, CH3 region of the wild-type HER2 antibody heavy chain polypeptides was modified as follows:

Chain-A: T350V_L351Y_F405A_Y407V; Chain-B: T305V_T366L_K392L_ T394W

For the KnH constructs, the following CH3 amino acids were mutated:

Chain-A: T366W; Chain-B: T366S_L368A_Y407V

Plasmid constructs containing heavy chain A (HC-A), heavy chain B (HC-B) and light chain (LC) were created as follows. The genes encoding the antibody heavy and light chains were constructed via gene synthesis using codons optimized for human/mammalian expression. The Fab sequences were generated from a known Her2/neu binding Ab (Carter P. et al. (1992) Humanization of an anti P185 Her2 antibody for human cancer therapy. *Proc Natl Acad Sci* 89, 4285.) and the Fc was an IgG1 isotype. The final gene products were sub-cloned into the mammalian expression vector pTT5 (NRC-BRI, Canada) (Durocher, Y., Perret, S. & Kamen, A. High-level and high-throughput recombinant protein production by transient transfection of suspension-growing human HEK293-EBNA1 cells. *Nucleic acids research* 30, E9 (2002)). The mutations in the CH3 domain were introduced via site-directed mutagenesis of the pTT5 template vectors.

Example 4: Preliminary Screening to Determine Optimal DNA Ratios of Heavy Chain A, Heavy Chain B and Light Chain Required to Produce a Heterodimeric Antibody Product In order to determine an optimal DNA ratio of HC-A: HC-B:LC for the production of heterodimeric asymmetric antibody constructs, a preliminary screen of DNA ratios to combine HC-A, HC-B and LC was performed to optimize for the production of heterodimer (antibody constructs with HC-A, HC-B, and two LCs) over homodimer (antibody constructs with two HC-A chains and two LCs, or with two HC-B chains and two LCs). The preliminary screening was performed by transiently transfecting the CHO (Chinese hamster ovary) cell line with various DNA ratios and analyzed using LC/MS as follows.

This experiment was performed for the two asymmetric antibody clones, KnH and ZW1 prepared as described in Example 3. The three plasmids constructs encoding KnH and ZW1 (HC-A, HC-B and LC) were transiently transfected into CHO cells in the following DNA ratios:

1 HC-A to 1.5 HC-B (LC/HC-NHC-B: 50%/20%/30%)
1 HC-A to 1 HC-B (LC/HC-NHC-B: 50%/25%/25%)
1.5 HC-A to 1 HC-B (LC/HC-NHC-B: 50%/30%/20%)

The cells were transfected in exponential growth phase (1.5 to 2 million cells/ml) with aqueous 1 mg/ml 25 kDa polyethylenimine (PEI, Polysciences) at a PEI:DNA ratio of 2.5:1. (Raymond C. et al. A simplified polyethylenimine-mediated transfection process for large-scale and high-throughput applications. Methods. 55(1):44-51 (2011)). The DNA was transfected in three separate ratios of the two heavy chains. For example, the transfection DNA, comprised of 5% GFP, 45% salmon sperm DNA, 25% light chain and 25% total heavy chains, where the heavy chain A plasmid and the heavy chain B plasmid were sampled at the different relative ratios stated above. At 4 to 48 hours after transfection in F17 serum-free media (Gibco), TN1 peptone is added to a final concentration of 0.5%.

LC/MS

The antibody expression in the transfected cells was analyzed using LC/MS. The purified samples were analyzed as is or de-glycosylated with PNGaseF (0.2 U PNGaseF/µg of antibody in 50 mM Tris-HCI pH 8.0; overnight incubation at 37° C.; final protein concentration was 0.45 mg/mL) or alternatively with EndoS (Deglycosylation with EndoS using manufacturer protocol conditions, 50 mM Tris-HCI pH 8.0 and incubation for 1 h at 37° C.). The protein samples were analyzed by LC-MS using an Agilent 1100 HPLC system coupled to an LTQ-Orbitrap XL hybrid mass spectrometer (ThermoFisher Scientific) via a high-flow electrospray interface. The samples (2.5 µg) were injected onto a 2.1×10 mm Poros R2 column (Applied Biosystems) and eluted using a 2 ml/min gradient of 20-90% ACN, 0.1% FA over 3 minutes. The flow was split post-column to direct 100 µL/min into the electrospray interface. The column and solvent were heated to 80° C. to improve protein peak shape. The LTQ-Orbitrap XL was calibrated using ThermoFisher Scientific's LTQ Positive Ion ESI calibration solution (caffeine, MRFA and Ultramark 1621), and tuned using a 25 ug/uL solution of BSA. The cone voltage (source fragmentation setting) was 40 V, the FT resolution was 7,500 and the scan range was m/z 400-4,000. The protein spectra were deconvoluted using ThermoFisher's Promass software (input range: m/z 2500-3050; output mass range: 100,000-160,000 Da; Peak width: 1.5; Merge width: 0.5; Baseline removal: 0.5 (low)). The abundances of the hetero- and homodimer antibody species were determined directly from the resulting molecular weight profiles. The linearity of response was confirmed using defined mixtures of antibodies. Limits of detection were approximately 2%.

FIG. 4 is the LC/MS analysis of the two asymmetric antibody clones at different DNA ratios. As the figure shows, at all three ratios, ZW1 forms exclusively heterodimers over the tested expression range. Only at a ratio of 1.5 HC-A to 1 HC-B for the KnH control was there a peak associated with AA homodimer formation, representing about 10 percent of the total antibody product produced.

Figure 7:
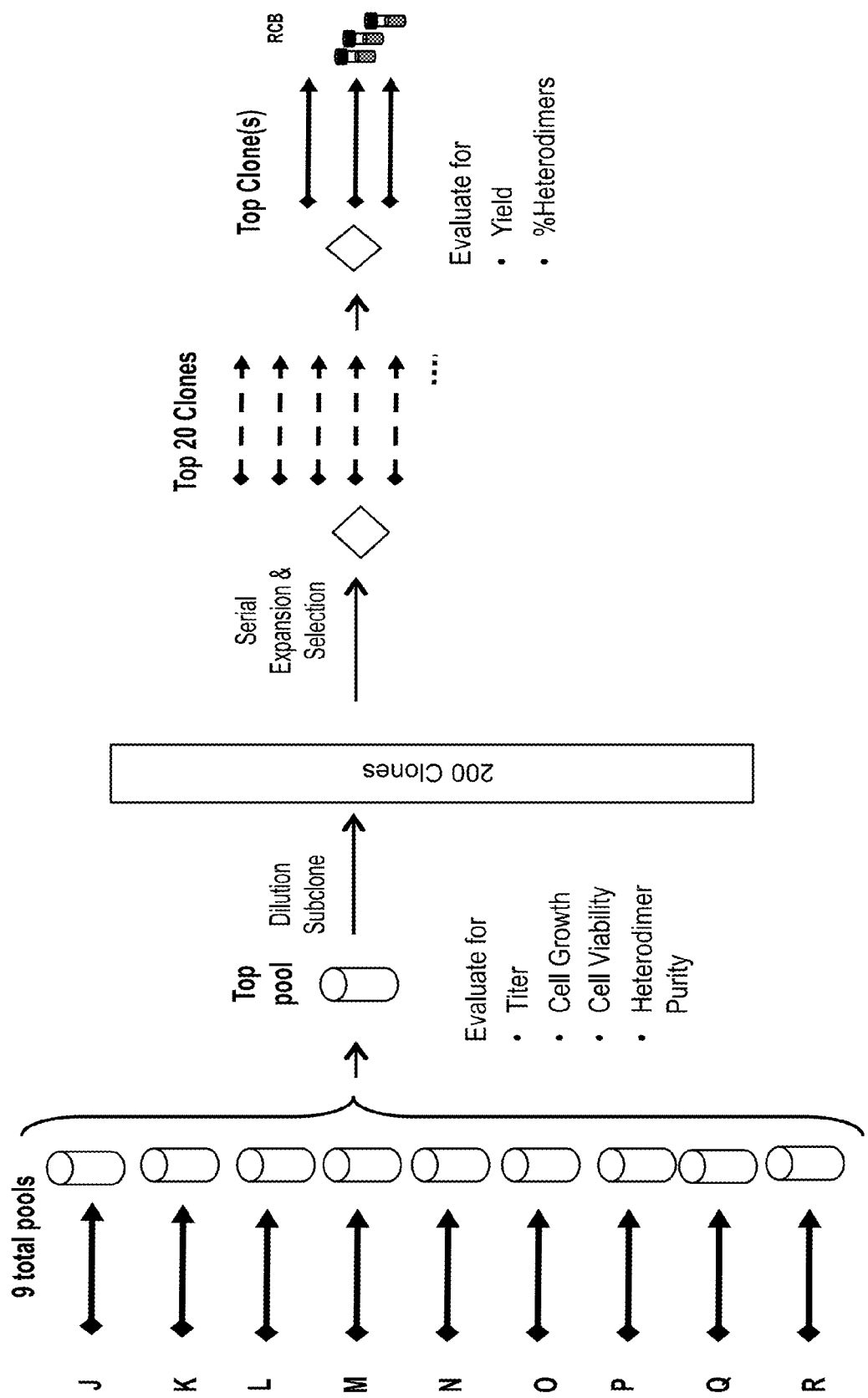
FIG. 7 shows a summary overview of the methods described in Examples 1 to 5, specifically steps used to isolate and characterize the top clones preferentially expressing the heterodimeric antibody when starting out with plasmid constructs.

Example 5: Method of Generating and Analyzing Stable Cell Pools with Varying DNA Ratios of Heavy-Chain A, Heavy-Chain B and Light-Chain Plasmids Used to Produce Heterodimeric Antibodies FIG. 7 provides a summary overview of Examples 5 to 8, or the steps taken to isolate and characterize the top clones preferentially expressing the heterodimeric antibody.

As described in Example 1, nine pools of stably transfected CHO cells containing different ratios of the HC-A, HC-B and LC plasmids were created. Example 5 describes the details of preparation and characterization of these pools.

The three plasmids containing HC-A, HC-B and LC for ZW1 were stably transfected into CHO cells in the DNA ratios provided in FIG. 1.

Stable CHO cell lines were generated using Selexis's propriatory SUREtech transfection and integration technology for stable pool generation and the ClonePix technology for generation and selection of stable clones. The stable cell lines were generated using Selexis's standard protocol and 1 round of SUREtech transfection for pool generation.

One (1) SUREtech transfection series using different ratios of light chain and heavy chain A:heavy chain B was carried out using monocistronic vectors (containing the Puromycin resistance cassette), generating pools # J, K, L, M, N, 0, P, Q and # R The antibody expression titer of the nine pools described above was examined and the results in micrograms of IgG per mL each stable cell pool are listed in Table A below.

TABLE A

| Pool | Day 10 IgG [µg/mL] |
| --- | --- |
| J | 504 |
| K | 218 |
| L | 310 |
| M | 420 |
| N | 304 |
| O | 531 |
| P | 406 |
| Q | 242 |
| R | 381 |

LC/MS

A purity assessment method for evaluation of homodimers in a bispecific antibody was also developed using LC-MS analysis of deglycosylated intact antibody on an Acquity UPLC—Xevo G2 QToF MS system. ZW1 heterodimer (AB—HeteroAB) and homodimer (AA—HomoA, and BB—HomoB) samples were deglycosylated and analyzed by intact mass LC-MS. To develop a quantitative LC-MS impurity assay, samples of deglycosylated HeteroAB were spiked with small amounts (<10%) of deglycosylated HomoA or HomoB and analyzed by LC-MS. Experimental percentages of HomoA or HomoB were calculated by comparing the deconvoluted peak intensities of whole antibody AA (for HomoA) or half antibody B (for HomoB) to the deconvoluted peak intensity of AB. Excellent linearity (R2>0.99) and reproducibility were obtained, and the limits of detection and quantification are approximately 2%.

Samples were deglycosylated by dilution with 0.1 M Tris, pH 7.5 and combined with 2.5 units PNGase F per microgram of sample. Final concentrations of sample were 1.0 mg/ml heterodimer. Reaction mixtures were incubated overnight at 37° C. followed by storage at 5° C. until LC-MS analysis. LC/MS analysis was performed on a Waters Acquity H-Class UPLC in line with a Waters Xevo G2 Q-ToF mass spectrometer. A blank injection (water) was run after every protein injection to minimize carryover and the reversed-phase UPLC separation (on a Waters Acquity UPLC BEH 300 1.7 µm column, 2.1×50 mm) was performed in 0.1% formic acid in H20 with a sharp gradient eluted of 0.1% formic acid in acetonitrile. MS was performed using the following parameters: Capillary voltage: 2.80 kV Sampling cone voltage: 57.0 V; Extraction cone voltage: 4.0 V Source temperature: 120° C. Desolvation temperature: 350° C. Cone gas flow: 20 L/hr Desolvation gas flow: 800 L/hr. The LC/MS data were subsequently analyzed with the MassLynx version 4.1 software package with Deconvolution parameters: Retention time window: 4.1-5.0 min; m/z input range: 2325-3350 for whole antibody; 1500-1948 for half antibody; output resolution: 1.0 Da/channel; output mass range: 70,000-150,000 Da. Uniform Gaussian width at half height: 1.5 Da for whole antibody; 1.3 Da for half antibody Minimum intensity ratios: Left 30%, Right 30% Maximum number of iterations: 15.

Figure 2A:
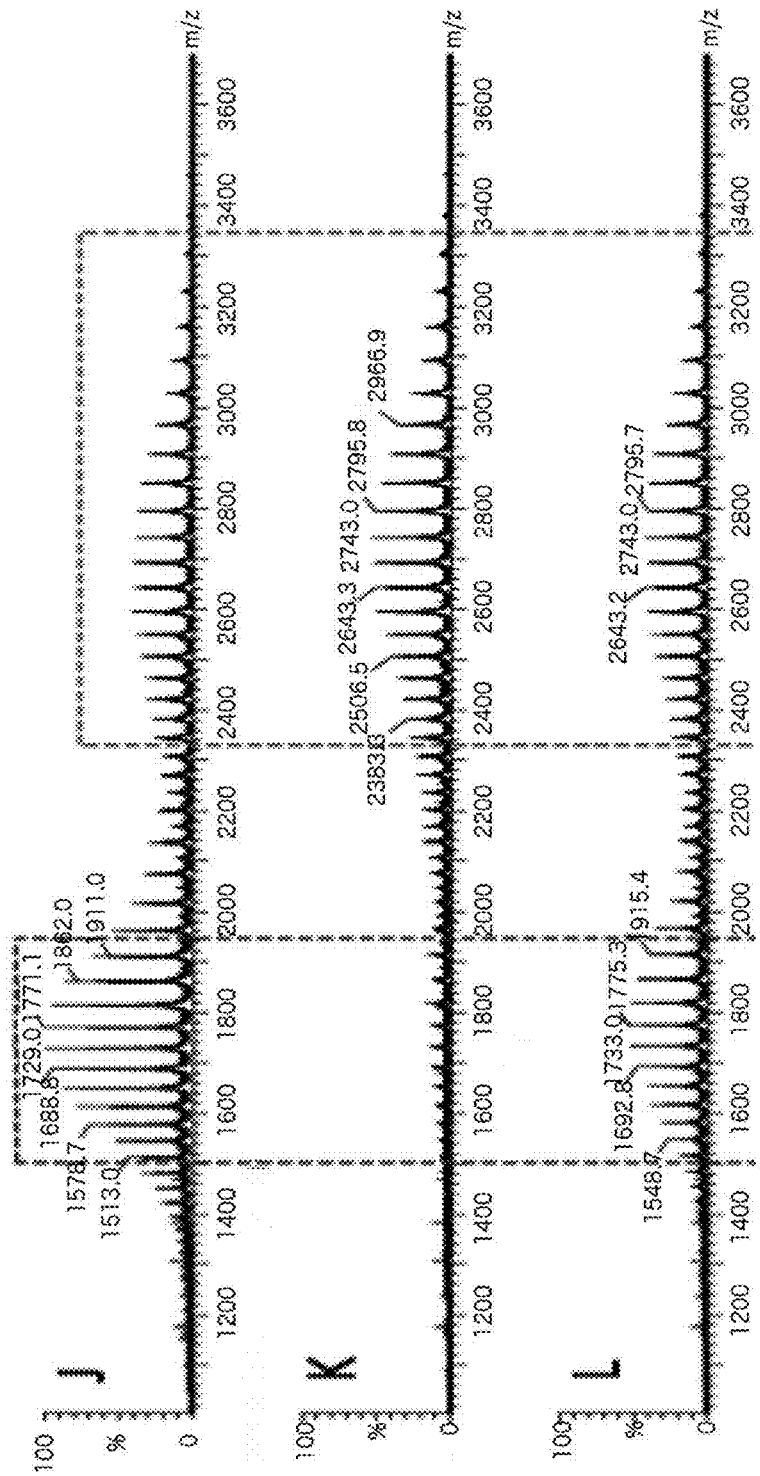
Figure 2A:
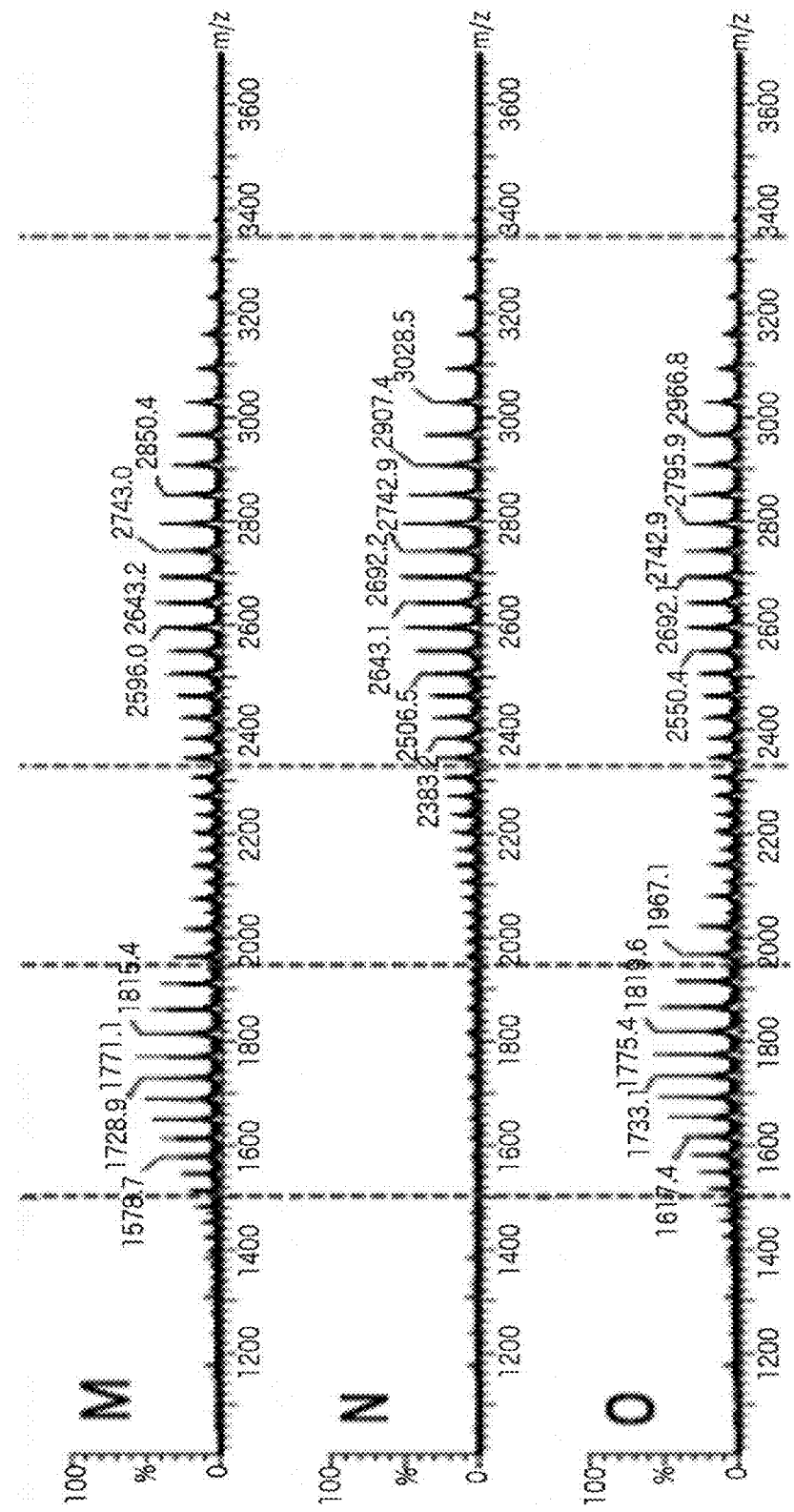
Figure 2B:
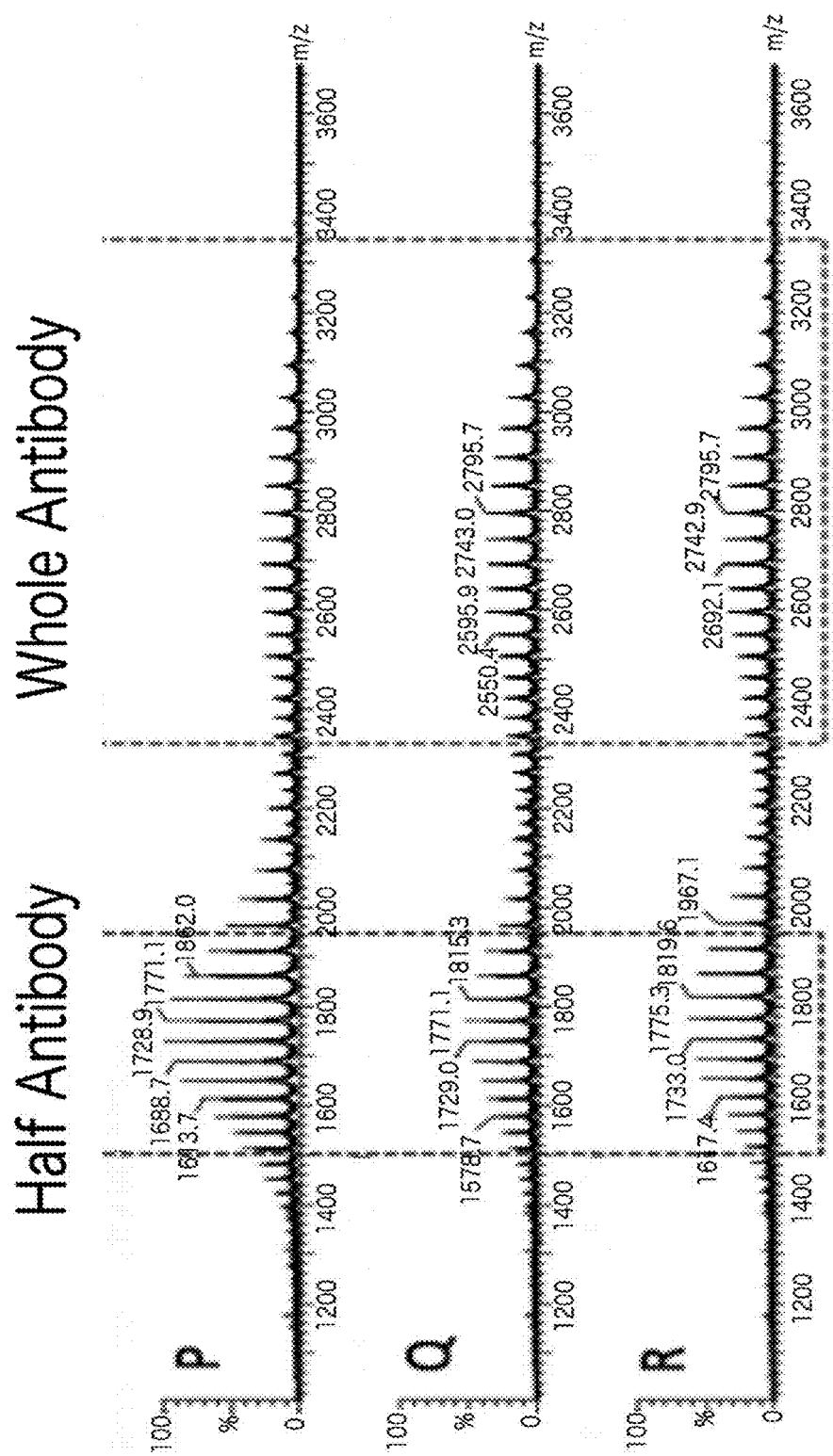

The mass spectrum of each cell pool is provided in FIGS. 2A and 2B. Half-antibodies are monomers containing one heavy-chain and one complementary light chain. Whole antibodies are heterodimers containing both HC-A and HC-B, and two complementary light chains. From FIG. 2, it can be seen that pools K and N express more of the desired whole antibodies and less of the half-antibody products.

Figure 3A:
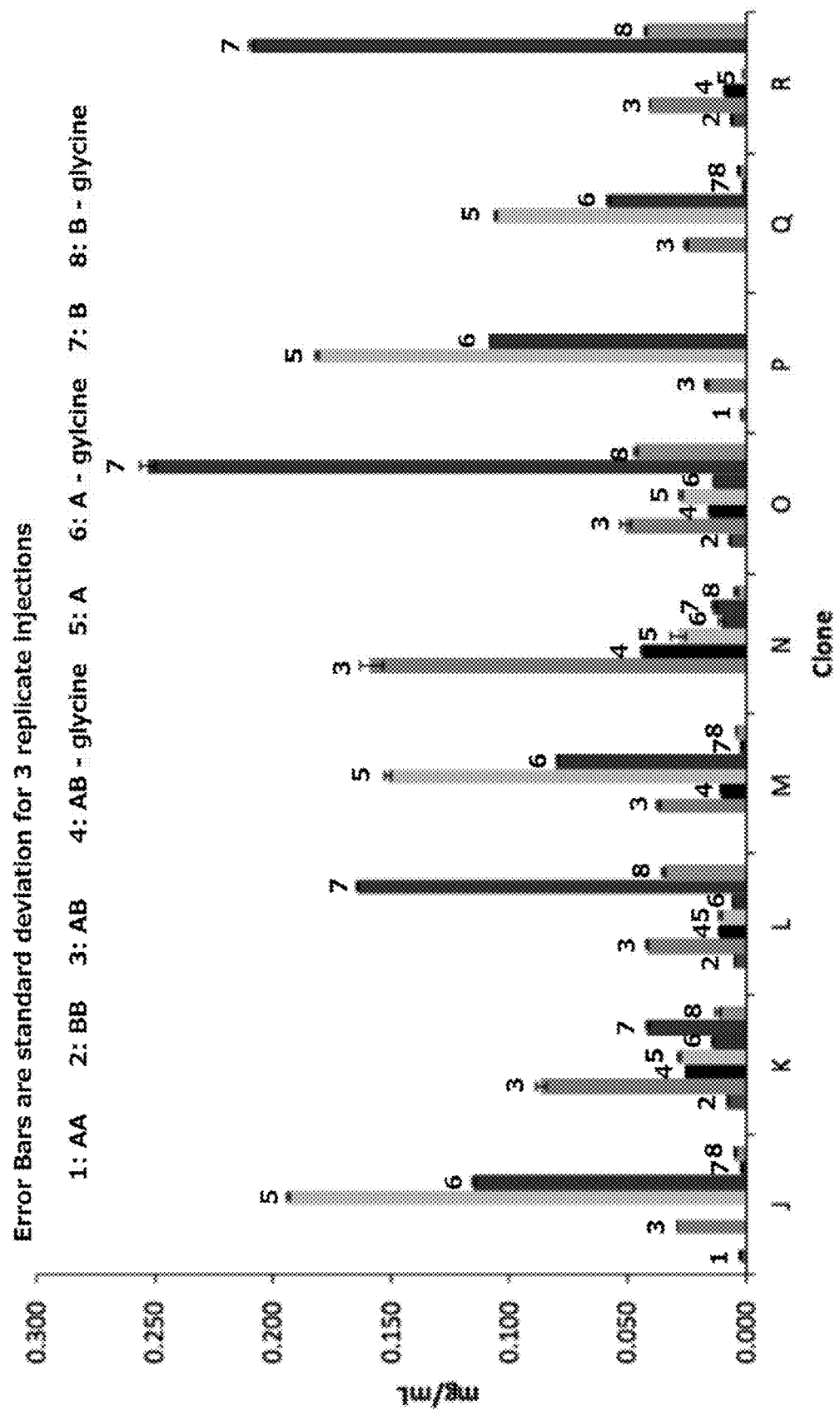
Figure 3B:
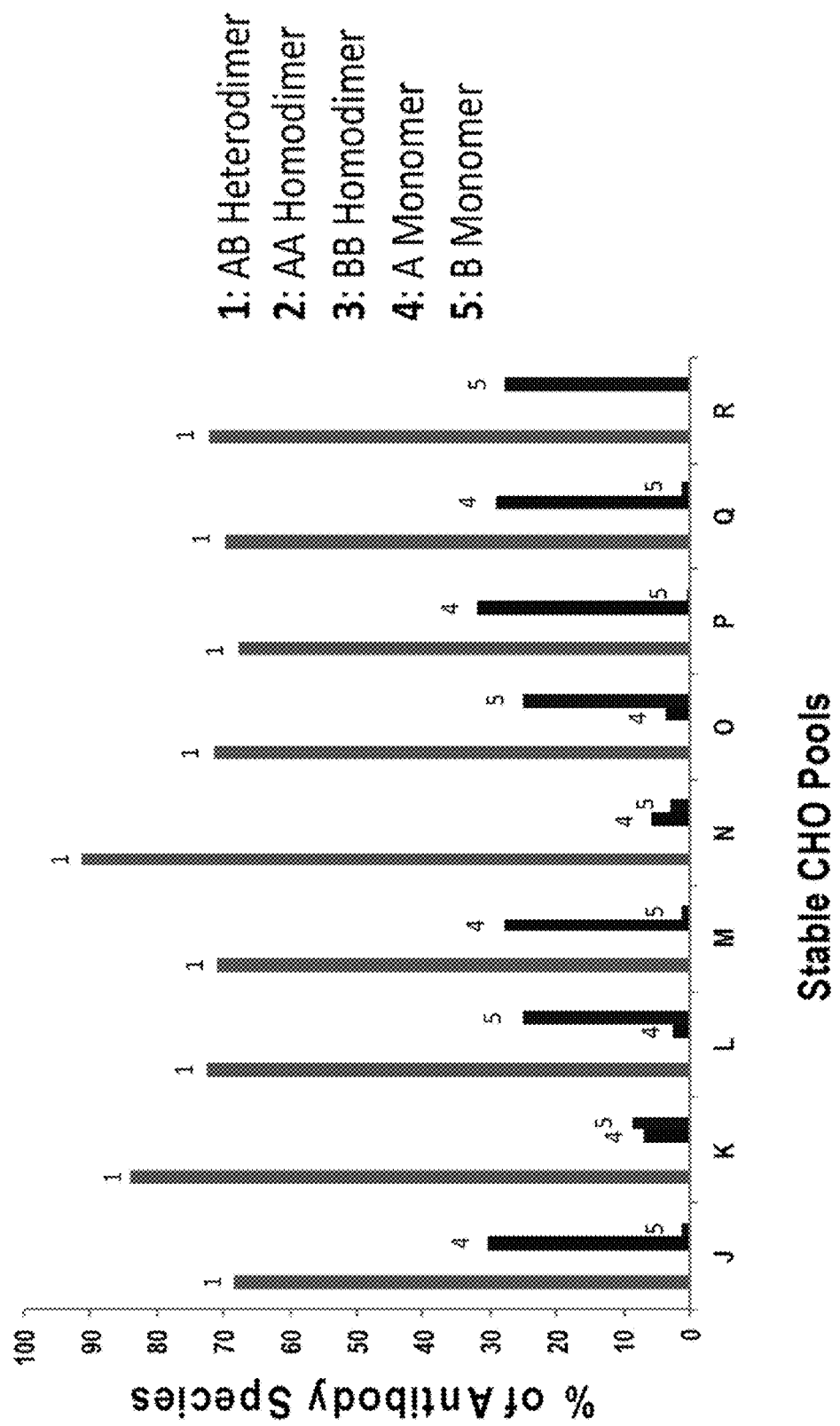
Figure 5:
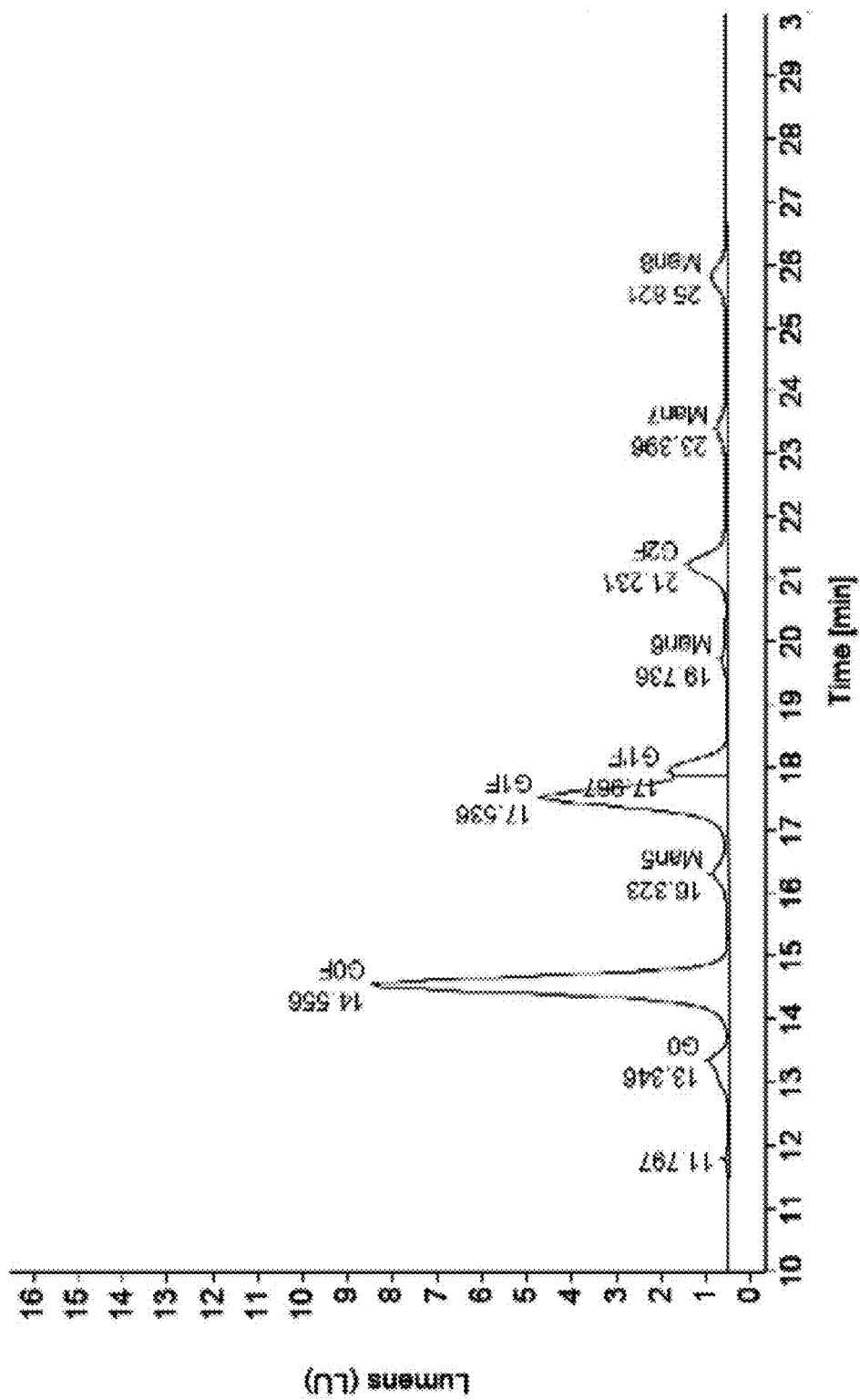
FIG. 5 shows the typical antibody-like glycosylation pattern in the derived asymmetric antibody.

The LCMS results were further analyzed to identify the various species of products obtained, and the results are shown in FIGS. 3A and 3B. FIG. 3A shows all products analyzed by the mass spectrometer as a result of liquid chromatography separation and enzyme digestion. FIG. 3B demonstrates normalization of the results, with each antibody product represented as a percentage of the total antibody species. The analysis showed that Pool N contained 91.6% heterodimers, 8.4% monomers and 0.0% homodimers. Pool N was selected for expansion and clone isolation based on heterodimer purity (FIGS. 2 and 3) and antibody expression titer (Table A).

Example 6. Method of Serial Expansion and of Top Clone Selection from Pool N

Individual clones from pool N that expressed antibody with reasonable titers and a high degree of heterodimer purity were identified and isolated as follows.

The clones from pool N were cultured on semi-solid plating.

One (1) single-cell derived colony picking round (ClonePix) was conducted to provide highly productive clonal cell lines, and the top 157 candidates were transferred into 97-well plates. Then, the candidates were serially expanded and selected on the basis of productivity using double sandwich ELISA. From the 157 candidates, the top 72 were transferred and cultured in 24-well plates; from the 72, the top 36 were transferred to 6-well plates; from the 36, the top 30 were selected and transferred to spin tubes; finally, the top 20 were selected and transferred into shaker flasks and subject to a full analysis. The 20 best performing clones were selected on the basis of titer and growth characteristics: # Ncp01, Ncp02, Ncp03, Ncp04, Ncp05, Ncp09, Ncp12, Ncp14, Ncp19, Ncp22, Ncp100, Ncp101, Ncp102, Ncp103, Ncp104, Ncp105, Ncp108, Ncp110, Ncp112 and # Ncp120.

Example 7. Characterization and Analysis of the Top 20 Clones

The top 20 clones identified in Example 2 were characterized and analyzed using ELISA, Protein-A HPLC, SDS-PAGE and LCMS as follows.

The antibody expression titers of the clones were determined using ELISA. The titer determined from the analysis is provided at the bottom of FIG. 8.

The level of monomer half-antibodies versus heterodimer whole-antibodies in each top clone was initially qualitatively determined using an SDS-PAGE gel.

Figure 8:
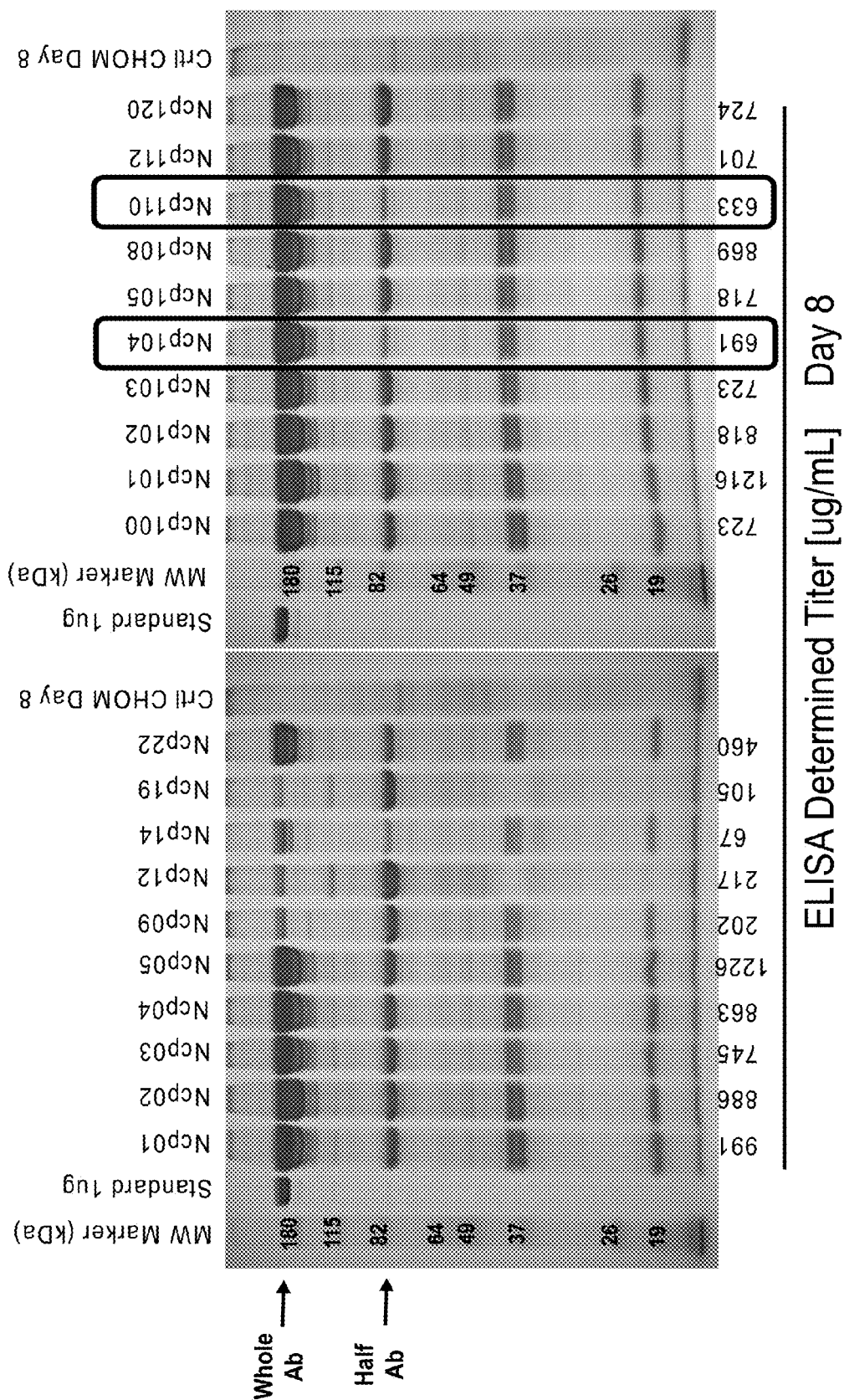
FIG. 8 represents SDS-PAGE and ELISA characterization of the top 20 clones described in Example 3. The figure has two components: the ELISA titers on the bottom represent the concentration of antibody products produced by each clone on Day 8 while the gel demonstrates the relative concentration of whole antibody to half antibody produced by each clone.

The results of the SDS-PAGE are provided in FIG. 8. The figure shows that both Ncp104 and Ncp110 have weak half-antibody bands paired with strong whole antibody bands.

Based a combination of high heterodimer purity and reasonable IgG expression titer levels, clones Ncp104 and Ncp110 were selected for further characterization by LCMS.

LC/MS Characterization

Ncp104 and Ncp110 were characterized using LC/MS as per methods described in Example 5.

The LC/MS spectrum for Ncp104 is shown in FIG. 9. Overall, Ncp104 stable clones were found to express 97% heterodimers and 3% monomers. The expression titer of the clone was about 800 mg of IgG per liter.

The LCMS spectrum for Ncp110 is shown in FIG. 10. Overall, Ncp110 stable clones were found to express 95% heterodimers along with 5% monomers. The expression titer of the Ncp110 clone was around 740 mg of IgG per liter.

The LC/MS spectrum for Ncp104 is shown in FIG. 9. Overall, Ncp104 stable clones were found to express 97% heterodimers and 3% monomers. The expression titer of the clone was about 800 mg of IgG per liter. The deconvoluted dimer spectrum shows peaks indicating heterodimers with Gly (AB-Gly) and 2Gly (AB-2Gly) truncations, and a minor peak of CH-A homodimer. The deconvoluted monomer spectrum show peaks indicating CH-A and CH-B monomers, and CH-A and CH_B monomers with Gly truncations (i.e. A-Gly, B-Gly).

The LCMS spectrum for Ncp110 is shown in FIG. 10. Overall, Ncp110 stable clones were found to express 95% heterodimers along with 5% monomers. The expression titer of the Ncp110 clone was around 740 mg of IgG per liter. The deconvoluted dimer spectrum shows peaks indicating heterodimers with Gly and 2Gly truncations, and a minor peak of CH-A homodimer. The deconvoluted monomer spectrum show peaks indicating CH-A and CH-B monomers, and CH-A monomers with Gly truncations (i.e. A-Gly).

Results indicate that clones Ncp104 and Ncp110 show high heterodimer purity and reasonable IgG titer.

These results indicate that both clones Ncp104 and Ncp110 show high heterodimer purity and reasonable IgG titer.

Example 8. Evaluation of the Stability of the Two CHO Clones, Ncp104 and Ncp110, at Different Growth and Feed Conditions Clone stability of the Ncp104 and Ncp110 at different growth and feed conditions was assessed using cell viability, cell growth and antibody titer as follows.

The two clones were grown at seven different conditions.

S-Control: 30 ml working volume; 300,000 seeding density

S-0.5 SD: 30 ml working volume; 500,000 seeding density

A: 30 mL Working Volume; 300,000 seeding density; Cell Boost5: Day 0, 2 and 5 (26% Initial Volume)

B: 30 mL Working Volume; 300,000 seeding density; Cell Boost5: Day 0 (40% Initial Volume)

C: 30 mL Working Volume; 300,000 seeding density; Cell Boost5: Day 0 and 2 (16% Initial Volume)

D: 30 mL Working Volume; 300,000 seeding density; Cell Boost5: Day 0 and 5 (16% Initial Volume)

E: 30 mL Working Volume; 300,000 seeding density; Cell Boost5: Day 0, 2, 3, 6 and 7 (4, 8, 12, 16 and 16% Initial Volume, respectively)

On Days 0 to 8, the cell viability, cell growth and titers of Ncp104 and Ncp110 were examined as follows.

FIGS. 11A, 11B and 11C respectively demonstrate percent viability, viable cell count and antibody titer of the Ncp104 clone over eight days. As the figures demonstrate, all three measures showed similar trends across the seven conditions. Cell viability remained consistently high; a viability drop observed on the eight day was most evident in condition S-0.5 SD. Cell growth was exponential for all seven conditions. Antibody titers increased from day 6 to 8 for all conditions, with the most significant increase being that of condition A.

FIGS. 12A, 12B and 12C respectively demonstrate percent viability, viable cell count and antibody titer of the Ncp110 clone over eight days. Similar to Ncp104, all three measures demonstrated similar trends across the conditions. Cell viability remained consistently high; a viability drop observed on the eight day was most evident in condition E. Cell growth was exponential for all seven conditions; the most significant growth was observed in condition S-0.5 SD. Antibody titers increased from day 6 to 8 for all conditions, with the most significant increase being that of condition S-0.5 SD.

Overall, this example demonstrate both the Ncp104 and Ncp110 clones are stable over a variety of growth/feed conditions and that antibody titer can be optimized as desired.

Example 9. Determination of Heterodimer Purity of the Ncp110 and Ncp104 Stable CHO Clones The heterodimer purity of Ncp104 and Ncp110 under four growth conditions were analyzed using Protein A HPLC) and LC/MS as per Example 5.

The stable clones were grown in shake flask fed-batch cultures under four different conditions.

(A) 50 mL shake flask cultures (120 rpm/36.5° C.) with Cell Boost 5 feed at days: 0, 2, 3, 6 and 7 (16% of Initial Volume);
(B) 50 mL shake flask cultures (120 rpm/36.5° C.) with Cell Boost 5 feed at day: 0, 2, 5 (26% of Initial Volume);
(C) 50 mL shake flask cultures (120 rpm/36.5° C.) with Cell Boost 5 feed at days: 0, 2 (16% of Initial Volume);
(D) 50 mL shake flask cultures (110 rpm/37.0° C.) with Cell Boost 5 feed at days: 0, 2, 3, 6 and 7 (16% of Initial Volume).

Cultures were harvested on the 8$^{th}$ day. Antibody titer and heterodimer purity were determined as follows.

Antibody titre was measured using the standard Protein-A HPLC method; results for each stable clone is described in Table B. Ncp104 at condition D provided the highest titer overall.

TABLE B

| Feed/growth condition | Ncp104 Titer (g/L) | Ncp110 Titer (g/L) |
|---|---|---|
| A | 0.62 | 0.76 |
| B | 0.73 | 0.77 |
| C | 0.56 | 0.57 |
| D | 0.80 | 0.74 |

LC/MS

Heterodimeric purity of both clones was assessed using LC/MS as described in Example 5. Quantitative LC-MS species assays were also analyzed as per the spiking method described in the LCMS portion of Example 5.

FIG. 13 shows a normalized LC/MS analysis of the various antibody products as a percentage of total antibody species. As can be seen from the figure, both Ncp110 and Ncp104 produced significantly more heterodimeric antibody than either homodimeric or monomeric ones. The purest stable clone was Ncp104 grown at either condition A or B, resulting in a final antibody specie composition of 97.8% heterodimers, 0.0% homodimers and 2.2% monomers.

Overall, this example demonstrates that both Ncp104 and Ncp110 are capable of producing large amounts of heterodimer in a variety of conditions without significant monomer or homodimer contamination.

Example 10: Transient Co-Expression of One-Armed Asymmetric Antibody Variants Using 3 Separate Vectors Two exemplary asymmetric antibodies comprising a two heavy chains, and one light chain, where one heavy chain polypeptide is a full-length heavy chain polypeptide (HC) and the second heavy chain polypeptide is a heavy chain polypeptide with a CH3, CH2 and hinge region (Fe) was constructed. This asymmetric antibody is designed to have a single antigen-binding domain that is a Fab and that binds to HER2. 1040 comprises a full-length heavy chain polypeptide (HC) on chain A with the CH3 mutations: T350V L351Y F405A Y407V, and a Fe heavy chain polypeptide on chain B with the CH3 mutations: T350V T366L K392L T394W 1041 comprises full-length heavy chain polypeptide (HC) on chain B with the CH3 mutations: T350V T366L K392L T394W, and a Fc heavy chain polypeptide on chain A with the CH3 mutations: T350V L351Y F405A Y407V.

The heavy chains and light chain were cloned into separate expression vectors as follows:

The final gene products were sub-cloned into the mammalian expression vector pTT5 (NRC-BRI, Canada) and expressed in CHO cells (Durocher, Y., Perret, S. & Kamen, A. High-level and high-throughput recombinant protein production by transient transfection of suspension-growing cho cells. *Nucleic acids research* 30, e9 (2002)).

The CHO cells were transfected in exponential growth phase (1.5 to 2 million cells/ml) with aqueous 1 mg/ml 25 kDa polyethylenimine (pei, polysciences) at a PEI:dna ratio of 2.5:1. (Raymond C. et al. A simplified polyethylenimine-mediated transfection process for large-scale and high-throughput applications. Methods. 55(1):44-51 (2011)). In order to determine the optimal concentration range for forming heterodimers, the dna was transfected in optimal DNA ratios of the heavy chain a (HC-A), light chain (LC), and heavy chain B that allow for heterodimer formation (e.g. HC-NHC-B/LC ratios=25:25:50%) Transfected cells were harvested after 5-6 days with the culture medium collected after centrifugation at 4000 rpm and clarified using a 0.45 μm filter.

Once the expression vectors were prepared, CHO cells were transiently transfected with 3 different ratios of LC:HC:Fc as shown in FIG. 17A. The expression product produced was purified by protein A chromatography and analyzed by SDS-PAGE to identify the expression products (left panel). The expression product resulting from a ratio of LC:HC:Fc=40:30:30 for each of 1040 and 1041 was further purified by gel filtration chromatography and the resulting product analyzed by SDS-PAGE. FIG. 17A shows the relative purity of transiently expressed v1040 and v1041 at three transfection ratios post protein A purification (left) and post SEC purification at the LC/HC/Fc transfection ratio of 40/30/30 (right).

The latter ratio of LC:HC:Fc=40:30:30 was used to transiently transfect a 10 L culture of CHO cells to produce larger scale expression of 1040 and 1041. The expression product was purified by protein A chromatography and size exclusion chromatography (SEC) and analzyed for the content of the asymmetric antibody. The SEC fractions indicated between the hashed lines were pooled and the pooled samples were assessed by LCMS, the results are shown in the deconvoluted spectrum (bottom). The transient 10 L cultures produced 20-40 mg/L of the asymmetric antibody with greater than 90% heterodimer purity following protein A and SEC purification.

Example 11: Cloning of One-Armed Asymmetric Antibody Variants into Triple Gene (TGV), Double Gene (DGV) and Single Gene (SGV) Vectors Two exemplary asymmetric antibodies as detailed in Example 10, were cloned into triple gene (TGV), double gene (DGV) and single gene (SGV) vectors, as follows:

The DNA and amino acid sequences of the full length heavy chain (HCB), truncated heavy chain (HCA) and the light chain (LC) of the ZMW-001 v1041 OAA were amended electronically by addition of sequence encoding antibody signal peptides at the 5' end, appropriate restriction enzyme sites to enable cloning into GS vectors and a Kozak sequence between the 5' restriction enzyme site and the 'ATG' start codon.

The DNA sequences encoding HCA, HCB and the LC were synthesized and supplied within three separate vectors. The HCB gene was cloned into the vector pEE21.4 to create the vector pZMW-001 v1041 HCB/SGV. The HCA gene was cloned into the vector pZMW-001 v1041 HCB/SGV to create the double gene vector (DGV) pZMW-001 v1041/DGV. The LC gene was cloned into the vector pEE12.4. pEE21.4 and pEE12.4 GS Gene Expression System™. The DGV containing the HC genes and the single gene vector (SGV) containing the LC gene were joined to generate a triple gene vector (TGV) containing the HCA, HCB and LC genes, as well as the GS gene.

Sufficient TGV DNA to be used for transient transfection and in the cell line construction process was generated and the HCA, HCB and LC genes within this DNA preparation were sequenced in both orientations. The DNA was then linearised with PvuI and prepared for stable transfection into CHOK1SV cells.

Example 12: Transient Co-Expression of One-Armed Asymmetric Antibody Variants Using Tri- and Bi-Cistronic Expression Vectors The asymmetric antibodies 1040 and 1041 were cloned in tri- and bi-cistronic expression vectors as indicated in Example 11. The expression vectors were then used to transiently transfect CHO CHOK1SV cells, transfections used either triple gene vectors (TGVs), or double gene vector (encoding for the Heavy chain constructs) plus single gene vector (encoding for the light chain construct) a 2:1 ratio. The expression products were purified by HiTrap Mab Select SuRE column (GE Healthcare), and SEC using a Zorbax GF250 column and analyzed by LC/MS. A summary of the results are shown in Table 1:

| Product | Recovery (mg) (from 200 ml CHO) | Titre (mg/L) | SEC analysis OAA product (%) | SEC analysis HMV/ LMV species (%) | LC/MS purity (% heterodimer) |
|---|---|---|---|---|---|
| v1040 (TGV) | 8.90 | 44.6 | 69.7 | 30.3 | ~85% (15% Fc-homodimer) |
| v1041 (TGV) | 3.93 (loss during pA) | 45.7 | 82.1 | 17.9 | ~85% (15% Fc-homodimer) |
| v1040 (GGV/SGV) | 6.22 | 31.1 | 85.8 | 14.2 | >90% (~6% Fc-homodimer) |
| v1041 (DGV/SGV) | 10.50 | 82.5 | 85.2 | 14.8 | >90% (~5% Fc-homodimer) |

FIG. 18A shows HPLC-SEC purification of the asymmetric antibodies expressed. FIG. 18B shows the LCMS analysis of the 1040 and 1041 asymmetric antibodies expressed using the TGV system.

Example 13: Stable Pool Generation Using the TGV System

Pools of stable transfectants expressing 1040 and 1041 using the TGV system were generated by transfecting CHOK1SV host cell line with the engineered TGV system, as described in Example 10, to generate pools of stable transfectants. Four pools of transfectants were selected for each variant based on the protein A titre and Capiler results of the 12 day batch cell culture supernatants. The cell culture supernatant of the pools were protein A purified and analysed by SOS reduced and non reduced and GPC. The expression products of each pool were analyzed by SDS-PAGE to determine purity. FIG. 19 shows the SDS-PAGE results and indicates that the main band in each lane corresponds to the desired product (Fc-HC-LC) for all 8 pools. The HC2-LC2 band (full-sized antibody homodimer) is very faint with the intensity higher in pools expressing 1041. The contaminant product at ~90 k0a appears of higher intensity in sample from pool 13B and 24A.

The expression product of the stable pools were subjected to SEC in order to analyze purity. The purity of the different pools for the 1040 variant are shown in FIG. 20A. The purity of the different pools for the 1041 variant are shown in FIG. 20B. FIG. 20A shows a purity of >91% is obtained with the four stable pools of v1040. FIG. 20B shows a purity of >86% is obtained with the four stable pools of v1041, as determined by SEC.

Example 14: Summary of Culture Protocols and Assessment

This example is related to the data in Example 8.

Block A: 120 rpm and 37° C.
Block B: 120 rpm and 36.5° C.
Block C: 110 rpm and 37° C.

Block A:

1. Selexis Process*: 30 mL working volume; 300,000 seeding density
2. Selexis Process*: 50 mL working volume; 300,000 seeding density
3. Selexis Process*: 30 mL working volume; 500,000 seeding density
4. KBI-1: 30 mL Working Volume; 300,000 seeding density; Cell Boost5: Day 0, 2 and 5 (26% Initial Volume)
5. KBI-2: 30 mL Working Volume; 300,000 seeding density; Cell Boost5: Day 0 (40% Initial Volume)
6. KBI-3: 30 mL Working Volume; 300,000 seeding density; Cell Boost5: Day 0 and 2 (16% Initial Volume)
7. KBI-4: 30 mL Working Volume; 300,000 seeding density; Cell Boost5: Day 0 and 5 (16% Initial Volume)
8. KBI-5: 30 mL Working Volume; 300,000 seeding density; Cell Boost5: Day 0, 2, 3, 6 and 7 (4, 8, 12, 16 and 16% Initial Volume, respectively)

Block B:

1. Selexis Process*: 30 mL working volume; 300,000 seeding density
2. Selexis Process*: 30 mL working volume; 500,000 seeding density
3. KBI-1: 30 mL Working Volume; 300,000 seeding density; Cell Boost5: Day 0, 2 and 5 (26% Initial Volume)
4. KBI-2: 30 mL Working Volume; 300,000 seeding density; Cell Boost5: Day 0 (40% Initial Volume)
5. KBI-3: 30 mL Working Volume; 300,000 seeding density; Cell Boost5: Day 0 and 2 (16% Initial Volume)
6. KBI-4: 30 mL Working Volume; 300,000 seeding density; Cell Boost5: Day 0 and 5 (16% Initial Volume)
7. KBI-5: 30 mL Working Volume; 300,000 seeding density; Cell Boost5: Day 0, 2, 3, 6 and 7 (4, 8, 12, 16 and 16% Initial Volume, respectively)

Block C:

1. Selexis Process*: 30 mL working volume; 300,000 seeding density
2. Selexis Process*: 50 mL working volume; 300,000 seeding density
3. KBI-5: 30 mL Working Volume; 300,000 seeding density; Cell Boost5: Day 0, 2, 3, 6 and 7 (4, 8, 12, 16 and 16% Initial Volume, respectively)

It has been demonstrated for viability assessment, Block A (120 rpm and 37° C.), the viability dropped significantly towards the end of the culture. For condition Block B (120 rpm and 36.5° C.) and Block C (110 rpm and 37° C.), where change in agitation and temperature were done, higher cell viabilities was maintained.

It has been demonstrated for growth assessment, Block A (120 rpm and 37° C.), cells saturated in growth and the culture started dropping in viable cell count significantly. For condition Block B (120 rpm and 36.5° C.). and Block C (110 rpm and 37° C.), where change in agitation and temperature were done, higher cell growth and viable cell numbers were attained.

It has been demonstrated for titre assessment, Block A (120 rpm and 37° C.). had lower titers and there is not much significant improvement in titers towards end of the culture mainly due to saturation of growth in the culture. For condition Block B (120 rpm and 36.5° C.). and Block C (110 rpm and 37° C.), higher titers is mainly due to higher cell growth.

It has been demonstrated that comparison of the performance of stable antibody expressing clones in the aforementioned manner permitted the selection of the top performing stable clone for further manufacturability assessment. Block A had similar growth and viabilities as the previous Shake Flask Study. With change in temperature and agitation (Blocks C and D) there was significant improvement in cell numbers which resulted in higher titers. Clones in All the blocks grew very similar for the beginning of culture however post Day 4, the cultures with changed agitation and temperature displayed higher growth and maintained higher viabilities too. It has been demonstrated that comparison of clones with the aforementioned cell culture criteria result in the selection of the top suitable stable antibody expressing clones for manufacturability assessment.

It is further contemplated that varying the aforementioned conditions can improve product purity and titres for a clone stably expressing asymmetric antibody as described in the invention.

All publications, patents and patent applications mentioned in this specification are herein incorporated by reference into the specification to the same extent as if each individual publication, patent or patent application was specifically and individually indicated to be incorporated herein by reference.

---

We claim:

1. A method of producing an asymmetric antibody product comprising a first heavy chain polypeptide and a second heavy chain polypeptide in stable mammalian cells, the method comprising:
   a. selecting a first heavy chain polypeptide sequence and a second heavy chain polypeptide sequence, each of the first and second heavy chain polypeptide sequences comprising a variant CH3 sequence, wherein the variant CH3 sequence of the first heavy chain polypeptide sequence is different from the variant CH3 sequence of the second heavy chain polypeptide sequence,
   wherein the variant CH3 sequence of the first heavy chain polypeptide comprises amino acid modifications at positions F405A and Y407V, optionally in combination with amino acid modification L351Y, and the variant CH3 sequence of the second heavy chain polypeptide comprises amino acid modifications T366L and T394W, optionally in combination with amino acid modifications K392L or K392M,
   wherein the variant CH3 sequences of the first and second heavy chain polypeptides promote formation of a heterodimeric Fc region with a CH3 domain having a Tm greater than 75° C., and
   wherein at least one of the first heavy chain polypeptide and the second heavy chain polypeptide further comprises a single domain antigen binding protein module or a single chain antigen binding protein module;
   b. (i) transfecting at least two different mammalian cells with different ratios of a first DNA sequence encoding the first heavy chain polypeptide sequence and a second DNA sequence encoding the second heavy chain polypeptide:
   and
   (ii) selecting, as a pre-determined ratio, a ratio of the first DNA sequence and the second DNA sequence that results in a mammalian cell line that produces greater than 75% asymmetric antibody product, less than 10% monomers, and undetectable amounts of homodimers of the first or second heavy chain polypeptide;
   c. transfecting at least one mammalian cell with the pre-determined ratio of the first DNA sequence and the second DNA sequence to generate stable mammalian cells; and
   d. culturing said stable mammalian cells under conditions suitable for expression of the first and second heavy chain polypeptides to produce the asymmetric antibody product, whereby stable mammalian cells producing greater than 75% asymmetric antibody product, less than 10% monomers, and undetectable amounts of homodimers of the first or second heavy chain polypeptide are obtained at a frequency of greater than 1 in 500.

2. The method of claim 1, wherein at least one of the first heavy chain polypeptide and the second heavy chain polypeptide further comprises a single domain antigen binding protein module which is a fibronectin domain, an adnectin, a human Vh domain, or a heavy-chain antibody domain, or a fragment thereof.

3. The method of claim 2, wherein the single domain antigen binding protein module is a heavy-chain antibody domain derived from a camelid heavy-chain antibody domain or a shark heavy-chain antibody domain.

4. The method of claim 1, wherein at least one of the first heavy chain polypeptide and the second heavy chain polypeptide further comprises a single chain antigen binding protein module which is a scFv or a scFab.

5. The method of claim 1, wherein the first heavy chain polypeptide further comprises a single domain antigen binding protein module which is a fibronectin domain, an adnectin, a human Vh domain, or a heavy-chain antibody domain, or a fragment thereof, and wherein the second heavy chain polypeptide further comprises a single chain antigen binding protein module which is a scFv or a scFab.

6. The method of claim 1, wherein:
   A. the variant CH3 sequence of the first heavy chain polypeptide comprises the amino acid modifications L351Y, F405A, and Y407V, and the variant CH3 sequence of the second heavy chain polypeptide comprises the amino acid modifications T366L, K392M, and T394W;
   B. the variant CH3 sequence of the first heavy chain polypeptide comprises the amino acid modifications L351Y, F405A, and Y407V, and the variant CH3 sequence of the second heavy chain polypeptide comprises the amino acid modifications T366L, K392L, and T394W;
   C. the variant CH3 sequence of the first heavy chain polypeptide comprises the amino acid modifications T350V, L351Y, F405A, and Y407V, and the variant CH3 sequence of the second heavy chain polypeptide comprises the amino acid modifications T350V, T366L, K392M, and T394W, or
   D. the variant CH3 sequence of the first heavy chain polypeptide comprises the amino acid modifications T350V, L351Y, F405A, and Y407V, and the variant CH3 sequence of the second heavy chain polypeptide comprises the amino acid modifications T350V, T366L, K392L, and T394W.

7. The method of claim 1, wherein the stable mammalian cells produce the asymmetric antibody product with a titer of greater than 100 mg/L.

8. The method of claim 1, wherein the at least one mammalian cell is selected from the group consisting of a VERO, Hela, HEK, NSO, Chinese Hamster Ovary (CHO), W138, BHK, COS-7, Caco-2 and MOCK cell, and subclasses and variants thereof.

9. The method of claim 1, wherein the at least one mammalian cell is one that produces a glycosylated asymmetric antibody product.

10. The method of claim 1, wherein the at least one mammalian cell is a pool of mammalian cells.

11. The method of claim 1, further comprising the step of selecting a stable monoclonal mammalian cell that produces greater than 75% asymmetric antibody product, less than 10% monomers, and undetectable amounts of homodimers of the first or second heavy chain polypeptide from the stable mammalian cells generated in step d.

12. The method of claim 1, wherein the amount of asymmetric antibody product, monomer and homodimer is determined by SDS-PAGE, liquid chromatography, mass spectrometry, or a combination thereof.

13. The method of claim 1, wherein the ratio of first DNA sequence:second DNA sequence in the transfected cell is such that amount of translated first heavy chain polypeptide is about equal to the amount of translated second heavy chain polypeptide.

14. The method of claim 1, wherein
the variant CH3 sequence of the first heavy chain polypeptide further comprises the amino acid modification S400E, and the variant CH3 sequence of the second heavy chain polypeptide further comprises the amino acid modification N390R.

15. The method of claim 6, wherein the variant CH3 sequence of the first heavy chain polypeptide further comprises the amino acid modification S400E, and the variant CH3 sequence of the second heavy chain polypeptide further comprises the amino acid modification N390R.

16. The method of claim 2, wherein the first heavy chain polypeptide and the second heavy chain polypeptide each further comprise a single domain antigen binding protein module independently selected from a human Vh domain and a heavy-chain antibody domain.

17. The method of claim 4, wherein the first heavy chain polypeptide and the second heavy chain polypeptide each further comprise a single chain antigen binding protein module which is a scFv.

18. The method of claim 1, wherein the stable mammalian cells produce greater than 95% asymmetric antibody product, less than 5% monomers, and undetectable amounts of homodimers comprising either the first or second heavy chain polypeptide.

19. The method of claim 1, wherein step b. comprises transiently transfecting the at least two different mammalian cells.

20. The method of claim 1, wherein step b. comprises stably transfecting the at least two different mammalian cells.

21. The method of claim 1, wherein the first and second heavy chain polypeptides preferentially exist as monomers rather than homodimers when not in the form of a heterodimer pair.

22. A stable monoclonal mammalian cell produced by the method of claim 11.

23. The stable monoclonal mammalian cell of claim 22, wherein:
a. the variant CH3 sequence of the first heavy chain polypeptide comprises the amino acid modifications L351Y, F405A, and Y407V, and the variant CH3 sequence of the second heavy chain polypeptide comprises the amino acid modifications T366L, K392M, and T394W;
b. the variant CH3 sequence of the first heavy chain polypeptide comprises the amino acid modifications L351Y, F405A, and Y407V, and the variant CH3 sequence of the second heavy chain polypeptide comprises the amino acid modifications T366L, K392L, and T394W;
c. the variant CH3 sequence of the first heavy chain polypeptide comprises the amino acid modifications T350V, L351Y, F405A, and Y407V, and the variant CH3 sequence of the second heavy chain polypeptide comprises the ammo acid modifications T350V, T366L, K392M, and T394W; or
d. the variant CH3 sequence of the first heavy chain polypeptide comprises the amino acid modifications T350V, L351Y, F405A, and Y407V, and the variant CH3 sequence of the second heavy chain polypeptide comprises the amino acid modifications T350V, T366L, K392L, and T394W.

24. The stable monoclonal mammalian cell of claim 23, wherein the variant CH3 sequence of the first heavy chain polypeptide further comprises the amino acid modification S400E, and the variant CH3 sequence of the second heavy chain polypeptide further comprises the amino acid modification N390R.

25. A method of producing an asymmetric antibody product comprising a first heavy chain polypeptide and a second heavy chain polypeptide in stable mammalian cells, the method comprising:
a. transfecting at least one mammalian cell with a predetermined ratio of:
i) a first DNA sequence encoding the first heavy chain polypeptide, wherein the first heavy chain polypeptide comprises a variant CH3 sequence, and
ii) a second DNA sequence encoding the second heavy chain polypeptide, wherein the second heavy chain polypeptide comprises a variant CH3 sequence different from the first heavy chain polypeptide,
to generate stable mammalian cells, and
b. culturing the stable mammalian cells under conditions suitable for expression of the first and second heavy chain polypeptides to produce the asymmetric antibody product,
wherein the stable mammalian cells produce greater than 75% of the asymmetric antibody product, less than 10% monomers, and undetectable amounts of homodimers of the first or second heavy chain polypeptide,
wherein the variant CH3 sequence of the first heavy chain polypeptide comprises amino acid modifications F405A and Y407V, optionally in combination with amino acid modification L351Y, and the variant CH3 sequence of the second heavy chain polypeptide comprises amino acid modifications T366L and T394W, optionally in combination with amino acid modifications K392L or K392M,
wherein the variant CH3 sequences of the first and second heavy chain polypeptides promote formation of a heterodimeric Fc region with a CH3 domain having a Tm greater than 75° C., and
wherein at least one of the first heavy chain polypeptide and the second heavy chain polypeptide further comprises a single domain antigen binding protein module or a single chain antigen binding protein module.

26. The method of claim 25, wherein at least one of the first heavy chain polypeptide and the second heavy chain polypeptide further comprises a single domain antigen binding protein module which is a fibronectin domain, an adnectin, a human Vh domain, or a heavy-chain antibody domain, or a fragment thereof.

27. The method of claim 25, wherein at least one of the first heavy chain polypeptide and the second heavy chain polypeptide further comprises a single chain antigen binding protein module which is a scFv or a scFab.

28. The method of claim 26, wherein the first heavy chain polypeptide and the second heavy chain polypeptide each independently further comprise a single domain antigen binding protein module independently selected from a human Vh domain and a heavy-chain antibody domain.

29. The method of claim 27, wherein the first heavy chain polypeptide and the second heavy chain polypeptide each further independently comprise a single chain antigen binding protein module which is a scFv.

30. The method of claim 25, wherein:
A. the variant CH3 sequence of the first heavy chain polypeptide comprises the amino acid modifications L351Y, F405A, and Y407V, and the variant CH3 sequence of the second heavy chain polypeptide comprises the amino acid modifications T366L, K392M, and T394W;
B. the variant CH3 sequence of the first heavy chain polypeptide comprises the amino acid modifications L351Y, F405A, and Y407V, and the variant CH3 sequence of the second heavy chain polypeptide comprises the amino acid modifications T366L, K392L, and T394W;
C. the variant CH3 sequence of the first heavy chain polypeptide comprises the amino acid modifications T350V, L351Y, F405A, and Y407V, and the variant CH3 sequence of the second heavy chain polypeptide comprises the amino acid modifications T350V, T366L, K392M, and T394W, or
D. the variant CH3 sequence of the first heavy chain polypeptide comprises the amino acid modifications T350V, L351Y, F405A, and Y407V, and the variant CH3 sequence of the second heavy chain polypeptide comprises the amino acid modifications T350V, T366L, K392L, and T394W.

31. The method of claim 30, wherein the variant CH3 sequence of the first heavy chain polypeptide further comprises the amino acid modification S400E, and the variant CH3 sequence of the second heavy chain polypeptide further comprises the amino acid modification N390R.

32. The method of claim 25, further comprising the step of selecting a stable monoclonal mammalian cell that produces greater than 75% asymmetric antibody product, less than 10% monomers, and undetectable amounts of homodimers of said first or second heavy chain polypeptide from the stable mammalian cells generated in step b.

33. The method of claim 32, wherein the frequency of obtaining stable monoclonal mammalian cells producing greater than 75% asymmetric antibody product, less than 10% monomers, and undetectable amounts of homodimers of said first or second heavy chain polypeptide is greater than 1 in 500.

34. The method of claim 25, wherein the first and second heavy chain polypeptides preferentially exist as monomers rather than homodimers when not in the form of a heterodimer pair.

35. The method of claim 1, wherein the variant CH3 sequence of the first and/or the second heavy chain polypeptide further comprises the amino acid modification T350V.

36. The stable monoclonal mammalian cell of claim 22, wherein the variant CH3 sequence of the first and/or the second heavy chain polypeptide further comprises the amino acid modification T350V.

37. The method of claim 25, wherein the variant CH3 sequence of the first and/or the second heavy chain polypeptide further comprises the amino acid modification T350V.

* * * * *

UNITED STATES PATENT AND TRADEMARK OFFICE
CERTIFICATE OF CORRECTION

PATENT NO. : 10,508,154 B2
APPLICATION NO. : 15/355019
DATED : December 17, 2019
INVENTOR(S) : Surjit Bhimarao Dixit, Gordon Yiu Kon NG and Thomas Spreter Von Kreudenstein It is certified that error appears in the above-identified patent and that said Letters Patent is hereby corrected as shown below:

On the Title Page

(73) Assignee, please delete "ZYMEWORKS INC," and insert --ZYMEWORKS BC INC.--

Signed and Sealed this
Thirtieth Day of May, 2023

Katherine Kelly Vidal
*Director of the United States Patent and Trademark Office*